US010443060B2

(12) United States Patent
Saville et al.

(10) Patent No.: US 10,443,060 B2
(45) Date of Patent: Oct. 15, 2019

(54) NUCLEIC ACIDS AND VECTORS FOR USE WITH METHANOTROPHIC BACTERIA

(71) Applicant: Calysta, Inc., Menlo Park, CA (US)

(72) Inventors: Renee M. Saville, Mountain View, CA (US); Joshua Silverman, Los Altos Hills, CA (US); Jeremy Minshull, Los Altos, CA (US); Jon Edward Ness, Redwood City, CA (US); Effendi Leonard, Anaheim, CA (US); Jana Stumpe, Sunnyvale, CA (US); Mark Welch, Fremont, CA (US)

(73) Assignee: CALYSTA, INC., Menlo Park, CA (US)

( * ) Notice: Subject to any disclaimer, the term of this patent is extended or adjusted under 35 U.S.C. 154(b) by 0 days.

(21) Appl. No.: 15/319,312

(22) PCT Filed: Jun. 18, 2015

(86) PCT No.: PCT/US2015/036515
§ 371 (c)(1),
(2) Date: Dec. 15, 2016

(87) PCT Pub. No.: WO2015/195972
PCT Pub. Date: Dec. 23, 2015

(65) Prior Publication Data
US 2017/0121718 A1 May 4, 2017

Related U.S. Application Data

(60) Provisional application No. 62/014,007, filed on Jun. 18, 2014.

(51) Int. Cl.
*C12N 15/74* (2006.01)
*C12N 9/04* (2006.01)

(52) U.S. Cl.
CPC .......... *C12N 15/74* (2013.01); *C12N 9/0006* (2013.01); *C12Y 101/01244* (2013.01); *C12N 2830/002* (2013.01)

(58) Field of Classification Search
None
See application file for complete search history.

(56) References Cited

U.S. PATENT DOCUMENTS

| | | | |
|---|---|---|---|
| 6,258,565 | B1 | 7/2001 | Blatny et al. |
| 7,705,203 | B2 | 4/2010 | Hodges et al. |
| 8,216,821 | B2 | 7/2012 | Miguez et al. |
| 2001/0016351 | A1 | 8/2001 | Sorge et al. |
| 2003/0003525 | A1 | 1/2003 | Valla et al. |
| 2005/0202544 | A1 | 9/2005 | Retallack et al. |
| 2006/0057726 | A1 | 3/2006 | Sharpe |
| 2012/0183503 | A1 | 7/2012 | Steidler et al. |

FOREIGN PATENT DOCUMENTS

| | | |
|---|---|---|
| WO | 2004/005221 A2 | 1/2004 |
| WO | 2004011628 A1 | 2/2004 |
| WO | 2007/055737 A2 | 5/2007 |
| WO | 2012/116338 A1 | 8/2012 |
| WO | 2014/066670 A1 | 5/2014 |
| WO | 2014/138419 A1 | 9/2014 |
| WO | 2014/205146 A1 | 12/2014 |
| WO | 2015/109257 A1 | 7/2015 |
| WO | 2015/109265 A1 | 7/2015 |

OTHER PUBLICATIONS

Accession AAN60791. Mar. 25, 2003 (Year: 2003).*
Balzer et al., "A comparative analysis of the properties of regulated promoter systems commonly used for recombinant gene expression in *Escherichia coli*," *Microbial Cell Factories* 12:26, 14 pages (2013).
Blatny et al., "Construction and Use of a Versatile Set of Broad-Host-Range Cloning and Expression Vectors Based on the RK2 Replicon," *Applied and Environmental Microbiology* 63(2):370-379 (Feb. 1997).
Blatny et al., "Improved Broad-Host-Range RK2 Vectors Useful for High and Low Regulated Gene Expression Levels in Gram-Negative Bacteria," *Plasmid* 38:35-51 (1997).
Brautaset et al., "Positively regulated bacterial expression systems," *Microbial Biotechnology* 2(1):15-30 (2009).
Cowles et al., "BenR, a Xy1S Homologue, Regulates Three Different Pathways of Aromatic Acid Degradation in *Pseudomonas putida*," *Journal of Bacteriology* 182(22):6339-6346 (Nov. 2000).
Franklin et al., "Molecular and functional analysis of the TOL plasmid pWWO from *Pseudomonas putida* and cloning of genes for the entire regulated aromatic ring *meta* cleavage pathway," *Proc. Natl. Acad. Sci. USA* 78(12):7458-7462 (Dec. 1981).
Gallegos et al., "AraC/Xy1S Family of Transcriptional Regulators," *Microbiology and Molecular Biology Reviews* 61(4):393-410 (Dec. 1997).
Li et al., "Genome-wide investigation and functional characterization of the α-ketoadipate pathway in the nitrogen-fixing and root-associated bacterium *Pseudomonas stutzeri* A1501," *BMC Microbiology* 10:36, 14 pages. (2010).

(Continued)

*Primary Examiner* — Christian L Fronda
(74) *Attorney, Agent, or Firm* — Seed IP Law Group LLP

(57) ABSTRACT

The present disclosure provides nucleic acids and vectors for use with methanotrophic bacteria. Related host cells and methods for using such nucleic acids and vectors for expressing polypeptides or other genetic manipulation of methanotrophic bacteria are also provided. In one aspect, the present disclosure is directed to a non-naturally occurring nucleic acid molecule, comprising (1) a promoter that is functional in a methanotrophic bacterium, and (2) a native or altered methanol dehydrogenase (MDH) ribosomal binding sequence, provided that when the promoter is an MDH gene promoter, the nucleic acid comprises an altered MDH ribosomal binding sequence.

24 Claims, 18 Drawing Sheets
Specification includes a Sequence Listing.

(56) References Cited

OTHER PUBLICATIONS

Martin et al., "The AraC transcriptional activators," *Current Opinion in Microbiology* 4:132-137 (2001).
Mulvey et al., "Ambler Class A Extended-Spectrum Beta-Lactamase-Producing *Escherichia coli* and *Klebsiella* spp. in Canadian Hospitals," *Antimicrobial Agents and Chemotherapy* 48(4):1204-1214 (2004).
Ramos et al., "Regulatory circuits controlling transcription of TOL plasmid operon encoding *meta*-cleavage pathway for degradation of alkylbenzoates by *Pseudomonas*," *Molecular Microbiology* 1(3): 293-300 (1987).
Retallack et al., "Identification of anthranilate and benzoate metabolic operons of *Pseudomonas fluorescens* and functional characterization of their promoter regions," *Microbial Cell Factories* 5:1, 13 pages (2006).
Silva-Rocha et al., "Broadening the signal specificity of prokaryotic promoters by modifying *cis*-regulatory elements associated with a single transcription factor," *Mol. BioSyst.* 8:1950-1957 (2012).
Smith et al., "Improved System for Protein Engineering of the Hydroxylase Component of Soluble Methane Monooxygenase," *Applied and Environmental Microbiology* 68(11):5265-5273 (2002).
Ward et al., "Genomic Insights into Methanotrophy: The Complete Genome Sequence of *Methylococcus capsulatus* (Bath)," *PLoS Biology*, 2(10):e303, 1616-1628 (Oct. 2004).
Winther-Larsen et al., "Parameters Affecting Gene Expression from the *Pm* Promoter in Gram-Negative Bacteria," *Metabolic Engineering* 2:79-91 (2000).
Zwick et al., "Regulation of the expression level of transcription factor Xyl S reveals new functional insight into its induction mechanism at the *Pm* promoter," *BMC Microbiology* 13:262, 12 pages (2013).
Ali et al., "Development and validation of promoter-probe vectors for the study of methane monooxygenase gene expression in *Methylococcus capsulatus* Bath,"*Microbiology* 155: 761-771 (2009).
Figueira et al., "Production of green fluorescent protein by the methylotrophic bacterium *Methylobacterium extorquens*," *FEMS Microbiology Letters* 193: 195-200 (2000).
Hanson et al., "Methanotrophic Bacteria," *Microbiological Reviews* 60(2): 439-471 (Jun. 1996).

* cited by examiner

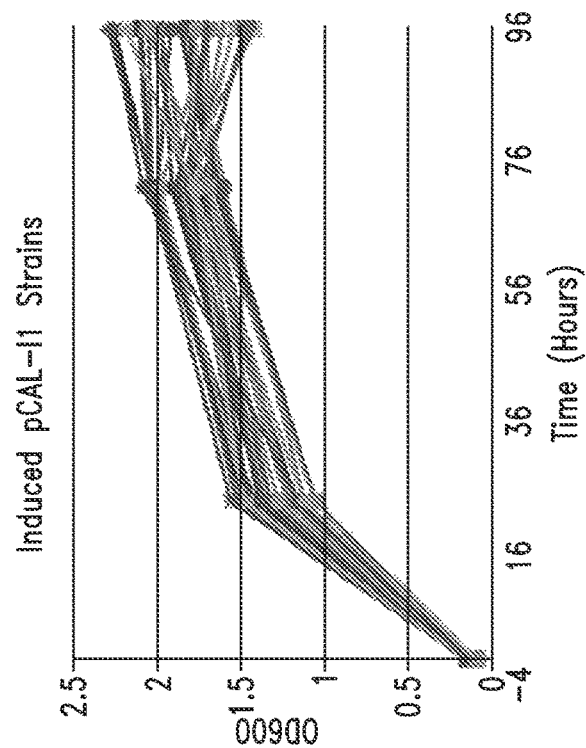
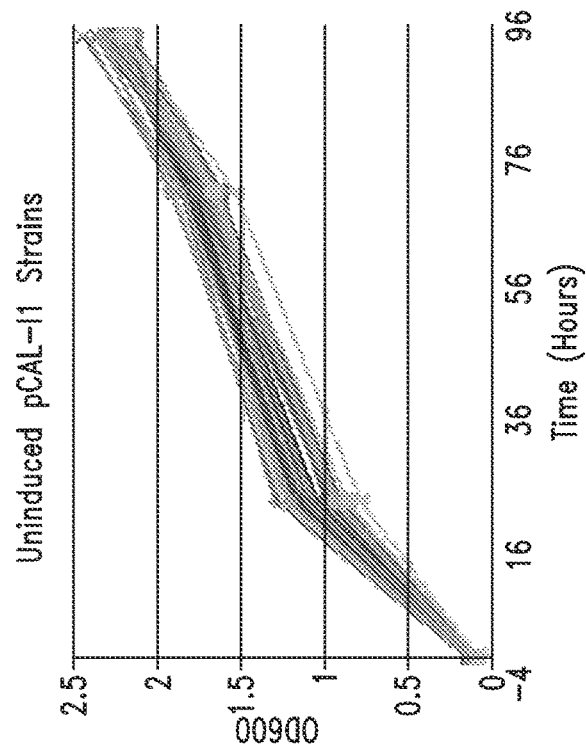

NUCLEIC ACIDS AND VECTORS FOR USE WITH METHANOTROPHIC BACTERIA

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_413USPC_SEQUENCE_LISTING.txt. The text file is 42.3 KB, was created on Dec. 14, 2016, and is being submitted electronically via EFS-Web.

BACKGROUND

Methanotrophic bacteria require single-carbon compounds to survive and are able to metabolize methane as their only source of carbon and energy. They are of special interest in reducing the release of methane into the atmosphere from high methane-producing environments and in reducing certain environmental contaminants such as chlorinated hydrocarbons.

In spite of the importance of methanotrophic bacteria, genetic manipulation of such bacteria has historically been difficult due to a lack of robust protocols and tools such as vectors, expression cassettes, and suitable promoters (see, e.g., Ali and Murrel, Microbiology 155:761-71, 2009). Where such tools exist, various issues have hindered their use, including methanotroph-incompatible antibiotic resistance markers, inappropriate restriction sites, and poorly expressed proteins.

BRIEF SUMMARY

In one aspect, the present disclosure is directed to a non-naturally occurring nucleic acid molecule, comprising (1) a promoter that is functional in a methanotrophic bacterium, and (2) a native or altered methanol dehydrogenase (MDH) ribosomal binding sequence, provided that when the promoter is an MDH gene promoter, the nucleic acid comprises an altered MDH ribosomal binding sequence.

In another aspect, the present disclosure is directed to a non-naturally occurring nucleic acid molecule, comprising: (1) a promoter selected from an MDH promoter, 30S ribosomal protein S16 promoter, 30S ribosomal protein S12 promoter, 50S ribosomal protein L13 promoter, hexulose 6-phosphate synthase promoter, T5 promoter, or Trc promoter, and (2) a ribosomal binding sequence that is functional in a methanotrophic bacterium, provided that if the promoter sequence and the ribosomal binding sequence are from the same gene, then at least one of the sequences are not a native sequence.

In any of the previous aspects, a promoter may be a constitutive promoter. In some embodiments, the constitutive promoter is selected from an MDH promoter, 30S ribosomal protein S16 promoter, 30S ribosomal protein S12 promoter, 50S ribosomal protein L13 promoter, hexulose 6-phosphate synthase promoter, T5 promoter, and Trc promoter. In some embodiments, the promoter may be a MDH promoter comprising a promoter portion of SEQ ID NO.:14, a 30S ribosomal protein S16 promoter comprising a promoter portion of SEQ ID NO.:15, a 30S ribosomal protein S12 promoter comprising a promoter portion of SEQ ID NO.:43, a 50S ribosomal protein L13 promoter comprising a promoter portion of SEQ ID NO.:44, a hexulose 6-phosphate synthase promoter comprising a promoter portion of SEQ ID NO.:16, a T5 promoter comprising a promoter portion of SEQ ID NO.:17, or a Trc promoter comprising a promoter portion of SEQ ID NO.:18.

In any of the previous aspects, the promoter may be an inducible promoter.

In any of the previous aspects, the MDH ribosomal binding sequence may be a native or altered MDH ribosomal binding sequence. For example, in some embodiments, the MDH ribosomal binding sequence is a native MDH ribosomal binding sequence comprising SEQ ID NO.:40. In some embodiments, the MDH ribosomal binding sequence is an altered MDH ribosomal binding sequence, encoding (1) a native MDH ribosomal binding site and a variant spacer, (2) a variant MDH ribosomal binding site and a native spacer, or (3) a variant MDH ribosomal binding site and a variant spacer. In some embodiments, the altered MDH ribosomal binding sequence comprises SEQ ID NO.: 20, 22, 24, 26, 27, 31, 32, or 41.

In any of the previous aspects, a nucleic acid may further comprise a nucleic acid molecule encoding a target polypeptide operably linked to the promoter and the ribosomal binding sequence.

In some embodiments, the target polypeptide is LacI repressor protein and the nucleic acid further comprises a second promoter, a lac operator to which LacI repressor protein is capable of binding, and a sequence encoding a second target polypeptide, wherein the second promoter and the lac operator are operably linked to the nucleic acid molecule encoding the second target polypeptide. In some embodiments, the second target polypeptide is a marker protein, a reporter protein, or a protein capable of improving production of a desired chemical or metabolite (such as an isoprene synthase or lactate dehydrogenase). In some embodiments, the second promoter is an MDH promoter. For example, in some embodiments, the second promoter may comprise an MDH promoter portion of SEQ ID NO.: 14.

In some aspects, the present disclosure is directed to a non-naturally occurring nucleic acid, comprising: (1) an inducible promoter that comprises an operator of the lac operon and is functional in a methanotrophic bacterium; (2) a first ribosomal binding sequence; (3) a nucleic acid molecule encoding a target protein; (4) a constitutive promoter that is functional in a methanotrophic bacterium; (5) a second ribosomal binding sequence; and (6) a nucleic acid molecule encoding a LacI protein; wherein the nucleic acid sequence encoding the target protein (3) is operably linked to the inducible promoter (1) and the ribosomal biding sequence (2), and the nucleic acid molecule encoding a repressor or activator protein (6) is operably linked to the constitutive promoter (4) and second ribosomal binding sequence (5).

In one aspect, the present disclosure is directed to a non-naturally occurring nucleic acid, comprising: (1) an MDH promoter flanked by two or more operators of the lac operon; (2) a first MDH ribosomal binding sequence; (3) a nucleic acid molecule encoding a target polypeptide operably linked to sequences (1) and (2); (4) a 30S ribosomal protein S16 promoter; (5) a second MDH ribosomal binding sequence; and (6) a nucleic acid molecule encoding a repressor or activator protein operably linked to promoter (4) and ribosomal binding sequence (5).

In some embodiments, the target polypeptide is a BenR activator protein and the nucleic acid further comprises a second promoter and a nucleic acid molecule encoding a second target polypeptide, wherein the second promoter is operably linked to the nucleic acid molecule encoding the second target polypeptide. In some embodiments, the second promoter is a Pben promoter, for example, the promoter portion of SEQ ID NO.:48.

In some aspects, the present disclosure is directed to a non-naturally occurring nucleic acid, comprising: (1) an inducible promoter that comprises a promoter region of the benzoate metabolic operon and is functional in a methanotrophic bacterium; (2) a first ribosomal binding sequence; (3) a nucleic acid molecule encoding a target protein; (4) a constitutive promoter that is functional in a methanotrophic bacterium; (5) a second ribosomal binding sequence; and (6) a nucleic acid molecule encoding a BenR protein; wherein the nucleic acid molecule encoding the target protein (3) is operably linked to the inducible promoter (1) and the first ribosomal binding sequence (2), and the nucleic acid molecule encoding the BenR protein (6) is operably linked to the constitutive promoter (4) and the second ribosomal binding sequence (5).

In some aspects, the present disclosure is directed to a non-naturally occurring nucleic acid, comprising: (1) a ribosomal protein promoter; (2) an MDH ribosomal binding sequence; (3) a nucleic acid molecule encoding BenR, operably linked to promoter (1) and ribosomal binding sequence (2); (4) a $P_{ben}$ promoter; (5) a benA ribosomal binding sequence; and (6) a nucleic acid molecule encoding a target protein operably linked to promoter (4) and ribosomal binding sequence (5).

In any of the above aspects, the target polypeptide may be a marker protein, reporter protein, an enzyme, a protein capable of improving production of a desired chemical or metabolite (such as an isoprene synthase or lactate dehydrogenase), a LacI repressor protein, a BenR activator protein, or any combination thereof.

In other aspects, the present application is directed to a vector, comprising the nucleic acid of any of the previous aspects.

In yet another aspect, the present disclosure is directed to a method for producing a target polypeptide comprising culturing a host cell under conditions and for a time sufficient to express the target polypeptide. In some embodiments, the method comprises culturing a host cell in the presence of an inducer that binds to the lacI repressor protein to express the second target polypeptide. In other embodiments, the method comprises culturing the host cell in the presence of an inducer that binds to the BenR protein to express the second target polypeptide.

In yet another aspect, the present disclosure is directed to a vector, comprising: (1) a beta-lactamase (bla) or neomycin phosphotransferase (neo) promoter sequence operably linked to a sequence encoding a TrfA protein, and (2) an origin of vegetative replication (oriV) that is functional in a methanotrophic bacterium, and (3) optionally, (3) an origin of transfer (oriT). In some embodiments, the vector further comprises (4) a kanamycin resistance cassette.

In still other aspects, the present application is directed to a host cell comprising the nucleic acid or vector of any of the previous aspects. In some embodiments, the host cell is a *Methylococcus* or *Methylosinus*. For example, in some embodiments the host cell may be *Methylococcus capsulatus* or *Methylosinus trichosporium*.

BRIEF DESCRIPTION OF THE DRAWINGS

FIGS. 14A to 14D are graphs showing the effect on growth of *M. capsulatus* Bath having reduced expression of metabolic enzyme in the uninduced state from the pCAL-I2 expression construct relative to the pCAL-I1 expression construct. In the "induced" condition, cells were grown for 24 hours and then 10 mM IPTG was added to the cultures. No IPTG was added to the cultures in the "uninduced" condition. Metabolic enzyme catalyzed the formation of a metabolite that is toxic to the cells. Reduced expression in an uninduced state (e.g., tighter control of "leakage" of expression of a gene coding for metabolic enzyme) enabled unhindered growth of the cells prior to induction.

DETAILED DESCRIPTION

Figure 1A:
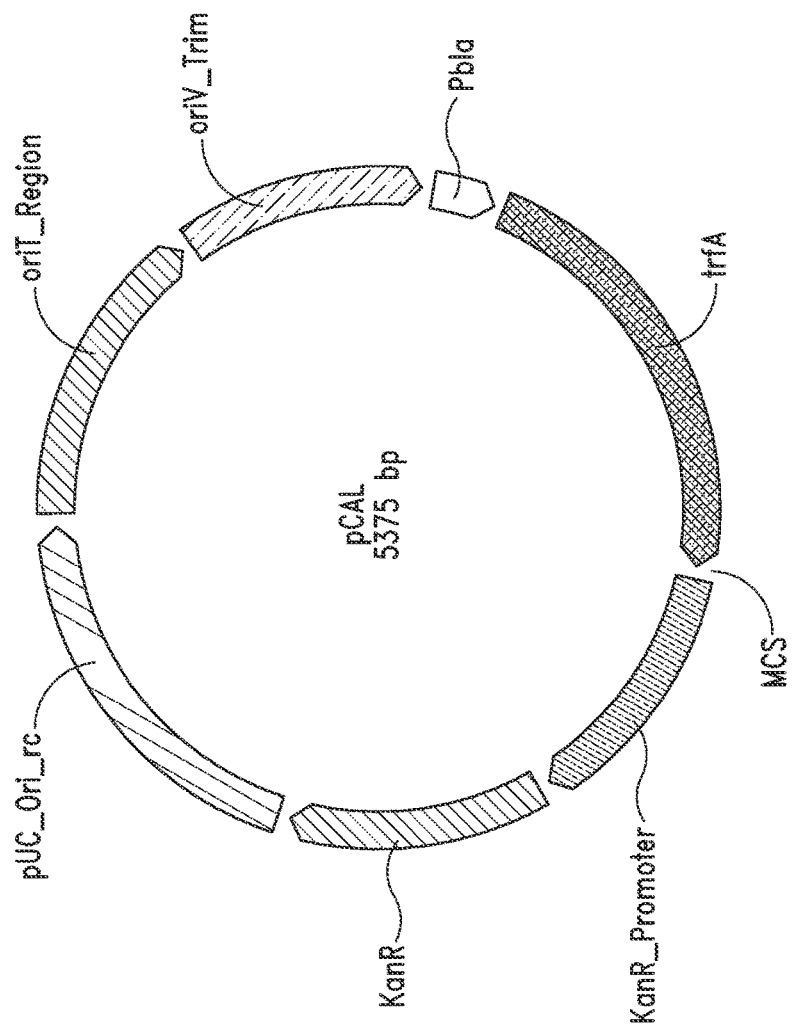
FIG. 1A is a schematic representation of shuttle vector pCAL comprising sequences encoding a replication initiation protein (trfA) and promoter (Pbla), an origin of replication (oriV), an origin of transfer (oriT), multiple cloning sites (MCS), kanamycin resistance gene (KanR) and promoter (KanR_promoter) and origin of replication for *E. coli* (pUC_Ori_rc). The pCAL vector can be used to carry the expression cassettes of the present disclosure for genetic engineering or modifying of methanotrophic bacteria by, for example, conjugation.

The present disclosure provides non-naturally occurring nucleic acids, vectors, host cells and methods for using the same, especially for producing target polypeptides in methanotrophic bacteria. The non-naturally occurring nucleic acids provided herein (e.g., expression nucleic acid molecules or expression cassettes, both constitutive and inducible) can be used to promote or regulate expression of target genes to reach desirable expression levels in methanotrophic bacteria. The vectors provided herein (e.g., pCAL), which can contain expression nucleic acid molecules of this disclosure, facilitate reliable and robust genetic manipulation of methanotrophic bacteria by one or more of the following: improving transformation efficiency in methanotrophic bacteria, improved regulation of target gene expression, increasing expression of target genes, reducing the sizes of essential or important components of the vectors, and allowing easier genetic manipulation in bacteria other than methanotrophic bacteria, such as *E. coli*.

Recombinant DNA, molecular cloning, and gene expression techniques used in the present disclosure are known in the art and described in references, such as Sambrook et al., Molecular Cloning: A Laboratory Manual, $3^{rd}$ Ed., Cold Spring Harbor Laboratory, New York, 2001, and Ausubel et al., Current Protocols in Molecular Biology, John Wiley and Sons, Baltimore, Md., 1999.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

I. Gene Expression

In one aspect, the present disclosure provides nucleic acid molecules useful in promoting or regulating gene expression in methanotrophic bacteria, vectors and host cells comprising such expression nucleic acid molecules, and methods for using such expression nucleic acid molecules in the form of expression cassettes carried by a vector for regulating gene expression and producing polypeptides of interest.

A. Expression Regulatory Nucleic Acid Molecules

In one aspect, the present disclosure provides non-naturally occurring or genetically engineered nucleic acid molecules that promote or regulate gene expression. In certain embodiments, a non-naturally occurring nucleic acid molecule comprises: (1) a promoter that is functional in a methanotrophic bacterium, and (2) a native or modified (variant) methanol dehydrogenase (MDH) ribosome binding sequence (RBS, also referred to as a "ribosomal binding sequence"). A non-naturally occurring nucleic acid molecule or genetically engineered nucleic acid molecule is also referred to herein as an "expression regulatory nucleic acid molecule" or "engineered expression regulatory nucleic acid molecule."

Nucleic acid molecules, also known as polynucleotides, are polymeric compounds comprised of covalently linked nucleotides. Nucleic acids include polyribonucleic acid (RNA), and polydeoxyribonucleic acid (DNA), both of which may be single- or double-stranded. The non-naturally occurring nucleic acid molecules provided herein are typically DNA molecules or fragments, which may be single- or double-stranded.

As used herein, the term "non-naturally occurring" or "engineered" refers to not occurring or existing in nature.

A "non-naturally occurring nucleic acid molecule" refers to a nucleic acid molecule having one or more engineered nucleotide differences (substitution, deletion or both) from a naturally occurring nucleic acid. A non-naturally occurring nucleic acid molecule may include one or more naturally occurring nucleic acid components (e.g., promoter, operator, RBS) as long as the nucleic acid molecule as a whole is not naturally occurring. For example, two naturally occurring control sequences may individually occur naturally but not found linked in nature, so these two molecules genetically engineered to be linked and function together (e.g., in trans) comprise a non-naturally occurring nucleic acid molecule of this disclosure.

Representative non-naturally occurring nucleic acid molecules may comprise (1) a naturally occurring promoter, and (2) a non-naturally occurring or engineered MDH ribosomal binding sequence. In further embodiments, a non-naturally occurring nucleic acid molecule may comprise (1) a non-naturally occurring promoter, and (2) a native (i.e., a naturally occurring) MDH ribosomal binding sequence. In still further embodiments, a non-naturally occurring nucleic acid molecule may comprise (1) a naturally occurring promoter other than a promoter from an MDH gene, and (2) a native MDH ribosomal binding sequence. In yet further embodiments, a non-naturally occurring nucleic acid molecule may comprise (1) a naturally occurring promoter other than a MDH promoter, and (2) a non-naturally occurring or engineered MDH ribosomal binding sequence.

A "promoter," as used herein, refers to a region of DNA that is capable of initiating transcription of an open reading frame or gene. Promoters are generally located in the 5'-region of, for example, an open reading frame, coding sequence, gene or operon, near or adjacent to a transcription initiation site. RNA polymerase and transcription factors can specifically bind to a promoter to initiate transcription. Promoters define the direction of transcription and indicate which DNA strand will be transcribed; this strand is known as the sense strand.

A promoter comprises at least a minimal sequence required to properly initiate transcription. A minimal nucleic acid molecule needed to initiate transcription is referred to as a "core promoter." A core promoter generally includes a transcription start site and element(s) directly upstream, a binding site for RNA polymerase, and general transcription factor binding site(s) (e.g., TATA box). A promoter may further comprise a proximal sequence ("proximal promoter") upstream of a gene (e.g., about 250 base pairs upstream of the transcription start site) containing primary regulatory elements, such as specific transcription factor binding site(s). A promoter may also comprise a distal sequence ("distal promoter") upstream of a gene containing additional regulatory element(s), which may have a weaker influence on transcription than a proximal promoter, such as sequences further upstream other than enhancer or other regulatory regions whose influence is positional/orientation independent, and specific transcription factor binding sites.

A non-naturally occurring nucleic acid molecule disclosed herein may comprise or consist essentially of only a core promoter, provided transcription can be initiated about 25% as well as a complete parent promoter containing the core promoter. Alternatively, non-naturally occurring nucleic acid molecule containing a core promoter may further comprise or consist essentially of a proximal promoter, a distal promoter, or both.

A region of DNA to which a transcription factor protein binds is referred to herein as an "operator." In certain embodiments, a transcription factor protein may bind to an operator and physically obstruct RNA polymerase from transcribing one or more genes. Such a transcription factor is referred to as a "repressor," which may be a de-repressible repressor or a co-repressor. For example, a repressor may normally bind to an operator and prevent transcription, but an inducer molecule can bind to the repressor protein to allow expression (i.e., induce or de-repress transcription). An exemplary de-repressible repressor is Lad, and its corresponding inducer can be allolactose or IPTG. Another exemplary de-repressible repressor is AraC, and its corresponding inducer can be arabinose. Alternatively, a repressor may not bind and repress transcription in the absence of a co-repressor, but will bind and repress transcription in the presence of a co-repressor. Exemplary co-repressors are TrpR and tryptophan. In further embodiments, a transcription factor may bind to an operator and activate, stimulate, or trigger RNA polymerase transcription of one or more genes. These transcription factors are referred to herein as an "activator" or an "activator protein," which may be an inducible activator or a repressible activator. For example, an inducible activator may not bind and activate transcription in the absence of an inducer. An exemplary inducible activator is BenR and its corresponding inducer can be a benzoate (e.g., sodium benzoate). Alternatively, an activator may normally bind to an operator and promote transcription, but an inhibitor molecule can bind to the activator protein to turn off transcription. An exemplary repressible activator is tetracycline controlled transactivator (tTA) and its inhibitor can be doxocycline.

In certain embodiments, an engineered expression regulatory nucleic acid molecule according to the present disclosure comprises a promoter and an operator. Exemplary operators include a trc operator (trp/lac operon hybrid), and operators from the lac operon, trp (tyrptophan) operon, ben (benzoate) operon, ara (arabinose) operon, tet (tetracycline) operon, or combinations thereof. In particular embodiments, an engineered expression regulatory nucleic acid molecule according to the present disclosure comprises a promoter and an operator that is bound by an activator. An exemplary operator that can be bound by an activator comprises an operator associated with a benzoate operon promoter.

A promoter that is "functional in a methanotrophic bacterium" is capable of initiating transcription of one or more open reading frames, coding sequences, genes, operons or the like, in a methanotrophic bacterium.

The term "methanotrophic bacterium" or "methanotroph" refers to a bacterium capable of metabolizing a C1 substrate as their only source of carbon and energy. Methanotrophic bacteria include "obligate methanotrophic bacteria" that can only utilize C1 substrates as carbon and energy sources and "facultative methanotrophic bacteria" that are able to use multi-carbon substrates, such as acetate, pyruvate, succinate, malate, or ethanol, in addition to C1 substrates, as their primary or sole carbon and energy sources.

"C1 substrate" refers to any carbon-containing molecule that lacks a carbon-carbon bond. Examples include methane, methanol, formaldehyde, formic acid, formate, methylated amines (e.g., mono-, di-, and tri-methyl amine), methylated thiols, and carbon dioxide.

Any promoter that is functional in methanotrophic bacteria may be included in any non-naturally occurring nucleic acid molecule provided herein. Examples of such promoters include a methanol dehydrogenase (MDH) promoter (e.g., the promoter portion of SEQ ID NO.:14 or 30), a 30S ribosomal protein S16 promoter (e.g., the promoter portion of SEQ ID NO.:15), a hexulose 6-phosphate synthase promoter (e.g., the promoter portion of SEQ ID NO.:16), a T5 promoter (e.g., the promoter portion of SEQ ID NO.:17), a Trc promoter (e.g., the promoter portion of SEQ ID NO.:18), a trfA promoter (e.g., the promoter portions of SEQ ID NOS.:4, 5 or 42), a β-lactamase promoter (e.g., the promoter portion of SEQ ID NO.:6) and a kanamycin resistance promoter (e.g., the promoter portions of SEQ ID NOS.:9 and 11).

An MDH promoter is a nucleic acid molecule capable of regulating or promoting expression of a subunit of MDH, e.g., a large subunit. The MDH promoter sequence may be from any methanotrophic bacterium (e.g., *Methylococcus capsulatus* Bath whose complete genome sequence is known; see Ward et al., *PLoS Biol.* 2:e303, 2004, Genbank accession number AE017282, *Methylosinus trichosporium*, and *Methylomonas* sp. 16a (ATCC No. PTA-2402, see, US Patent Application Publication No. 2006/0057726)) and may be from a species other than methanotrophic bacteria as long as it is functional in a methanotrophic bacterium. Exemplary MDH promoters include the promoter portion of SEQ ID NO.:14 (from *Methylococcus capsulatus* Bath) and the promoter portion of SEQ ID NO.:30 (moxF from *Methylomonas* 16a). In certain embodiments, a MDH promoter may be a further portion of the promoter portion of SEQ ID NO.:14 or 30, the further portion being capable of initiating the transcription of a downstream coding sequence (e.g., a MDH core promoter). Alternatively or additionally, an MDH promoter sequence is a polynucleotide having at least 80%, at least 85%, at least 90%, at least 91%, at least 92%, at least 93%, at least 94%, at least 95%, at least 96%, at least 97%, at least 98%, at least 99% or at least 100% identity to the promoter portion of SEQ ID NO.:14 or 30, provided the promoter can initiate transcription at least 50% as well as the parent promoter SEQ ID NO.:14 or 30, respectively. In certain embodiments, an engineered expression regulatory nucleic acid molecule comprises an MDH promoter and a non-MDH ribosomal binding sequence.

For determining sequence identity, the WU-BLAST-2 program (Altschul et al., Methods in Enzymology 266:460-480, 1996) is used. This program uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. A percent nucleic acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

A 30S ribosomal protein S16 promoter is a nucleic acid molecule capable of regulating or promoting the expression of a 30S ribosomal protein S16. A 30S ribosomal protein S16 promoter may be from any methanotrophic bacterium (e.g., *Methylococcus capsulatus* Bath, *Methylosinus trichosporium*, and *Methylomonas* sp. 16). Alternatively, it may be from a species other than methanotrophic bacteria as long as it is functional in a methanotrophic bacterium. An exemplary 30S ribosomal protein S16 promoter is the promoter portion of SEQ ID NO.:15. In certain embodiments, a 30S ribosomal protein S16 promoter may be a further portion of the promoter portion of SEQ ID NO.:15, the further portion being capable of initiating the transcription of a downstream coding sequence (e.g., a ribosomal protein S16 core promoter). Alternatively or additionally, a 30S ribosomal protein S16 promoter is a polynucleotide having at least 80%, at least 85%, at least 90%, at least 91%, at least 92%, at least 93%, at least 94%, at least 95%, at least 96%, at least 97%, at least 98%, at least 99% or at least 100% identity to the promoter portion of SEQ ID NO.:15, provided the promoter can initiate transcription at least 50% as well as the parent promoter of SEQ ID NO.:15. In certain embodiments, an engineered expression regulatory nucleic acid molecule comprises a 30S ribosomal protein S16 promoter and a non-30S ribosomal protein S16 ribosomal binding sequence.

A hexulose 6-phosphate synthase promoter is a nucleic acid molecule capable of regulating or promoting expression of a hexulose 6-phosphate synthase protein. The hexulose 6-phosphate synthase promoter sequence may be from any methanotrophic bacterium (e.g., *Methylococcus capsulatus* Bath, *Methylosinus trichosporium*, and *Methylomonas* sp. 16a, see, e.g., U.S. Pat. No. 7,098,005). Alternatively, it may be from a species other than methanotrophic bacteria as long as it is functional in a methanotrophic bacterium. An exemplary hexulose 6-phosphate synthase promoter sequence is the promoter portion of SEQ ID NO.:16. In certain embodiments, the hexulose 6-phosphate synthase promoter may be a further portion of the promoter portion of SEQ ID NO.:16, the further portion being capable of initiating the transcription of a downstream coding sequence (e.g., a hexulose 6-phosphate synthase core promoter). Alternatively or additionally, a hexulose 6-phosphate synthase promoter is a polynucleotide having at least 80%, at least 85%, at least 90%, at least 91%, at least 92%, at least 93%, at least 94%, at least 95%, at least 96%, at least 97%, at least 98%, at least 99% or at least 100% identity to the promoter portion of SEQ ID NO.:16, provided the promoter can initiate transcription at least 50% as well as the parent promoter of SEQ ID NO.:16. In certain embodiments, an engineered expression regulatory nucleic acid molecule comprises a hexulose 6-phosphate synthase promoter and a non-hexulose 6-phosphate synthase ribosomal binding sequence.

A T5 promoter is a promoter sequence derived from T5 bacteriophage (see, e.g., WO 2004/056975). An exemplary T5 promoter is the promoter portion of SEQ ID NO.:17. In certain embodiments, a T5 promoter may be a further portion of the promoter portion of SEQ ID NO.:17 (e.g., at least 30, 35, or 40 nucleotides in length) capable of initiating the transcription of a downstream coding sequence. Alternatively or additionally, a T5 promoter sequence is a polynucleotide having at least 80%, at least 85%, at least 90%, at least 91%, at least 92%, at least 93%, at least 94%, at least 95%, at least 96%, at least 97%, at least 98%, at least 99% or at least 100% identity to the promoter portion of SEQ ID NO.:17, provided the promoter can initiate transcription at least 50% as well as the parent promoter of SEQ ID NO.:17. In certain embodiments, an engineered expression regulatory nucleic acid molecule comprises a T5 promoter and a non-T5 ribosomal binding sequence.

A Trc promoter generally refers to a hybrid promoter containing the −35 region from the trpB promoter and the −10 region from the lacUV5 promoter for high level expression in *E. coli* (see, e.g., WO 2002/018617). An exemplary Trc promoter sequence is the promoter portion of SEQ ID NO.:18. In certain embodiments, a Trc promoter may be a further portion of the promoter portion of SEQ ID NO.:18 (e.g., at least 60, 65, 70, or 75 nucleotides in length), the further portion being capable of initiating the transcription of a downstream coding sequence. Alternatively or additionally, the Trc promoter sequence is a polynucleotide having at least 80%, at least 85%, at least 90%, at least 91%, at least 92%, at least 93%, at least 94%, at least 95%, at least 96%, at least 97%, at least 98%, at least 99% or at least 100% identity to SEQ ID NO.:18, provided the promoter can initiate transcription at least 50% as well as the parent promoter of SEQ ID NO.:18. In certain embodiments, an engineered expression regulatory nucleic acid molecule comprises an Trc promoter and a non-trp operon or non-lac operon ribosomal binding sequence.

A promoter in non-naturally occurring nucleic acid molecules provided herein may be a constitutive promoter or a regulated, repressible or inducible promoter.

A "constitutive promoter" is a nucleic acid molecule capable of initiation transcription of a gene in most cell types and at most times. Exemplary constitutive promoters that are functional in a methanotrophic bacterium and may be included in the non-naturally occurring nucleic acids provided herein include an MDH promoter, 30S ribosomal protein S16 promoter, hexulose 6-phosphate synthase promoter, or Trc promoter.

A "regulated promoter" or "repressible promoter" or "inducible promoter" is a nucleic acid molecule that is capable of promoting an increase or decrease of transcription in response to a specific stimulus. An inducible or repressible promoter may comprise an operator sequence to which an activator or a repressor may bind, respectively. For example, the binding of a repressor protein (e.g., LacI) to an operator can block or inhibit transcription from the associated promoter, but transcription may be induced by a molecule that associates with the repressor (e.g., IPTG) causing it to no longer bind the operator and thereby result in gene expression. Alternatively, an activator protein may not bind to an operator (e.g., BenR), but transcription may be activated in the presence of an inducer (e.g., sodium benzoate) since the association of the activator protein and inducer will promote binding to the operator and thereby result in gene expression.

Exemplary regulated promoters that may be included in the non-naturally occurring nucleic acid molecules provided herein include a promoter selected from a lac operon, a benzoate operon, a tetracycline promoter, a heat shock promoter, a metal-responsive promoter, a nitrate promoter, a light inducible promoter, and a ecdysone inducible promoter.

In addition to a promoter that is functional (i.e., promotes transcription) in a methanotropic bacterium, an engineered expression regulatory nucleic acid molecule may also comprise a native or a non-naturally occurring or engineered ribosomal binding sequence (RBS) to promote efficient translation. In certain embodiments, an engineered expression regulatory nucleic acid molecule comprises a native or a non-naturally occurring or engineered methanol dehydrogenase (MDH) RBS, provided that when the promoter is a native or wild-type MDH promoter, the RBS comprises a non-naturally occurring or engineered MDH ribosomal binding sequence or a non-MDH ribosomal binding sequence.

A "ribosomal binding sequence" or "ribosome binding sequence," as used herein, refers to a DNA molecule encoding a 5'-untranslated region ("5'-UTR") of an mRNA molecule, the region comprising a ribosomal binding site and optionally a spacer or a portion of a spacer, located between the ribosomal binding site and a start codon, as described herein. A ribosome binding site (also called the "Shine-Dalgarno sequence" or "SD sequence") is where the 30S ribosome small subunit binds first on mRNA and promotes efficient and accurate translation of mRNA. It is generally located a short distance upstream (e.g., three to 15 nucleotides, and typically between 6-8 nucleotides) of a start codon (e.g., AUG, CUG, GUG and UUG), and is generally purine-rich (A and G). For example, a common consensus sequence among many bacterial SD sequences is AGGAGG (SEQ ID NO.:53), which is usually located a few to about 10 nucleotides upstream of a start codon. The 3'-terminal end of the 16S rRNA in the 30S subunit has a complementary sequence that binds to the SD sequence and helps to properly position the ribosome on an mRNA to begin translation.

The nucleotides located between a ribosome binding site and a start codon on an mRNA is referred to herein as a "spacer." A spacer located between a ribosome binding site and a start codon for a nucleic acid molecule encoding a target polypeptide will range in length from three nucleotides to about 25 nucleotides. In certain embodiments, a spacer ranges in length from three to about 15 nucleotides, from four to about 12 nucleotides, from five to about 10 nucleotides, or a spacer contains six, seven, eight or nine nucleotides.

A "native MDH ribosome binding sequence" or "native MDH ribosomal binding sequence" refers to a naturally occurring MDH ribosomal binding sequence from a methanotrophic bacterium, which contains a nucleic acid molecule encoding a ribosomal binding site and optionally a nucleic acid molecule encoding a spacer or a portion of a spacer, wherein the spacer is located between the ribosomal binding site and start codon. Exemplary native MDH ribosomal binding sequences from *Methylococcus capsulatus* Bath (encoding spacers of various lengths) include TGGAGGAGACA (SEQ ID NO.:27), TGGAGGAGACAT (SEQ ID NO.:32), TGGAGGAGACAC (SEQ ID NO.:40), and TGGAGGAGACACA (SEQ ID NO.:41). A person of skill in the art will understand that an mRNA counterpart of these ribosome binding sequences will contain a U in place of a T in the ribosome binding site, spacer, or both.

An "altered MDH ribosome binding sequence" or "altered MDH ribosomal binding sequence" refers to an MDH ribosomal binding sequence engineered to have one or more nucleotides changed as compared to the unaltered or native MDH ribosomal binding sequence, provided that the encoded ribosomal binding site is capable of initiating translation and producing a detectable amount of product. In an altered MDH ribosomal binding sequence, nucleotides may be added, deleted, substituted, or any combination thereof, compared to a native MDH ribosomal binding sequence. The additions, deletions, substitutions, or combinations thereof may occur in a sequence encoding a ribosomal binding site, a sequence encoding a spacer, or both. In certain embodiments, a native MDH ribosomal binding sequence used to engineer an altered MDH ribosomal binding sequence is from an MDH from *Methylococcus capsulatus* Bath.

A "variant MDH ribosome binding site" refers to a ribosome binding site encoded in an altered MDH ribosomal binding sequence, wherein the RBS is engineered to have one or more nucleotide changes within the encoded ribosomal binding site as compared to the unaltered or native MDH ribosome binding sequence (e.g., SEQ ID NOS.:27, 32, 40 and 41 are native for MDH) nucleotides, such as at 1, 2, 3, 4, 5, 6, or more nucleotides, provided that the encoded ribosomal binding site is capable of initiating translation and producing a detectable amount of product. Exemplary altered MDH ribosomal binding sequences containing variant MDH ribosome binding sites include AAGGAGGTAAAAAA (SEQ ID NO.:20), ATGGTG-GAAAAAAA (SEQ ID NO.:22), ATGGATG-TAAAAAATAAAAAA (SEQ ID NO.:24), and ATTGTG-GTAAAAAATAAAAAA (SEQ ID NO.:26).

A "variant spacer" refers to a spacer encoded in an altered MDH ribosomal binding sequence, wherein the RBS is engineered to have one or more nucleotide changes within the encoded spacer as compared to the unaltered or native MDH ribosome binding sequence. In certain embodiments, a variant spacer may have a nucleotide addition, deletion, substitution, or any combination thereof. Therefore, a spacer may have a change in nucleotide sequence, a change in length, or both.

In certain embodiments, the length of an altered MDH ribosomal binding sequence may be the same as that of a native MDH ribosomal binding sequence. In further embodiments, an altered MDH ribosomal binding sequence may be shorter or longer than a native MDH ribosomal binding sequence. For example, an altered MDH ribosomal binding sequence may have a shortened or lengthened nucleic acid sequence encoding a ribosomal binding site, a shortened or lengthened nucleic acid sequence encoding a spacer, or both. In particular embodiments, an altered MDH ribosomal binding sequence (which may encode a native or variant ribosome binding site) may encode a spacer that ranges from three to about 6 to about 25 nucleotides in length, such as 3, 4, 5, 6, 7, 8, 9, 10, 11, 12, 13, 14, 15, 16, 17, 18, 19, 20, 21, 22, 23, 24 or 25 nucleotides long. In any of the aforementioned embodiments, an altered MDH ribosomal binding sequence may encode a variant spacer having one or more nucleotides changed from wild-type.

Exemplary native or altered MDH ribosomal binding sequences that encode native or variant spacers include SEQ ID NOS.:20, 22, 24, 26, 27, 32 and 41, or a portion thereof that is at least about 5 (e.g., at least 6, 7, 8, 9, or 10) up to about 15 nucleotides in length and is capable of initiating translation of mRNA such that protein product is detectable in methanotrophic bacteria by Coomassie blue staining or immunoblotting after separating by electrophoresis.

A native or altered MDH ribosomal binding sequence is typically or preferably functional (i.e., when transcribed into mRNA, capable of binding ribosome and initiating translation) in methanotrophic bacteria.

Different altered MDH ribosome binding sequences encoding native or variant spacers may encode mRNA molecules having different levels of activity when binding to ribosomes or in promoting translation of mRNAs, as described herein.

In a non-naturally occurring nucleic acid molecule provided herein, a native or altered MDH ribosome binding sequence may encode a native or variant spacer that is located downstream of a promoter and is functional in a methanotrophic bacterium. A promoter may be directly linked to a native or altered MDH ribosome binding sequence encoding a native or variant spacer. Alternatively, there may be a short distance or promoter spacer (e.g., 1 to about 10, 1 to about 15, 1 to about 20, 1 to about 25, 1 to about 30, 1 to about 35, 1 to about 40, 1 to about 45, 1 to about 50, 1 to about 75, or 1 to about 100 nucleotides) between the promoter and the native or altered MDH ribosome binding sequence.

Exemplary non-naturally occurring nucleic acid molecules include those comprising SEQ ID NOS.:19, 21, 23 and 25 in which an MDH promoter is linked to different altered MDH ribosome binding sequences encoding variant spacers as compared to native (SEQ ID NOS.:20, 22, 24, and 26), and SEQ ID NOS.:28-30, 43 and 44 in which 30S ribosomal protein S16, hexulose 6-phosphate synthase, moxF, 30S ribosomal protein S12, and 50S ribosomal protein L13 promoters are linked to a native MDH ribosome binding sequence encoding a native spacer, SEQ ID NO.:40, respectively.

In a related aspect, the present disclosure provides a non-naturally occurring nucleic acid molecule that comprises: (1) a promoter selected from an MDH promoter, 30S ribosomal protein S16 promoter, hexulose 6-phosphate synthase promoter, T5 promoter, and Trc promoter, and (2) a ribosome binding sequence that is functional in a methanotrophic bacterium, provided that if the promoter and the ribosome binding sequence are from the same gene, then at least one of the sequences are not native or wild-type (i.e., naturally occurring)—that is, are engineered to be different from native. For example, when the promoter and ribosome binding sequence are from the same MDH gene, then (a) if the promoter is a native MDH promoter, then the ribosome binding sequence is not a native MDH ribosome binding sequence, or (b) if the promoter is not a native MDH promoter, then the ribosome binding sequence may be native or non-native.

In any of the aforementioned embodiments, a ribosome binding sequence may be any ribosome binding sequence that is functional in a methanotrophic bacterium, including a native or altered MDH ribosome binding sequence that encode a native or variant ribosome binding site, spacer, or both, as provided herein. In any of the aforementioned embodiments, a ribosome binding sequence is located downstream of a promoter and may be directly linked to the promoter or indirectly linked to the promoter via a short nucleotide fragment or promoter spacer (e.g., from 1 to about 10, 1 to about 15, 1 to about 20, 1 to about 25, 1 to about 30, 1 to about 35, 1 to about 40, 1 to about 45, 1 to about 50, 1 to about 55, 1 to about 60, 1 to about 65, 1 to about 70, 1 to about 75, 1 to about 80, 1 to about 85, 1 to about 90, 1 to about 95, or 1 to about 100 nucleotides in length).

B. Expression Cassettes

The present disclosure further provides expression cassettes for making target polypeptides. Such an expression cassette comprises any of the expression regulatory nucleic acid molecules provided herein operably linked to a nucleic acid molecule encoding a target polypeptide. Because the expression regulatory nucleic acid molecules provided herein are not naturally occurring, the expression cassettes comprising such nucleic acids are also not naturally occurring (i.e., engineered).

A nucleic acid molecule encoding a target polypeptide is "operably linked" to an expression regulatory nucleic acid molecule when the expression regulatory nucleic acid molecule is capable of promoting or regulating expression of a target polypeptide.

A nucleic acid molecule encoding a target polypeptide may be directly linked to the 3'-terminus of a ribosomal binding sequence encoding a ribosomal binding site (e.g., a native or variant MDH ribosome binding site) so that the target polypeptide start codon is located directly downstream of the native or modified MDH ribosome binding site. Thus, an expression cassette provided herein comprises, in the 5' to 3' direction, a promoter that is functional in a methanotrophic bacterium, an MDH ribosomal binding sequence (e.g., encoding a native or variant MDH ribosome binding site, spacer or both), and a nucleic acid molecule encoding a target polypeptide.

Alternatively, a sequence encoding a target polypeptide may be linked to the 3'-terminus of a ribosomal binding sequence encoding a ribosomal binding site and a spacer, wherein the spacer is disposed between the ribosome binding site (e.g., native or variant) and the target polypeptide start codon, wherein the spacer ranges in length from one nucleotide to about 25 nucleotides (e.g., 1 to about 10, 1 to about 20, 1 to about 25, about 3 to about 15, about 5 to about 12, or about 6 to about 8 nucleotides in length, not including the ribosome binding site).

In certain embodiments, an expression cassette comprises an expression regulatory nucleic acid molecule containing an engineered constitutive promoter that is functional in methanotrophic bacteria so that a target polypeptide is constitutively produced in the methanotrophic bacteria. An exemplary engineered constitutive promoter comprises a 30S ribosomal protein S16 promoter linked to an MDH ribosome binding sequence (native or altered) encoding a spacer of about 5 to about 8 nucleotides in length before the start codon for a nucleic acid molecule encoding a target polypeptide.

In further embodiments, an expression cassette comprises an expression regulatory nucleic acid molecule containing an inducible promoter that is functional in methanotrophic bacteria so that a target polypeptide is inducibly produced in the methanotrophic bacteria. An inducible promoter may be naturally occurring, such as a $P_{ben}$ inducible promoter operably linked to a nucleic acid molecule encoding a target polypeptide. Alternatively, an inducible promoter may be a recombinant or engineered inducible promoter that does not exist in nature. For example, an inducible promoter may comprise a constitutive promoter combined with an operator from a different promoter to convert the normally constitutive promoter into an inducible promoter. Examples of such chimeric promoter-operator constructs include an MDH promoter linked to an operator of the lac operon, or an MDH promoter sequence flanked by two or more operator sequences of the lac operon wherein the two operator sequences may or may not be the same (see, e.g., FIG. 2).

Such natural or engineered inducible promoters (operably linked to a nucleic acid molecule encoding a target polypeptide of interest in a first expression regulatory nucleic acid molecule) may be used in combination with a second expression regulatory nucleic acid molecule that, for example, enables or promotes constitutive expression of a repressor or activator protein. In certain embodiments, a second nucleic acid molecule comprises a constitutive promoter that is the same as the constitutive promoter as used to engineer the inducible promoter (e.g., MDH promoter). Alternatively, a second nucleic acid molecule may comprise a constitutive promoter that is different from the constitutive promoter used to engineer the inducible promoter (e.g., use a 30S ribosomal protein S16 promoter for the second nucleic acid molecule and use a MDH promoter to generate an engineered inducible promoter). In still further embodiments, a second expression regulatory nucleic acid molecule that controls or promotes regulated (inducible or repressible) expression of a repressor or activator protein specific for the first expression regulatory nucleic acid molecule operably linked to a nucleic acid molecule encoding a target polypeptide of interest.

In further embodiments, a second expression regulatory nucleic acid molecule may comprise a native or altered MDH ribosomal binding sequence. In such a case, a native or altered MDH ribosomal binding sequence may be the same as or different from the native or altered MDH ribosomal binding sequence used in the engineered inducible promoter that regulates expression of a target polypeptide. In certain embodiments, a second expression regulatory nucleic acid sequence may comprise a non-native ribosomal binding sequence, such as a benA ribosomal binding sequence of the benzoate operon.

In certain embodiments, a first expression regulatory nucleic acid molecule operably linked to a nucleic acid molecule encoding a target polypeptide and a second expression regulatory nucleic acid molecule can form a single nucleic acid molecule (e.g., carried on a single vector). Alternatively, these two nucleic acid molecules may be present as separate nucleic acid molecules (e.g., on separate vectors) In still another embodiment, such nucleic acid molecules may be integrated into a host chromosome at a single site, at separate sites or one or both may be integrated at multiple sites.

A nucleic acid molecule encoding a target polypeptide can encode any polypeptide of interest to be expressed using any of the expression regulatory nucleic acid molecules or expression cassettes of this disclosure in a methanotrophic bacterium. Exemplary target polypeptides include reporter proteins, such as green fluorescent protein (GFP); proteins that enable increased production of desired chemicals or metabolites (e.g., an amino acid biosynthesis enzyme (such as lysine biosynthesis enzymes, threonine biosynthesis enzymes, methionine biosynthesis enzymes, cysteine biosynthesis enzymes), isoprene synthase, crotonase, crotonyl CoA thioesterase, 4-oxalocrotonate decarboxylase, fatty acid converting enzymes (such as fatty acyl-CoA reductase, a fatty alcohol forming acyl-ACP reductase, a carboxylic acid reductase), fatty acid elongation pathway enzymes (such as β-ketoacyl-CoA synthase, a β-ketoacy-CoA reductase, a β-hydroxy acyl-CoA dehydratase, an enoyl-CoA reductase), carbohydrate biosynthesis enzyme (such as glucan synthase) and lactate dehydrogenase; and antibiotic resistance proteins.

As used herein, metabolites refer to intermediates and products of metabolism, including primary metabolites (compound directly involved in normal growth, development, and reproduction of an organism or cell) and secondary metabolites (organic compounds not directly involved in normal growth, development, or reproduction of an organism or cell but have important ecological function). Examples of metabolites that may be produced using the constructs described herein include alcohols, amino acids, nucleotides, antioxidants, organic acids, polyols, antibiotics, pigments, sugars, vitamins or any combination thereof. Desired chemicals or metabolites include, for example, isoprene, lactate, and amino acids (e.g., L-lysine, L-valine, L-tryptophan, and L-methionine). Host cells containing such recombinant polynucleotides are useful for the production of desired products (e.g., amino acids, fatty acids, lactate, isoprene, propylene), as described herein.

Depending upon the desired level of production (whether constitutive or induced), an appropriate native or altered MDH ribosome binding sequence may be selected. When overexpression of a target protein is desirable, a native or altered MDH ribosome binding sequence having a high efficiency in facilitating translation may be used. For example, a native MDH ribosome binding sequence from *Methylococcus capsulatus* Bath (SEQ ID NO.:27) can be used in combination with a hexulose 6-phosphate synthase promoter to increase the production of a target polypeptide of interest. In another example, a native MDH ribosome binding sequence from *Methylococcus capsulatus* Bath can be used in combination with a methanol dehydrogenase, large subunit (moxF) promoter from *Methylomonas* 16a to increase the production of a target polypeptide of interest, which was not observed previously.

On the other hand, if limited or reduced level of expression of a target protein is desired, a less efficient MDH ribosome binding sequence may be used. Examples of such RBSs include SEQ ID NOS.:20, 22, 24, 26, or combinations thereof.

In any of the aforementioned embodiments, a target polypeptide may be produced by introducing an agent that binds to a repressor and inhibits the binding of the repressor to the operator sequence of the inducible promoter that regulates the production of the target polypeptide.

The repressor may be a naturally occurring repressor. Alternatively, it may be a modified repressor that is not naturally occurring. The modified repressor may have enhanced repressor activity compared to the wild type native repressor.

In certain embodiments, the present disclosure provides a non-naturally occurring expression regulatory nucleic acid or expression cassette that comprises: (A) (1) an inducible promoter and an operator (e.g., of the lac or ben operon), both of which are functional in methanotrophic bacteria, (2) a ribosomal binding sequence (e.g., a native or altered MDH ribosomal binding sequence), (3) a nucleic acid molecule encoding a target protein (e.g., a marker such as GFP, a metabolic enzyme), wherein the nucleic acid molecule encoding the target protein (3) is operably linked to inducible promoter (1) and ribosomal binding sequence (2); (B) (4) a constitutive promoter that is functional in methanotrophic bacteria, (5) a ribosomal binding sequence (e.g., a native or altered MDH ribosomal binding sequence), and (6) a nucleic acid molecule encoding a repressor or inducer protein (e.g., LacI or BenR protein), wherein the nucleic acid molecule encoding the repressor or inducer protein (6) is operably linked to constitutive promoter (4) and ribosomal binding sequence (5); or (C) both (A) and (B).

Exemplary non-naturally occurring expression regulatory nucleic acids or expression cassettes comprise: (A) (1) an MDH promoter (e.g., SEQ ID NO.:36) flanked by two or more operator sequences of the lac operon (e.g., SEQ ID NOS.:35 and 37), (2) an MDH ribosomal binding sequence (e.g., SEQ ID NO.:41), and (3) a nucleic acid molecule encoding a target polypeptide (e.g., GFP, metabolic enzyme), wherein the nucleic acid molecule encoding the target polypeptide (3) is operably linked to inducible promoter (1) and RBS (2); or (B) (4) a 30S ribosomal protein S16 promoter (e.g., the promoter portion of SEQ ID NO.: 28), (5) an MDH ribosomal binding sequence encoding a variant spacer (e.g., SEQ ID NO.:32), and (6) a nucleic acid molecule encoding a repressor or activator protein (e.g., SEQ ID NO.:33, which encodes a variant LacI, SEQ ID NO.:39, which encodes a wild type LadI; SEQ ID NO.:46 or 47, which encodes BenR), wherein the nucleic acid molecule encoding the repressor or activator protein is operably linked to constitutive promoter (4) and RBS (5); or (C) both (A) and (B). A specific example of an engineered expression regulatory nucleic acid molecule containing a nucleic acid molecule encoding a target polypeptide (in this case GFP, but the target may be any polypeptide, such as a metabolic enzyme) (3) operably linked to an inducible promoter (1) and an RBS (2) is set forth in the polynucleotide of SEQ ID NO.:34. A specific example of an engineered expression regulatory nucleic acid molecule containing a nucleic acid molecule encoding a repressor protein (in this case Lad) (6) operably linked to a constitutive promoter (4) and an RBS (5) is set forth in the polynucleotide of SEQ ID NO.:31. In certain embodiments, any such engineered expression regulatory nucleic acid molecules are present in the same vector, are present in separate vectors, are integrated into the genome, or any combination thereof.

A schematic representation of an exemplary non-naturally occurring nucleic acid comprising an MDH promoter flanked by lac operon operator sequences operably linked to a nucleic acid molecule encoding a target polypeptide is shown in FIG. 2.

In some embodiments, a target polypeptide may be produced by introducing an agent that binds to or associates with an activator and promotes the binding of activator to the inducible promoter that regulates the production of a target polypeptide. An activator may be a naturally occurring activator. Alternatively, it may be a modified activator that is not naturally occurring. A modified activator may have enhanced activator activity compared to a wild type native activator.

Further exemplary non-naturally occurring expression regulatory nucleic acids or expression cassettes comprise: (A) (1) an inducible promoter (e.g., promoter region with ribosome binding site of a benzoate metabolic operon) that is functional in methanotrophic bacteria; (2) a ribosomal binding sequence (e.g., a benA RBS); (3) a nucleic acid molecule encoding a target polypeptide (e.g., marker, metabolic enzyme), wherein the nucleic acid encoding the target polypeptide (3) is operably linked to the inducible promoter (1) and the first ribosomal binding sequence (2); or (B) (4) a constitutive promoter that is functional in methanotrophic bacteria, (5) a ribosomal binding sequence (e.g., a native or altered MDH ribosomal binding sequence), and (6) a nucleic acid molecule encoding an activator protein (e.g., BenR), wherein the nucleic acid molecule encoding the activator protein (6) is operably linked to the constitutive promoter (4) and the ribosomal binding sequence (5); or (C) both (A) and (B).

Exemplary non-naturally occurring expression regulatory nucleic acids or expression cassettes comprise (1) a 30S ribosomal protein S16 promoter (e.g., SEQ ID NO.:15), (2) an MDH ribosomal binding sequence encoding a variant spacer (e.g., SEQ ID NO.:41), and (3) a nucleic acid molecule encoding activator protein BenR (e.g., SEQ ID NO.:46 or 47), wherein the nucleic acid molecule encoding the activator protein BenR is operably linked to constitutive promoter (1) and RBS (2); (4) a $P_{ben}$ promoter sequence (e.g., SEQ ID NO.:48); (5) a benA ribosomal binding sequence (e.g., SEQ ID NO.:54); and (6) a nucleic acid molecule encoding an activator protein, operably linked to promoter (4) and RBS (5).

Figure 8:
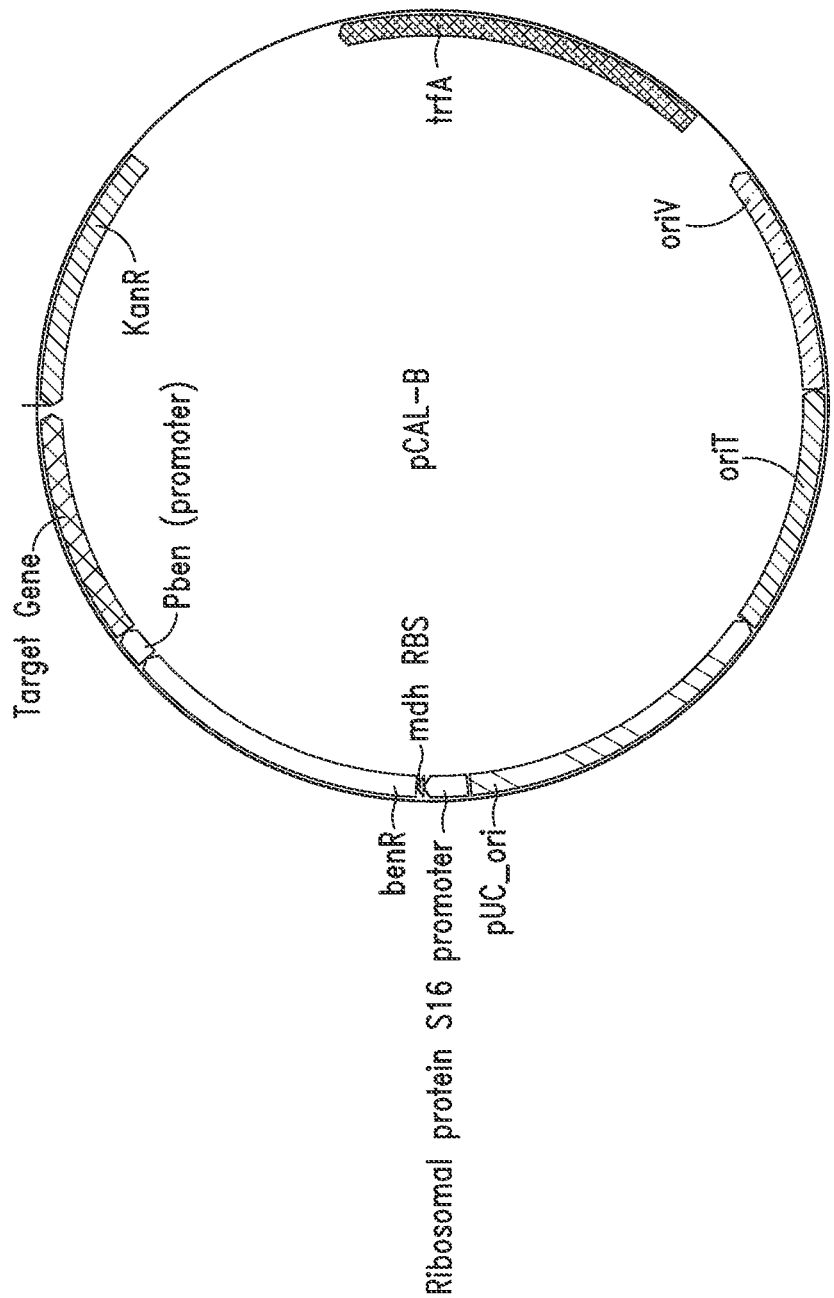
FIG. 8 is a schematic map of an exemplary vector (pCAL-B) containing a sodium benzoate inducible expression system for methanotrophic bacteria.

A schematic representation of an exemplary non-naturally occurring expression regulatory nucleic acid comprising a $P_{ben}$ promoter sequence operably linked to a nucleic acid sequence encoding a target polypeptide, and comprising a 30S ribosomal protein S16 promoter operably linked to a nucleic acid encoding BenR is shown in FIG. 8.

Figure 12:
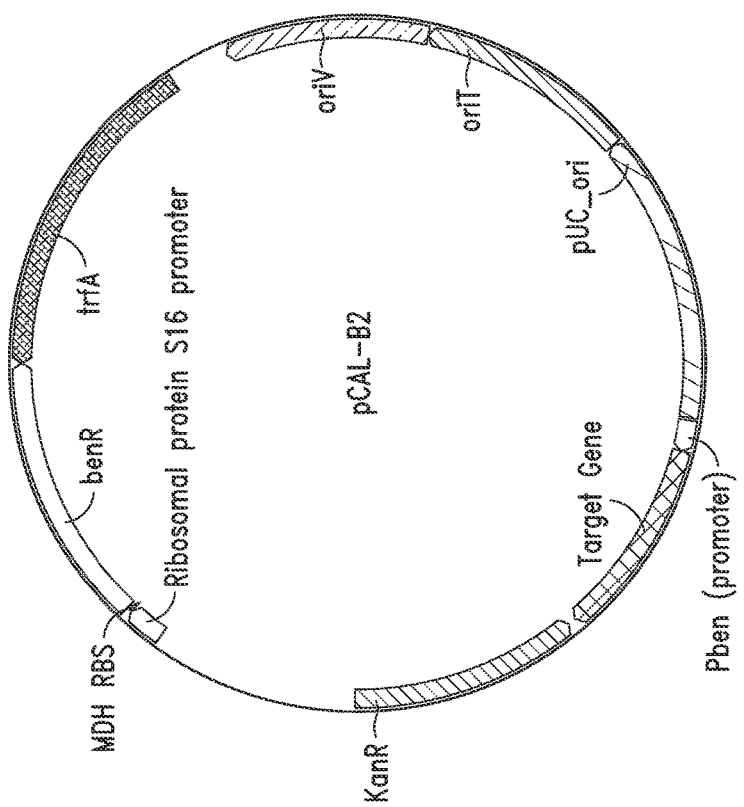
FIG. 12 is a schematic map of an alternative exemplary vector (pCAL-B2) containing a sodium benzoate inducible expression system for methanotrophic bacteria.

Schematic representations of exemplary non-naturally occurring expression regulatory nucleic acids comprising a $P_{ben}$ promoter sequence operably linked to a nucleic acid molecule encoding a target polypeptide, or comprising a 30S ribosomal protein S16 promoter sequence operably linked to a nucleic acid encoding BenR are shown in two different configurations with vector pCAL in FIGS. 8 and 12.

C. Expression Vectors

The present disclosure also provides an expression vector (pCAL) that can comprise a non-naturally occurring expression regulatory nucleic acid or expression cassette as provided herein.

The term "vector" refers to a DNA molecule used as a vehicle to carry foreign genetic material extrachromosomally or aid in transferring such material into another cell or aid in integrating into a host cell chromosome. In any of these embodiments, a vector can be self-replicating or replicated as part of a chromosome or optionally express any nucleic acid molecule of interest inserted into or carried on the vector. In certain embodiments, a vector is a plasmid.

Plasmids are double-stranded generally circular DNA sequences that are capable of automatically replicating in a host cell. Plasmid vectors contain an origin of replication that allows for semi-independent replication of the plasmid in the host and also for transgene insertion. Plasmids may have many more features, including a "multiple cloning site" (MCS) that includes multiple restriction sites for insertion of a nucleic acid molecule of interest (e.g., encoding a target polypeptide, such as a metabolic enzyme).

Vectors as provided herein may contain a non-naturally occurring expression regulatory nucleic acid that comprises: (1) a promoter sequence that is functional in methanotrophic bacteria, and (2) a ribosomal binding sequence (e.g., a native or altered MDH ribosomal binding sequence). Such vectors may further comprise a multiple cloning site (MCS) to facilitate the insertion of a target protein-encoding nucleic acid molecule. In certain embodiments, a vector as provided herein may comprise an expression cassette that includes a nucleic acid molecule encoding a target polypeptide operably linked to non-naturally occurring expression regulatory nucleic acids to be regulated by such nucleic acids.

The vectors preferably comprise an origin of replication functional in methanotrophic bacteria so that the vectors can replicate in the methanotrophic bacteria. In certain embodiments, they may further comprise another origin of replication that is functional in another bacterium (e.g., *E. coli*).

Vectors particularly useful in genetic manipulation of methanotrophic bacteria are described in detail herein. However, vectors that comprise the non-naturally occurring expression regulatory nucleic acids or expression cassettes according to the present disclosure are not limited to those preferred vectors.

D. Host Cells

The present disclosure also provides host cells that comprise expression regulatory nucleic acids or expression cassettes provided herein. The expression regulatory nucleic acids or expression cassettes may be integrated into the genomes of the host cells by any method known in the art (see, e.g., US Patent Application Publication No. 2006/0057726). Alternatively, they may be present in one or more copies of vectors transformed into the host cells.

The term "host" refers to a microorganism (e.g., methanotrophic bacteria) that may be genetically modified, for example, by transformation.

Transformation refers to the transfer of a nucleic acid (e.g., exogenous nucleic acid) into the host microorganism.

Preferably, the host cells are methanotrophic bacteria. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway.

Methanotrophic bacteria are grouped into several genera: *Methylomonas, Methylobacter, Methylococcus, Methylocystis, Methylosinus, Methylomicrobium, Methanomonas,* and *Methylocella*.

Methanotrophic bacteria include obligate methanotrophs and facultative methanotrophs. Facultative methanotrophs include some species of *Methylocella, Methylocystis,* and *Methylocapsa* (e.g., *Methylocella silvestris, Methylocella palustris, Methylocella tundrae, Methylocystis daltona* strain SB2, *Methylocystis bryophila, Methylocapsa aurea* KYG), and *Methylobacterium organophilum* (ATCC 27,886).

Exemplary methanotrophic bacteria species include: *Methylococcus capsulatus* Bath strain, *Methylomonas* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylacidiphilum fumariolicum, Methyloacida kamchatkensis, Methylibium petroleiphilum,* and *Methylomicrobium alcaliphilum*.

Preferably, the host cell is a *methylococcus* (e.g., *Methylococcus capsulatus*, including the strain *Methylococcus capsulatus* Bath) or *Methylosinus* (e.g., *Methlosinus trichosporium*, including the strain *Methlosinus trichosporium* OB3b).

Methanotrophic bacteria may be transformed using methods known in the art. For example, electroporation of C1 metabolizing bacteria has been previously described in Toyama et al., 1998, FEMS Microbiol. Lett. 166:1-7 (*Methylobacterium extorquens*); Kim and Wood, 1997, Appl. Microbiol. Biotechnol. 48:105-108 (*Methylophilus methylotrophus* AS1); Yoshida et al., 2001, Biotechnol. Lett. 23:787-791 (*Methylobacillus* sp. strain 12S), and US2008/0026005 (*Methylobacterium extorquens*).

Bacterial conjugation, which refers to a particular type of transformation involving direct contact of donor and recipient cells, is more frequently used for the transfer of nucleic acids into methanotrophic bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acids into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilizable plasmid. The physical transfer of the donor plasmid can occur through a self-transmissible plasmid or with the assistance of a "helper" plasmid. Conjugations involving C1 metabolizing bacteria, including methanotrophic bacteria, have been previously described in Stolyar et al., 1995, Mikrobiologiya 64:686-691; Martin and Murrell, 1995, FEMS Microbiol. Lett. 127:243-248; Motoyama et al., 1994, Appl. Micro. Biotech. 42:67-72; Lloyd et al., 1999, Archives of Microbiology 171:364-370; and Odom et al., PCT Publication WO 02/18617; Ali et al., 2006, Microbiol. 152:2931-2942.

The host cells provided herein may be bacteria other than methanotrophic bacteria. For example, a vector in which the expression regulatory nucleic acid or expression cassette is present may comprise an origin of replication functional in bacteria other than methanotrophic bacteria, such as E. coli. Such a vector may be transformed into the other bacteria to facilitate cloning or other genetic manipulation.

E. Methods for Expressing Target Proteins

In certain aspects, the present disclosure also provides methods for producing a target polypeptide. In some embodiments, a method comprises culturing a host cell that comprises an expression regulatory nucleic acid provided herein operably linked to a nucleic acid molecule encoding a target polypeptide to produce the target polypeptide.

Culturing host cells to make target polypeptides is generally known. In cases where the expression regulatory nucleic acid comprises an inducible promoter sequence, host cells are cultured under conditions that induce expression of target polypeptide-encoding nucleic acid sequences. For example, where the expression regulatory nucleic acid comprises an operator sequence of the lac operon, isopropyl-β-D-thio-galactoside (IPTG) may be added to culture medium for the host cells to induce the production of the target polypeptide controlled by the expression regulatory nucleic acid. In some embodiments, where the expression regulatory nucleic acid comprises a benR gene of the benzoate operon, sodium benzoate may be added to culture medium to induce the production of the target polypeptide controlled by an expression regulatory nucleic acid. Benzoic acid and benzoic acid analogs may also induce production of the target polypeptide controlled by the benR gene.

The methods for producing target polypeptide may further comprise purifying the target polypeptide produced by the host cells. Suitable purification methods are known in the art and may be used.

II. Genetic Manipulation of Methanotrophic Bacteria

In still another aspect, the present disclosure provides vectors useful in genetic manipulation of methanotrophic bacteria, host cells comprising such vectors, and methods for using such vectors, such as in producing polypeptides of interest.

The present disclosure provides a vector that comprises: (1) a beta-lactamase (bla) or neomycin phosphotransferase promoter sequence operably linked to a sequence encoding a TrfA protein, and (2) an origin of vegetative replication (oriV) that is functional in a methanotrophic bacterium. An exemplary vector of this disclosure is pCAL, which is depicted in FIG. 1A.

A β-lactamase promoter ("Pbla") is a promoter found in β-lactamase expression cassette that enables expression of a β-lactamase under appropriate conditions. An exemplary Pbla is the promoter portion of SEQ ID NO.:6. In certain embodiments, a Pbla is a further portion of the promoter portion of SEQ ID NO.:6, the further portion being capable of initiating the transcription of a trfA gene. In certain embodiments, a Pbla is a polynucleotide having at least 80%, at least 85%, at least 90%, at least 91%, at least 92%, at least 93%, at least 94%, at least 95%, at least 96%, at least 97%, at least 98%, at least 99% or at least 100% identity with the promoter portion of SEQ ID NO.:6, provided the promoter can initiate transcription at least 50% as well as the parent promoter of SEQ ID NO.:6.

A neomycin phosphotransferase promoter sequence (Pneo) is a promoter sequence derived from a neomycin phosphotransferase expression cassette that enables expression of a neomycin phosphotransferase under appropriate conditions. An exemplary Pneo is the promoter portion of SEQ ID NO.:7. In certain embodiments, the Pneo is a further portion of the promoter portion of SEQ ID NO.:7 capable of initiating the transcription of a trfA gene. In certain embodiment, the Pneo is a nucleotide sequence that is at least 80%, at least 85%, 90%, at least 91%, at least 92%, at least 93%, at least 94%, at least 95%, at least 96%, at least 97%, 98%, at least 99% or at least 100% identity with the promoter portion of SEQ ID NO.:7, provided the promoter can initiate transcription at least 50% as well as the parent promoter of SEQ ID NO.:7.

TrfA is a replication initiation protein that binds to activate an origin of vegetative replication, oriV, to initiate vegetative replication from oriV. In certain embodiments, a TrfA protein is encoded by a nucleic acid coding sequence found on the RK2 plasmid (see, e.g., National Center for Biotechnology Information: "*Escherichia coli* W plasmid pRK2, complete sequence, www.ncbi.nlm.nih.gov/nuccore/ 315063834; Stepanek et al., Plasmid 54:86-91, 2005; Thomas et al., J. Bacteriol. 172:3859-67, 1990). Exemplary TrfA proteins include those mutated TrfA that increase plasmid copy number, as described in, for example, Ross et al., J. Bacteriol. 174:4110-9, 1992.

An exemplary sequence encoding a TrfA protein is set forth in SEQ ID NO.:3. In certain embodiments, a TrfA protein encoding nucleic acid molecule has at least 80%, at least 85%, at least 90%, at least 91%, at least 92%, at least 93%, at least 94%, at least 95%, at least 96%, at least 97%, at least 98%, at least 99% or at least 100% identity with SEQ ID NO.:3, provided the TrFA protein can promote vegetative replication at least 50% as well as the parent SEQ ID NO.:3. The amino acid sequence similarity, as described herein, is determined using the MegAlign program by DNASTAR using a method among those available to the program that produces the highest similarity.

The present inventors discovered that having a TrfA gene under the control of a Pbla or Pneo improved the transformation efficiency of the resulting vector into methanotrophic bacteria (e.g., a higher number of colonies per transformation plate).

An "origin of vegetative replication (oriV)" refers to a DNA sequence from which vegetative replication of a plasmid originates.

During bacterial conjugation, one strand of a conjugative plasmid in a donor bacterium is nicked at the oriT. The nicked strand, or T-strand, is then unwound from the unbroken strand and transferred to the recipient cell in a 5'-terminus to 3'-terminus direction. The remaining strand is replicated either independent of conjugative action or in concert with conjugation. The replication of the remaining strand independent of conjugative action is referred to as "vegetative replication," while the replication of the remaining strand in concert with conjugation is referred to as "conjugative replication."

Exemplary oriV sequences include naturally occurring oriV sequences (e.g., oriV from the RK2 plasmid) or modified oriV sequences. An exemplary modified oriV sequence is set forth in SEQ ID NO.:1. In certain embodiments, an oriV sequence is significantly shorter than or a truncated version of an oriV sequence typically used (see, e.g., SEQ ID NO.:2). For example, SEQ ID NO.:1 is significantly shorter than the oriV sequence from the RK2 plasmid typically used in the art, but still is capable of initiating vegetative replication. In fact, SEQ ID NO.:1 surprisingly increased transformation efficiency of vectors comprising such a sequence and a higher yield of plasmid DNA isolated from transformed bacteria.

In certain embodiments, an oriV is a polynucleotide having at least 80%, at least 85%, at least 90%, at least 91%, at least 92%, at least 93%, at least 94%, at least 95%, at least 96%, at least 97%, at least 98%, at least 99% or at least 100% identity to SEQ ID NO.:1 or SEQ ID NO.:2, provided that vegetative replication is promoted at least 50% as well as the parent SEQ ID NO.:2.

Vectors provided herein may further comprise (3) an origin of transfer (oriT). An "origin of transfer (oriT)" is a sequence of DNA necessary for transfer of a bacterial plasmid from a bacterial host to recipient during bacterial conjugation. The oriT is cis-acting
   it is found on the same plasmid that is being transferred, and is transferred along with the plasmid. The oriT consists of three functionally defined domains: a nicking domain, a transfer domain, and a termination domain. Preferably, an oriT is functional in a methanotrophic bacterium.

Exemplary oriT sequences include naturally occurring oriT sequences (e.g., oriT from the RK2 plasmid) or modified oriT sequences. An exemplary modified oriT is set forth in SEQ ID NO.:8, which is significantly shorter than an oriT sequence typically used. In certain embodiments, an oriT is a nucleotide having at least 80%, at least 85%, at least 90%, at least 91%, at least 92%, at least 93%, at least 94%, at least 95%, at least 96%, at least 97%, at least 98%, at least 99% or at least 100% identity to SEQ ID NO.:8, provided transfer is promoted at least 50% as well as the parent SEQ ID NO.:8.

Vectors provided herein may further comprise (4) a kanamycin resistance cassette. The presence of such a cassette facilitates selection of transformants that comprise such a vector.

A "kanamycin resistance cassette" refers to a nucleic acid molecule cassette that encodes a kanamycin resistance protein. A kanamycin resistance cassette can comprise a nucleic acid molecule (e.g., nptII and nptIII) encoding a kanamycin resistance protein and a promoter sequence that enables the expression of the kanamycin resistance protein in a host cell.

Exemplary promoter sequences of kanamycin resistance cassettes include the promoter sequence of RK2 plasmid (e.g., the promoter portion of SEQ ID NO.:11) and the promoter sequence (e.g., the promoter portion of SEQ ID NO.:9). In certain embodiments, a kanamycin promoter is a polynucleotide having at least at least 80%, at least 85%, at least 90%, at least 91%, at least 92%, at least 93%, at least 94%, at least 95%, at least 96%, at least 97%, at least 98%, at least 99% or at least 100% identity with the promoter portion of SEQ ID NO.:11 or 9, provided the promoter can initiate transcription at least 50% as well as the parent promoter of SEQ ID NO.:11 or 9.

Exemplary nucleic acid sequences encoding kanamycin resistance proteins in the cassettes include the kanamycin resistance protein-encoding sequence from RK2 plasmid as set forth in SEQ ID NO.:12 and the nucleotide sequence as set forth in SEQ ID NO.:10. In certain embodiments, a kanamycin resistance protein-encoding polynucleotide has at least 80%, at least 85%, at least 90%, at least 91%, at least 92%, at least 93%, at least 94%, at least 95%, at least 96%, at least 97%, at least 98%, at least 99%, or at least 100% identity with SEQ ID NO.:12 or 10, provided the kanamycin resistance protein promotes resistance to kanamycin as well as the parent SEQ ID NO.:12 or 10.

Vectors provided herein may further comprise (5) a second origin of replication that is functional in a second bacterium other than a methanotrophic bacterium, wherein the second origin of replication is different from an oriV if present in the vector.

The second bacterium may be any bacterium other than a methanotrophic bacterium. Preferably, a second bacterium is a bacterium well studied and commonly used to facilitate cloning and replication or other genetic manipulation of the vectors, such as E. coli.

Any origin of replication functional in the second bacterium may be used. Preferably, a pUC origin of replication (SEQ ID NO.:13) is used for the ease of cloning in E. coli. In certain embodiments, an origin of replication is a nucleotide sequence that is at least 80%, at least 85%, at least 90%, at least 91%, at least 92%, at least 93%, at least 94%, at least 95%, at least 96%, at least 97%, at least 98%, at least 99%, or at least 100% identity with SEQ ID NO.:13, provided that replication is promoted at least 50% as well as the parent SEQ ID NO.:13.

Above-described components (3) to (5), especially components (3) and (5), are optional components of the vectors provided herein and are not required. In certain embodiments, in addition to components (1) and (2), the vectors comprise only one of components (3) to (5). In certain other embodiments, the vectors comprise two of components. In yet other embodiments, the vectors comprise all three of components (3) to (5).

Figure 1B:
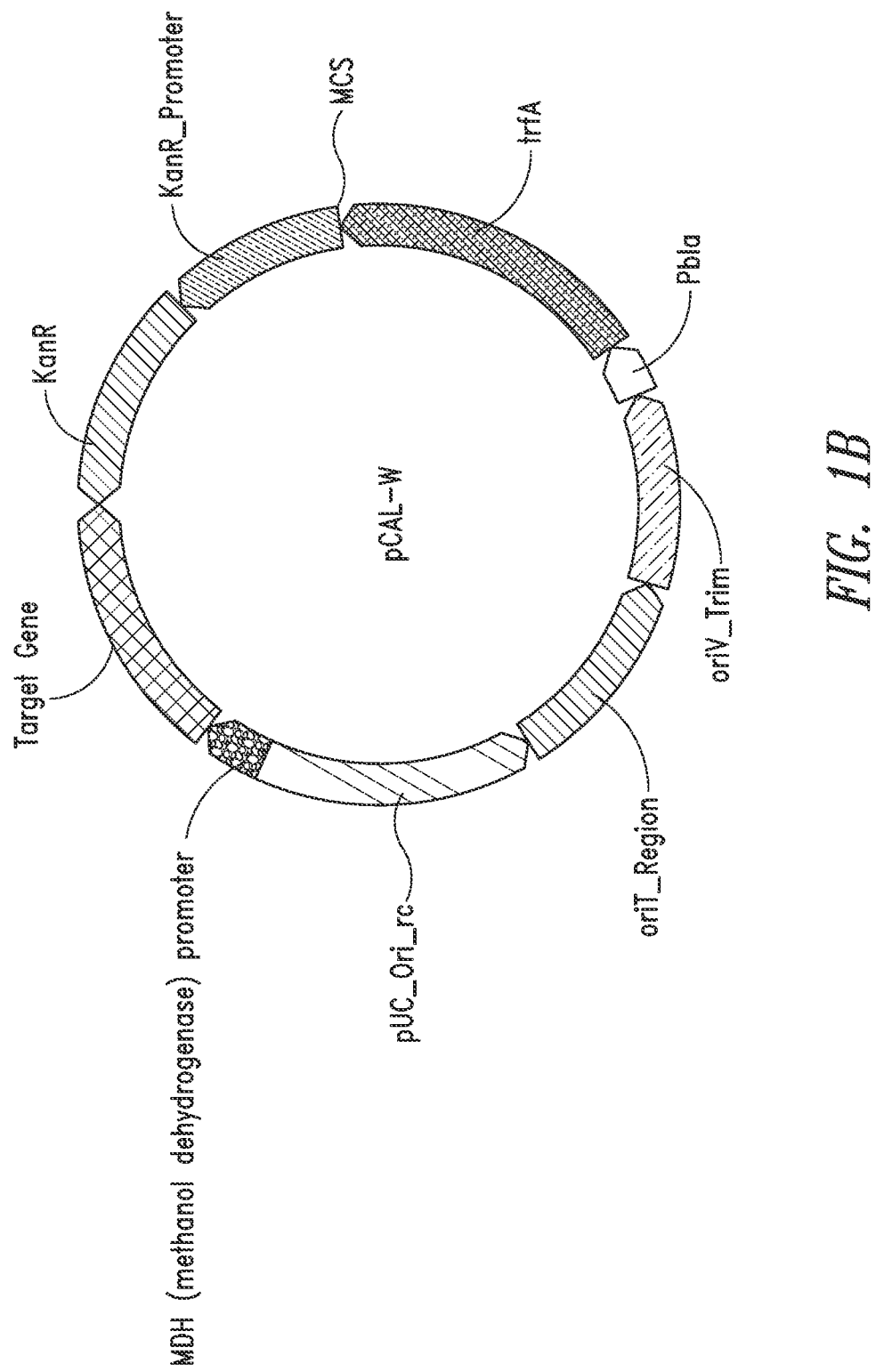
FIG. 1B is a schematic map of an exemplary pCAL vector for having an expression cassette comprised of a methanol dehydrogenase (MDH) promoter from *M. capsulatus* Bath, large subunit n229 (MCA0779), operably linked to a target gene. This vector is referred to herein as pCAL-W, which can be used in methanotrophic bacteria.

A map of an exemplary vector that comprises components (1) to (5) is shown in FIG. 1B, wherein "Pbla" refers to a β-lactamase promoter, "trfA" refers to a nucleic acid molecule encoding a replication initiation protein TrfA, "MCS" refers to a multiple cloning site region, "KanR_Promoter" refers to a kanamycin resistance promoter, "KanR" refers to a nucleic acid molecule encoding a kanamycin resistance protein, "target gene" refers to any inserted nucleic acid molecule encoding a target protein of interest (e.g., a metabolism enzyme, such as from the glycolysis/gluconeogenesis pathways), "MDH" refers to a methanol dehydrogenase promoter, "pUC_Ori_rc" refers to a pUC origin of replication, "oriT Region" refers to an origin of transfer, and "oriV_Trim" refers to shortened or truncated origin of replication.

In certain embodiments, the total length of components (1) to (5), if present, in a vector is no more than 8 kb, 7.5 kb, 7 kb, 6.5 kb, or 6 kb. The relatively small size facilitates manipulation of such a vector, and may improve transformation efficiency.

A vector provided herein may further comprise the expression regulatory nucleic acid molecules or expression cassettes described herein. Such a vector is useful for making a target protein whose expression is regulated by the expression regulatory nucleic acid. Alternatively or additionally, a vector may comprise an expression cassette other than those provided herein.

The vector provided herein may further comprise a nucleic acid sequence encoding a reporter protein, such as GFP, catechol 2,3-dioxygenase (XylE) or β-galactosidase (LacZ), with a multiple restriction site upstream of the reporter gene to allow easy insertion of a nucleic acid sequence potentially functional as a promoter. The expression level of the reporter is used to assess the promoter activity of the inserted nucleic acid sequence. Methods of constructing and using promoter-probe vectors are known, see, e.g., Ali and Murrel, *Microbiol.* 155:761-71, 2009, and Marx and Lidstrom, *Microbiol.* 147:2065-75, 2001.

Any of the aforementioned non-naturally occurring expression regulatory nucleic acid molecules, expression cassettes and vectors of the present disclosure may be introduced into host cells of this disclosure. The description of the types of host cells and transformation of host cells as described herein are also applicable.

The present disclosure also provides methods for using expression regulatory nucleic acid molecules, expression cassettes and vectors provided herein in genetic manipulation of methanotrophic bacteria. For example, the present disclosure provides a method for producing a target polypeptide by culturing host cells transformed with vectors provided herein that comprise an expression regulatory nucleic acid molecule or expression cassette encoding a target polypeptide. The methods may further comprise purifying an expressed target polypeptide from the cultured host cells. The description of culturing host cells and purifying target proteins is described herein.

The following examples are for illustration and are not limiting.

EXAMPLES

Example 1

LacI Inducible Promoters for Methanotrophs

Figure 2A:
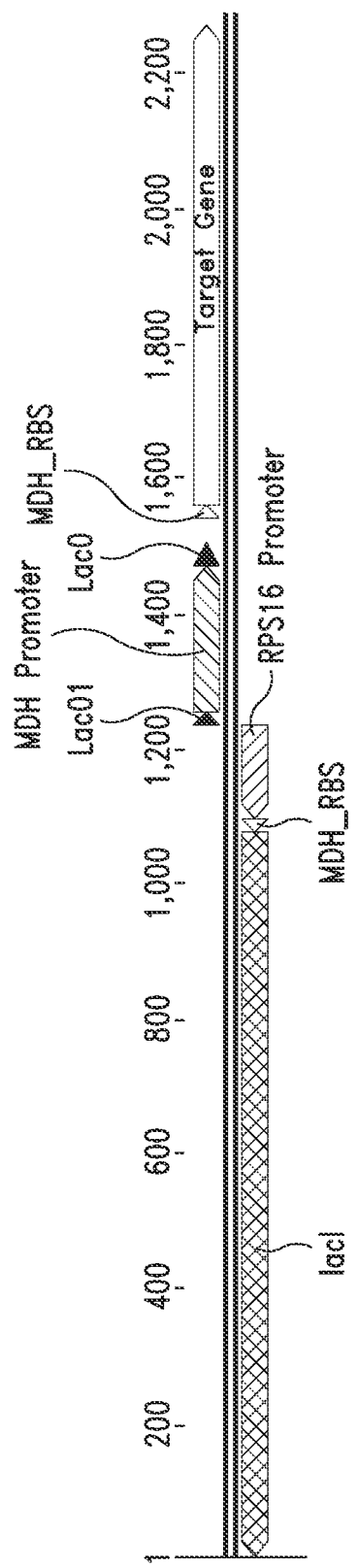
FIG. 2A is a schematic representation of an exemplary LacI inducible expression cassette for use in methanotrophic bacteria. The target gene is operably linked to an MDH promoter and ribosome binding sequence (RBS) containing the lac operator (lacO and lacO1). The lacI nucleic acid molecule encodes a $LacI^q$ and is operably linked to 30S ribosomal protein S16 (MCA0392) promoter linked to a MDH RBS (SEQ ID NO.:15). For example, such an expression cassette can be inserted into a pCAL vector in the same location as the MDH promoter-Target Gene in the pCAL-W vector of FIG. 1B, which is referred to herein as a pCAL-I1 vector.
Figure 2B:
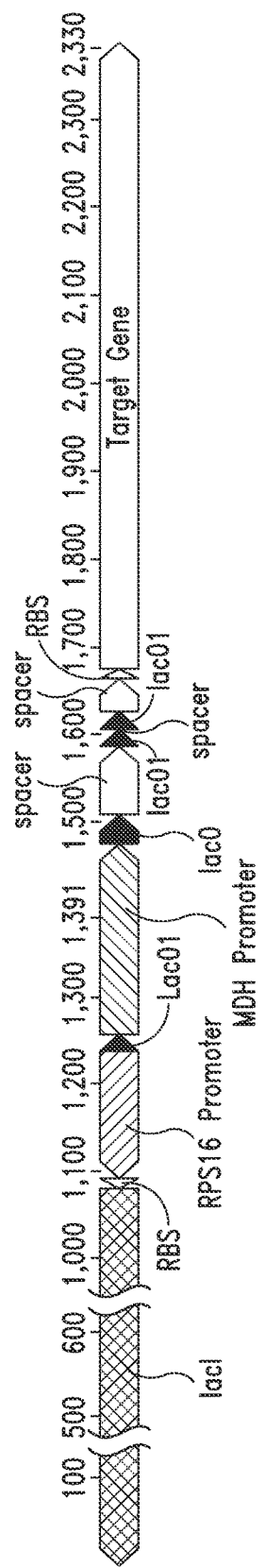
FIG. 2B is a schematic representation of an exemplary alternative lacI inducible expression cassette for use in methanotrophic bacteria. Such an expression cassette can be inserted into a pCAL vector, which is referred to herein as a pCAL-I2 vector.

*Methylococcus capsulatus* Bath strain was transformed with a vector containing a GFP ("Dasher") expression cassette comprising the GFP-coding sequence and the MDH promoter (denoted as "native" in FIG. 3) as a positive control, a vector without any GFP expression cassette as a negative control, and a vector comprising an inducible GFP expression cassette as shown in FIG. 2A. This was accomplished as follows:

The vectors were first transformed into *E. coli* S17-1 using standard electroporation methods. Transformants were selected from kanamycin-resistant colonies grown on LB-agar containing 30 µg/mL kanamycin. Transformed colonies were inoculated into LB media containing 30 µg/mL kanamycin and shaken overnight at 37° C. Aliquots (e.g., 100 µL) of overnight cultures were used to inoculate fresh LB media containing 30 µg/mL kanamycin and then grown to an optical density ($OD_{600}$) between 0.45-0.6 (mid-log phase growth). Aliquots of this second culture equivalent to an OD of 1.5 (e.g., 3 mL of a culture with an $OD_{600}$ of 0.5) were then pelleted via centrifugation and washed three times with sterile MM-W1 via centrifugation and resuspension.

In parallel, a sample of the *M. capsulatus* Bath (NCIMB 11132) recipient strain was inoculated into 100 mL serum bottles containing 20-50 mL MM-W1 media. The bottles were sealed with butyl rubber septa and crimped and between 40-60 mL of methane was then introduced into the sealed bottle. The bottles were shaken continuously in a 42° C. incubator until reaching an $OD_{600}$ of approximately 0.3. Approximately 5 mL of *M. capsulatus* Bath culture was then pelleted via centrifugation and mixed with the *E. coli* donor cells. This mixture was placed on an MM-W1 agar plate containing 0.5% yeast extract and incubated for 48 h at 37° C. in the presence of a 1:1 mixture of methane and air. After 24 h, cells were re-suspended in 0.5 mL sterile (MM-W1) medium and aliquots (100 µL) were spread onto MM-W1 agar plates containing 7.5 µg/mL kanamycin.

The plates were incubated in sealed chambers containing a 1:1 mixture of methane and air and maintained at 42° C. (*M. capsulatus* Bath). The gas mixture was replenished approximately every 2 days until colonies formed, typically after 5-8 days. Colonies were streaked onto MM-W1 plates containing kanamycin to confirm kanamycin resistance as well as to further isolate transformed methanotroph cells from residual *E. coli* donor cells.

Figure 6:
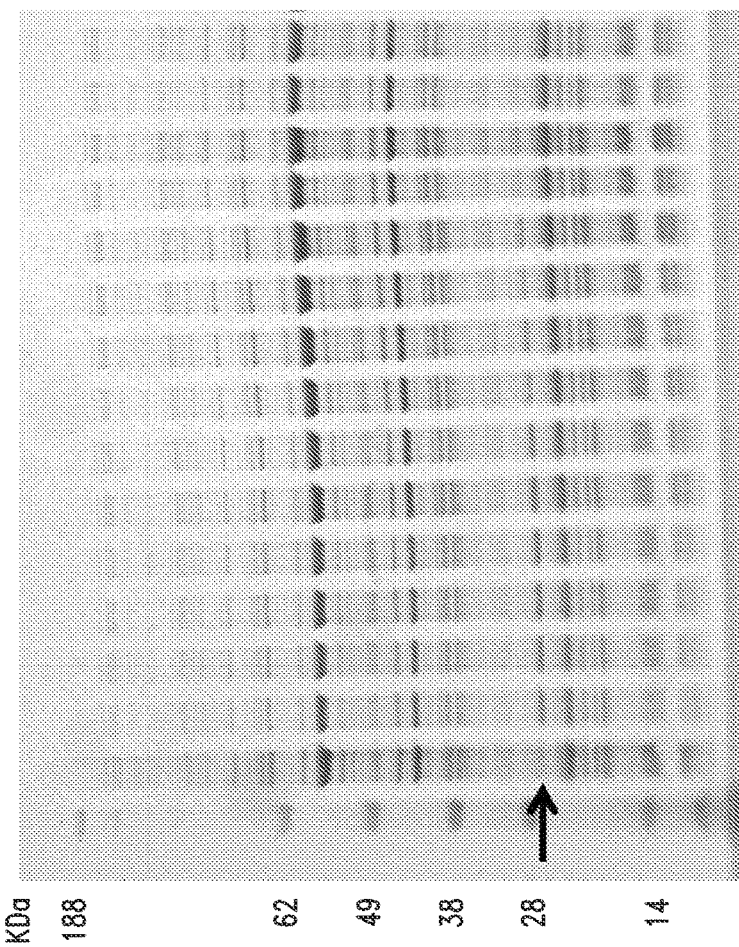
FIG. 6 is a photograph of electrophoresis separation of proteins from *M. capsulatus* Bath containing the pCAL-I-GFP vector (from duplicate cultures) cultured in the presence of various IPTG concentrations (0.1 mM to 10 mM). The arrow points to the Dasher protein that is about 26.6 KDa.

To induce GFP expression, cells were grown in MM-W1 medium with IPTG at a concentration between 0.5-10 mM either in liquid media or medium that had been solidified with 1.5% agar (see FIG. 3). The presence of GFP expression or function was verified by one or more of (1) PCR and sequencing, (2) Western blot analysis or Coomassie-stained protein gel (see FIGS. 6 and 7), and (3) fluorescence measurement (see FIGS. 4, 7, 9 and 11). For example, to verify transfer, colony material was boiled at 98° C. and subjected to PCR using standard conditions (for example, 98° C. for 1 min; 30 cycles of 98° C. for 10 s, 55° C. for 30 s, and 72° C. for 1 min; 72° C. for 10 min). As a further control, 1 µl each of the isolated plasmids was transformed back into *E. coli* XL1-Blue MRF' Kan (Stratagene, La Jolla, Calif.), and plasmids were isolated to verify by restriction endonuclease digests.

Figure 3B:
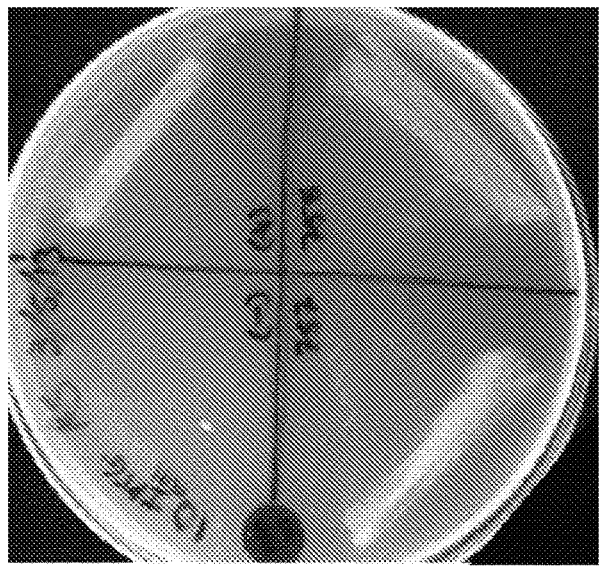
FIG. 3B is a photograph of a plate containing 10 mM IPTG to show the expression of a GFP variant ("Dasher") in the same *M. capsulatus* Bath transformants as described in FIG. 3A.
Figure 3A:
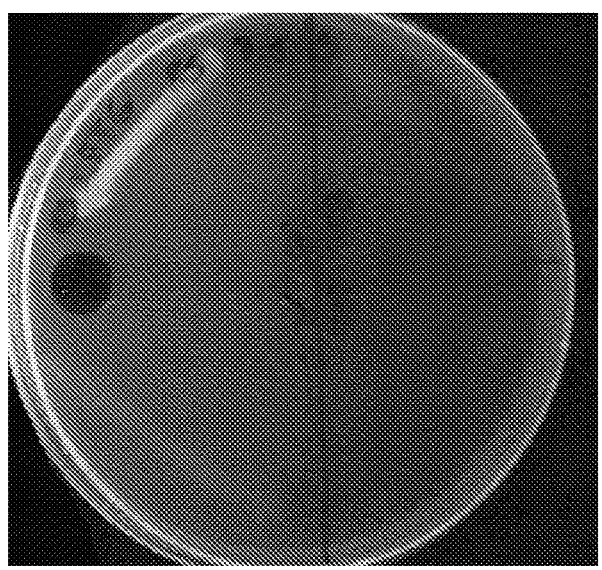
FIG. 3A is a photograph of a plate without IPTG (Isopropyl β-D-1-thiogalactopyranoside) to show expression of a green fluorescent protein (GFP) variant ("Dasher") in an *M. capsulatus* Bath strain transformed with a pCAL-W vector containing an expression cassette comprised of the MDH promoter from *M. capsulatus* Bath operably linked to the nucleic acid molecule encoding the GFP ("Native Promoter"), an *M. capsulatus* Bath strain transformed with a pCAL-W vector lacking a GFP coding sequence ("Empty Vector"), and a *M. capsulatus* Bath strain containing either a pCAL-I1 vector comprising the LacI inducible expression cassette from FIG. 2A or a or a $pCAL-I^v$ vector which comprises the same expression cassette from FIG. 2A except the nucleic acid molecule encoding wild-type $LacI^q$ (see SEQ ID NO.:39) is replaced with a nucleic acid molecule encoding a variant of $LacI^q$ (see SEQ ID NO.:33) ("Inducible Promoters"). The level of induction of target gene expression by the wild-type and variant $LacI^q$ proteins was substantially the same.

FIG. 3A shows that when no IPTG was added to a plate, bacteria containing the GFP expression cassette that comprises the constitutive MDH GFP expression cassette produced GFP protein, while neither bacteria without the GFP expression cassette ("empty vector") nor those containing inducible GFP expression cassette produced detectable GFP.

FIG. 3B shows that when 10 mM IPTG was added to the plate, bacteria containing no GFP expression cassette still did not produce GFP, bacteria containing the GFP expression cassette comprising the constitutive MDH GFP promoter cassette still produced GFP protein. However, bacteria containing the inducible GFP expression cassette produced GFP.

Thus, the results from FIGS. 3A and 3B show that the inducible GFP expression cassette was effective in inducing the expression of GFP with IPTG.

Figure 4:
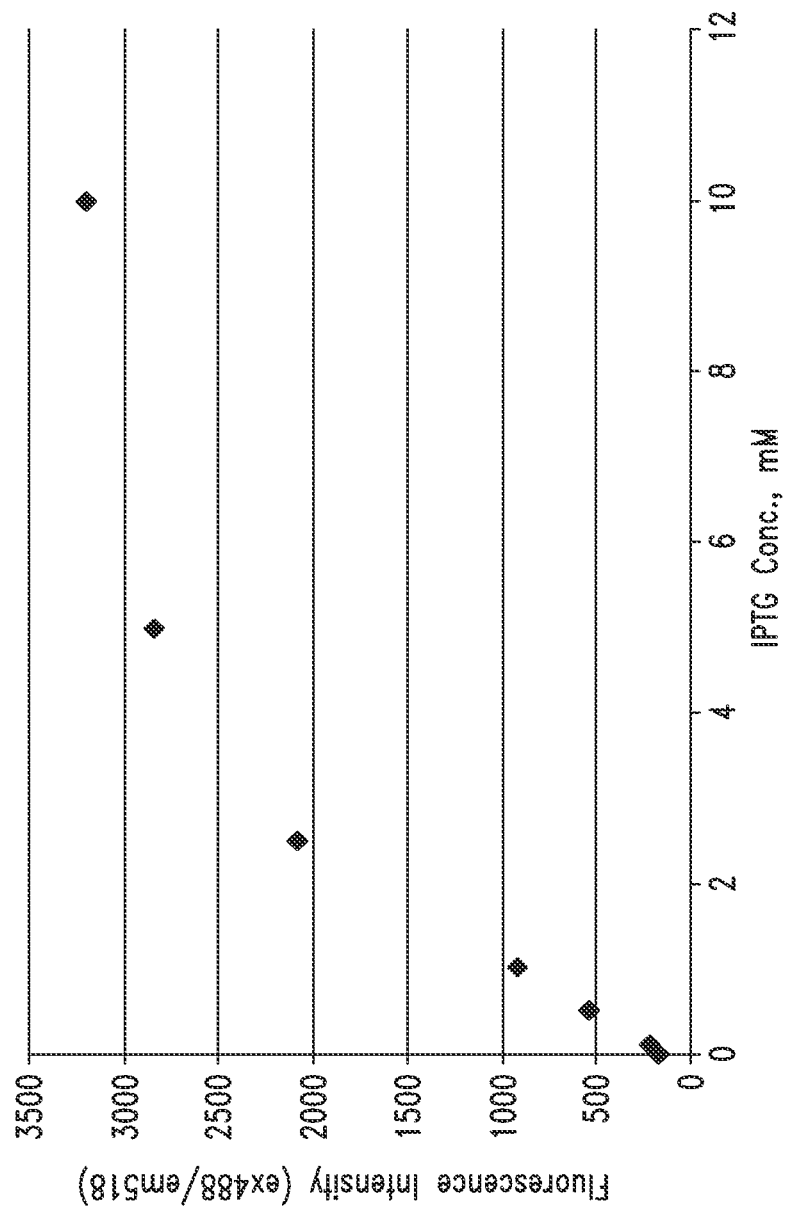
FIG. 4 is a graph showing Dasher fluorescence intensities with increasing IPTG concentrations (0.1 mM to 10 mM) in *M. capsulatus* Bath transformed with a pCAL-I1 vector containing a LacI inducible expression cassette operably linked to a nucleic acid molecule encoding the Dasher variant of GFP (pCAL-I1-GFP).

FIG. 4 shows that Dasher fluorescence intensity increased with increasing IPTG concentrations (up to 10 mM) in *M. capsulatus* Bath that contained the GFP inducible expression cassette.

Figure 5:
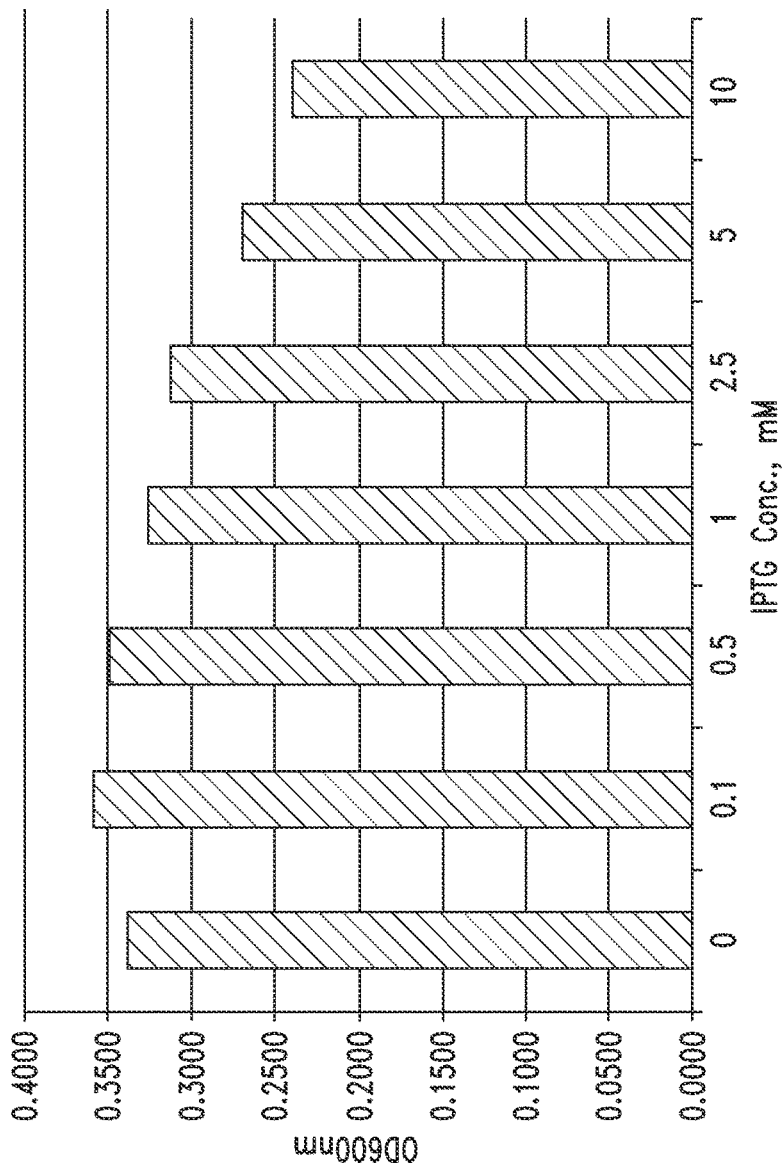
FIG. 5 is a graph showing growth of *M. capsulatus* Bath containing the pCAL-I-GFP vector in the presence of increasing IPTG concentrations.

FIG. 5 shows growth of *M. capsulatus* Bath that contained the GFP inducible expression cassette in the presence of increasing IPTG concentrations.

FIG. 6A shows electrophoresis of proteins isolated from *M. capsulatus* Bath that contained the GFP inducible expression cassette in the presence of various IPTG concentrations. Dasher is about 26.6 KDa. Its expression levels decreased in the presence of decreasing IPTG concentrations.

Figure 7:
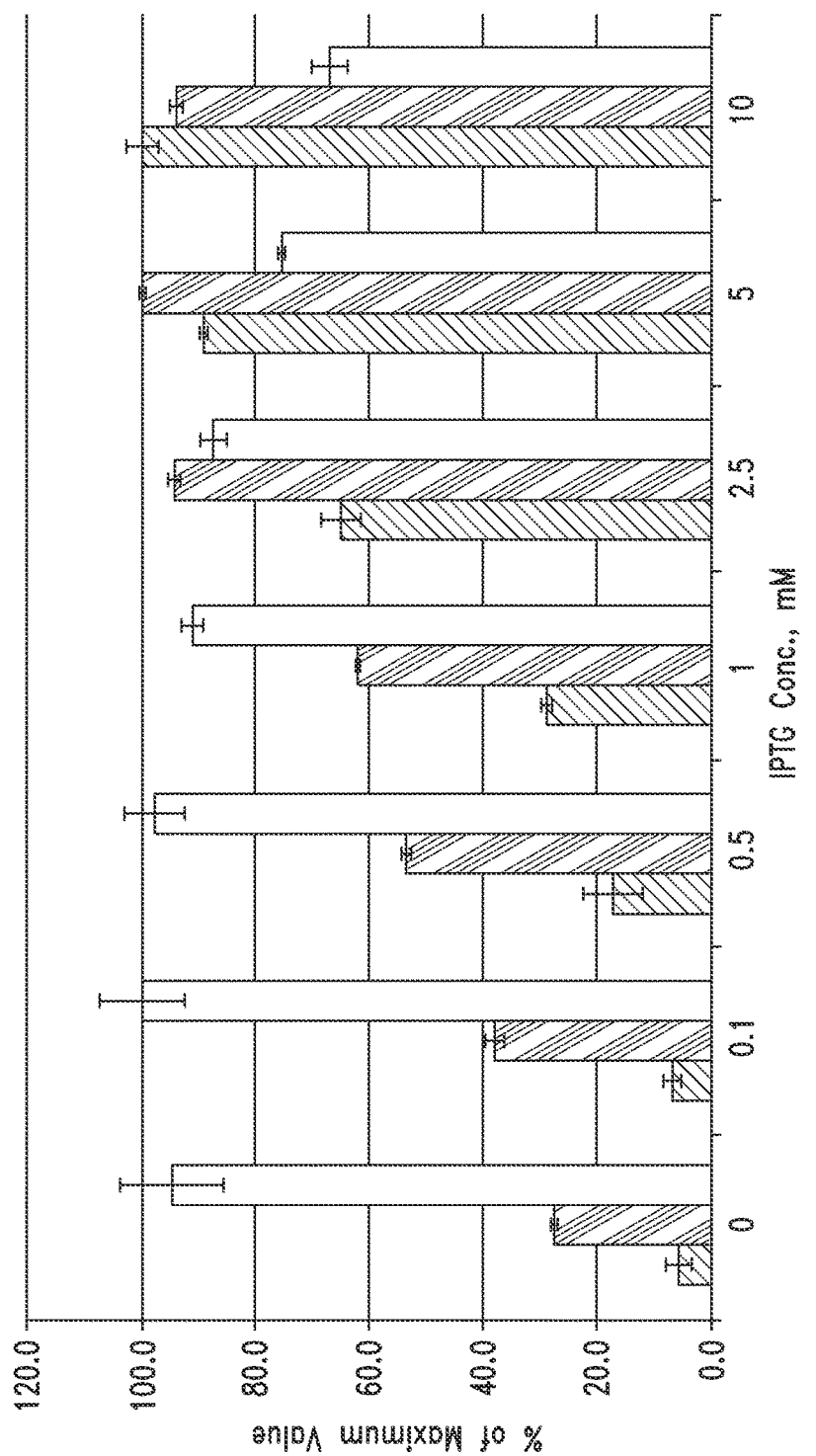
FIG. 7 is a graph showing percent relative fluorescence intensity of Dasher, percent relative expression level of Dasher protein, and percent relative growth of a *M. capsulatus* Bath containing the pCAL-I-GFP vector cultured in the presence of increasing IPTG concentrations (0.1 mM to 10 mM).

FIG. 7 shows Dasher relative fluorescence intensity, protein expression, and growth in the presence of increasing IPTG concentrations.

Figure 13:
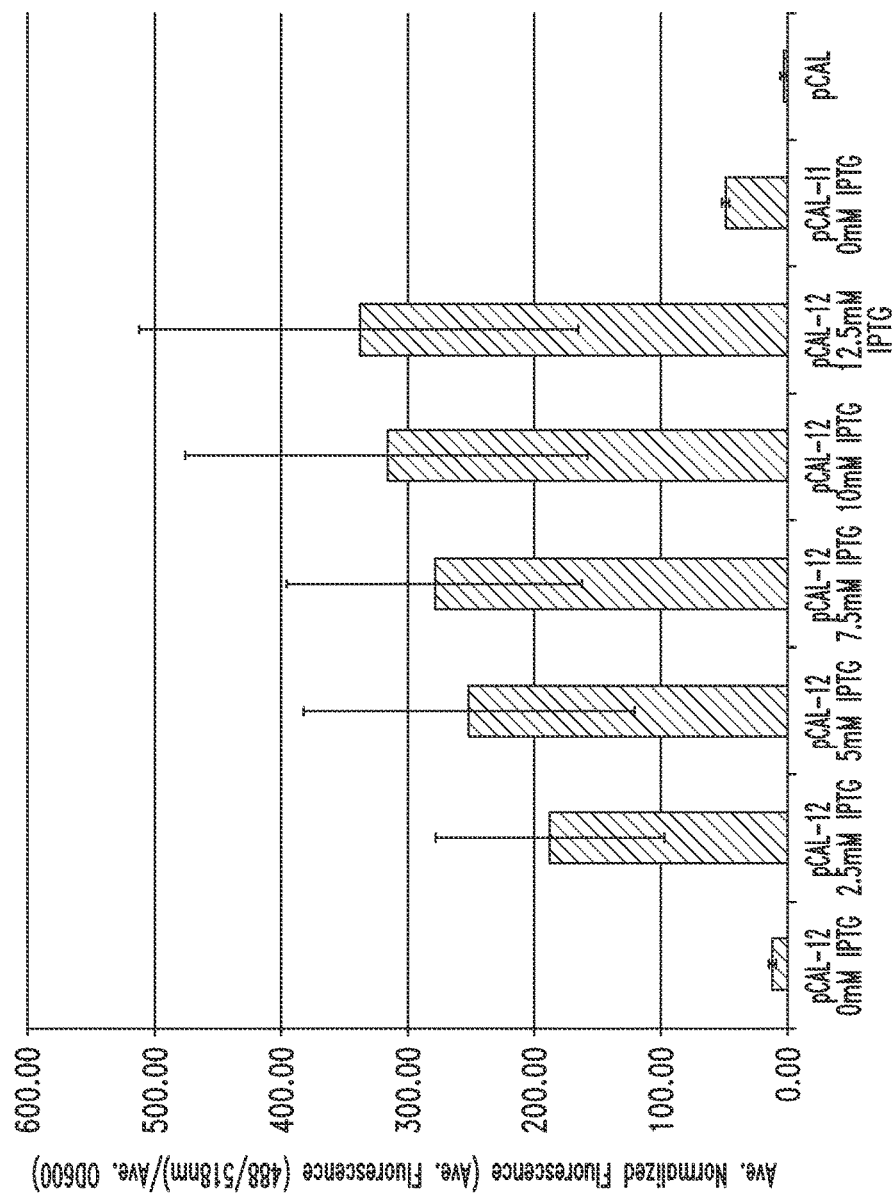
FIG. 13 is a graph showing the Dasher fluorescence intensities with increasing IPTG concentrations in *M. capsulatus* Bath strains containing either the alternative pCAL-I2 expression cassette (more tightly regulated than pCAL-I1) with the Dasher gene, the pCAL-I1 expression cassette with the Dasher gene, or the empty plasmid control pCAL, which does not contain a fluorescent protein coding sequence.

To reduce the level of leakiness in un-induced cells, the expression control sequence of the pCAL-I1 plasmid were reconfigured with more operator sequences (see FIG. 2B) to generate pCAL-I2. After introducing Dasher GFP under the control of the pCAL-I2 inducible promoter, the pCAL-I2-GFP construct was introduced into *M. capsulatus* Bath as described in this example and then cultured in presence or absence of inducer IPTG. FIG. 13 shows that the Dasher fluorescence intensity increased with increasing IPTG concentrations (from 2.5 mM to 12.5 mM IPTG) in *M. capsulatus* Bath strains containing the alternative pCAL-I2-GFP expression cassette. FIG. 13 shows that in the absence of IPTG, the pCAL-I2 plasmid is more tightly regulated than pCAL-I1 because the pCAL-I1 showed higher background levels of fluoresence, whereas the pCAL-I2 expression cassette with the Dasher gene was much closer to the empty plasmid control pCAL, which does not contain a fluorescent protein coding sequence.

Figures 14A, 14B:
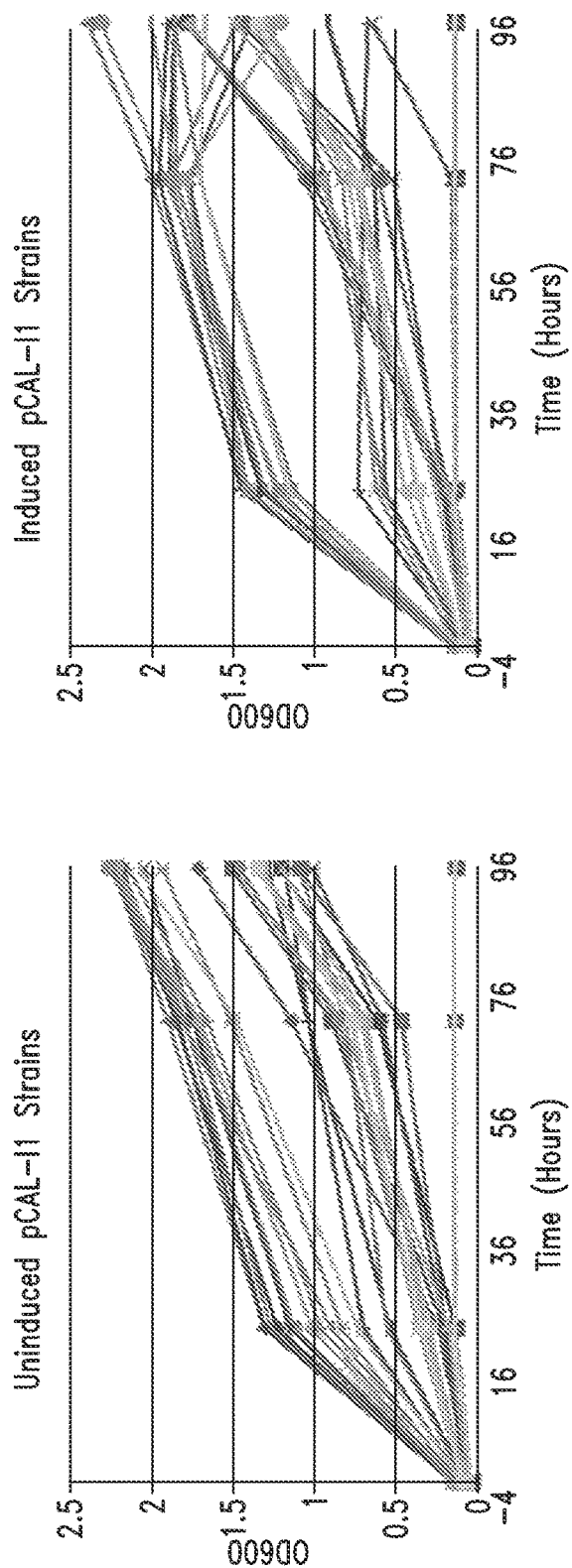
Figure 15:
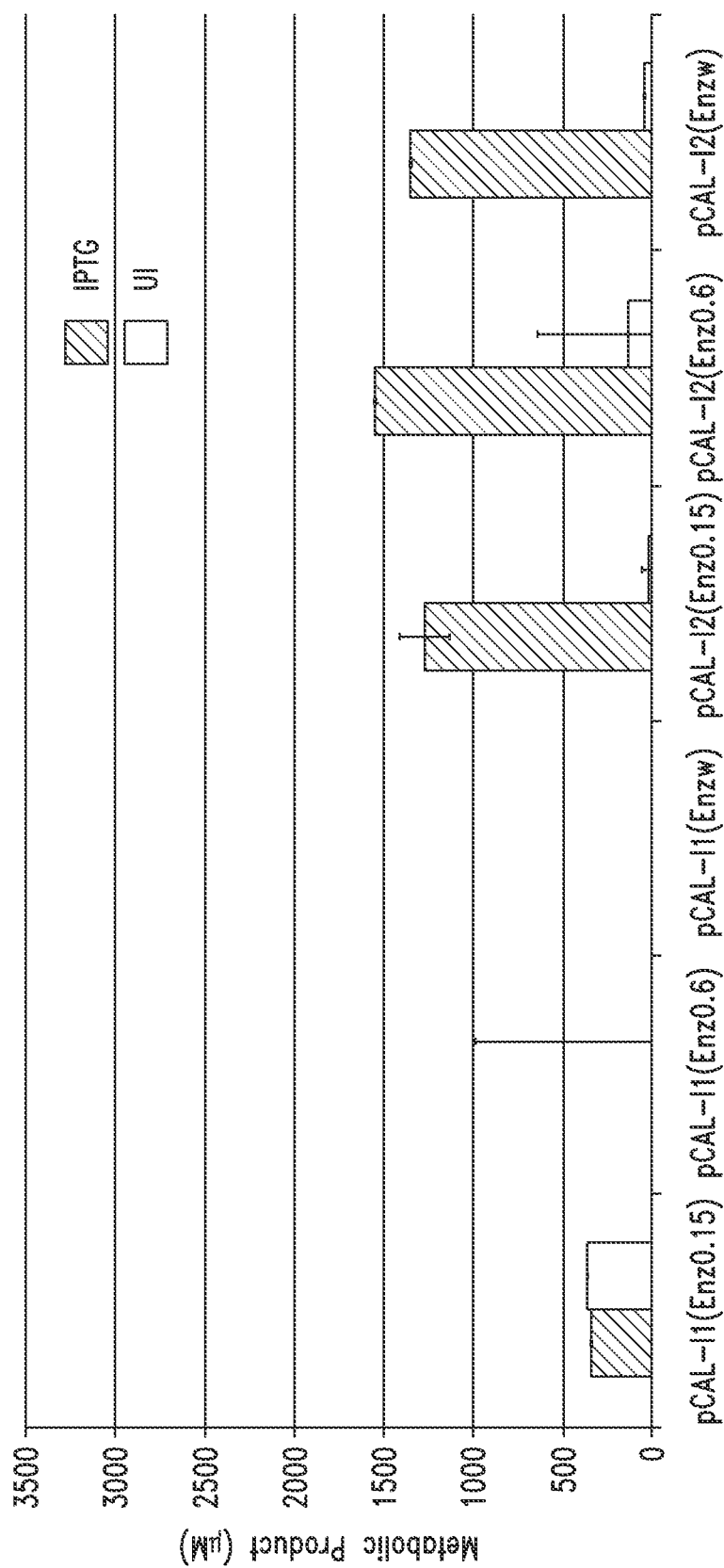
FIG. 15 shows the metabolite concentration 72 hours post-induction in six different strains expressing metabolic enzyme in either the pCAL-I1 expression construct (with three different RBSs—pCAL-I1(Enz0.15) contains RBS of SEQ ID NO.:24, pCAL-I1(Enz0.6) contains RBS of SEQ ID NO.:22, and pCAL-I1(Enz-w) contains RBS of SEQ ID NO.:40) or the pCAL-I2 expression construct (with three different RBSs—pCAL-I2(Enz0.15) contains RBS of SEQ ID NO.:24, pCAL-I2(Enz0.6) contains RBS of SEQ ID NO.:22, and pCAL-I2(Enz-w) contains RBS of SEQ ID NO.:40). The pCAL-I2 expression system enables higher production of a toxic metabolite in the "induced" condition, likely due to reduced expression of metabolic enzyme prior to IPTG induction.

To further evaluate the functionality of the pCAL-I2 inducible expression system, it was used with a nucleic acid molecule encoding a metabolic enzyme to test *M. capsulatus* Bath strains for their ability to form a toxic metabolite when the metabolic enzyme was expressed. FIGS. 14A and 14B show that growth of *M. capsulatus* Bath having the pCAL-I1 expression construct showed inconsistent and reduced growth whether the IPTG inducer was present or not. In contrast, growth of *M. capsulatus* Bath grown in the absence of IPTG were uniformly capable of continuing to grow over time (with no reduction even after 96 hours, FIG. 14C). Similarly, when *M. capsulatus* Bath was grown for 24 hours and then induced with 10 mM IPTG, the cells still grew to a high $OD_{600}$ although a bit more variable at 96 hours (FIG. 14D). This indicates that expression of a metabolic enzyme in the uninduced state from the pCAL-I2 expression construct is much lower relative to the pCAL-I1 expression construct. Metabolic enzyme catalyzes the formation of a metabolite that is toxic to the cells; therefore, reduced expression in an uninduced state (e.g., tighter control of "leakage" of expression of a gene coding for metabolic enzyme) enabled unhindered growth of the cells prior to induction. In addition, when examining the level of the toxic metabolite produced, FIG. 15 shows that the pCAL-I2 expression system enabled higher production of a toxic metabolite in the "induced" condition, likely due to reduced expression of metabolic enzyme prior to IPTG induction.

Both vectors provide regulatable expression systems useful for expressing target polypeptides or other products in methanothrophs.

Example 2

Constitutive and Inducible Production of a Target Product

I. *Methylococcus capsulatus* Bath Engineered for GFP or Lactate Production.

Host cells (*Methylococcus capsulatus* Bath) were engineered to possess an exogenous nucleic acid molecule encoding a green fluorescent protein ("Dasher", SEQ ID NO.:33) or a lactate dehydrogenase enzyme to produce lactate from a $C_1$ substrate (methane). Nucleic acid molecules encoding various different lactate dehydrogenases were codon optimized for *Methylococcus capsulatus* Bath and synthesized. The LDH encoding sequences were from *Streptococcus pasteurianus, Lactobacillus helveticus, Bos taurus, Pediococcus acidilactici, Rhizopus oryzae, Enterococcus faecalis, Lactobacillus casei, Bacillus megaterium, Taeniopygia guttata, Lactobacillus plantarum, Lactobaillus acidophilus, Staphylococcus aureus, Bacillus caldolyticus, Actinomyces viscosus, Bacillus anthracis, Ruminococcus torques, Listeria marthii, Bacillus subtilis, Enterococcus faecium, Bacillus thuringiensis, Geobacillus stearothermophilus, Deinococcus radiodurans, Plasmodium ovale* (variant), and *Thermus thermophilus*. The GFP or codon optimized LDH nucleic acid molecules were cloned into plasmid pCAL (FIG. 1A) downstream of one or more constitutive promoter systems comprising: (a) the putative promoter from the methanol dehydrogenase (MDH) gene from *M. capsulatus* Bath, large subunit (MCA0779)) (vector pCAL-W), (b) one of various different promoters (pCAL-16a, pCAL-S16, pCAL-t5, pCAL-trc, pCAL-trf), (c) one of various different promoters containing an MDH ribosome binding sequence (pCAL-S12W, pCAL-L13W, pCAL-S16W, pCAL-H6PW, pCAL-16aW), or one of four different mutated ribosomal binding sequences (vectors pCAL-Wm1.0, pCAL-Wm0.6, pCAL-Wm0.15, pCAL-Wm0.1). Alternatively, GFP or codon optimized LDH were cloned downstream of the MDH promoter in an IPTG-inducible ($LacI^q$) promoter system with native ribosomal binding sequence (vector pCAL-I1) or alternatively in the same vector with one of the four different mutated ribosomal binding sequences (vectors pCAL-I1m1.0, pCAL-I1-m0.6, pCAL-I1-m0.15, pCAL-I1-m0.1).

Plasmid pCAL, derived from the RK2 plasmid (see Schmidhauser et al., *J. Bacteriol.* 164:446, 1985, which is incorporated herein by reference) is a minimal plasmid containing sequences that encode a replication initiation protein (trfA) and promoter (Pbla), an origin of replication (oriV), an origin of transfer (oriT), and kanamycin resistance gene and promoter (KanR promoter). The vectors were introduced into *Methylococcus capsulatus* Bath via conjugative mating based on the methods reported by Ali and Murrell (*Microbiol.* 155:761, 2009).

The vectors were first transformed into *E. coli* S17-1 using standard electroporation methods. Transformation was confirmed by selection of kanamycin-resistant colonies on LB-agar containing 30 μg/mL kanamycin. Sequence of donor plasmid was verified via sequencing. Transformed colonies were inoculated into LB media containing 30 μg/mL kanamycin and shaken overnight at 37° C. Aliquots (e.g., 100 μl) of overnight cultures were used to inoculate fresh LB media containing 30 μg/mL kanamycin and then grown to an optical density ($OD_{600}$) between 0.45-0.6 (mid-log phase growth). Aliquots of this second culture (e.g., 3 mL of a culture with an $OD_{600}$ of 0.5) were then pelleted via centrifugation and washed three times with sterile MM-W1 via centrifugation and resuspension. A 10 mL aliquot of the overnight culture was then collected on a sterile 47 mm nitrocellulose filter (0.2 mm pore size). The *E. coli* donor cells were washed on the filter with 50 mL sterile NSM media to remove residual media and antibiotic.

In parallel, a sample of the *M. capsulatus* Bath (NCIMB 11132) recipient strain was inoculated into 100 mL serum bottles containing 20-50 mL MM-W1 media. The bottles were sealed with butyl rubber septa and crimped and between 40-60 mL of methane was then introduced into the sealed bottle. The bottles were shaken continuously in a 42° C. incubator until reaching an $OD_{600}$ of approximately 0.3. Approximately 5 mL of *M. capsulatus* Bath culture was then pelleted via centrifugation and mixed with the *E. coli* donor cells. This mixture was placed on an MM-W1 agar plate containing 0.5% yeast extract and incubated for 48 h at 37° C. in the presence of a 1:1 mixture of methane and air. After 24 h, cells were re-suspended in 0.5 mL sterile (MM-W1) medium and aliquots (100 μL) were spread onto MM-W1 agar plates containing 7.5 μg/mL kanamycin.

The plates were incubated in sealed chambers containing a 1:1 mixture of methane and air and maintained at 42° C. (*M. capsulatus* Bath). The gas mixture was replenished approximately every 2 days until colonies formed, typically after 5-8 days. Colonies were streaked onto NSM plates containing kanamycin to confirm kanamycin resistance as well as to further isolate transformed methanotroph cells from residual *E. coli* donor cells.

The presence of GFP or ldh expression (or LDH function) was verified by (1) PCR and sequencing and/or (2) assaying for the presence of fluorescence or lactate, respectively. For example, to verify transfer, colony material was boiled at 98° C. and subjected to PCR using standard conditions (98° C. for 1 min; 30 cycles of 98° C. for 10 s, 55° C. for 30 s, and 72° C. for 1 min; 72° C. for 10 min). Optionally, as a further control, 1 µl each of the isolated plasmids were transformed back into *E. coli* XL1-Blue MRF' Kan (Stratagene, La Jolla, Calif.), and the plasmids were isolated to verify by restriction endonuclease digests.

Each of the recombinant *M. capsulatus* Bath were cultured at 42° C. in 24-well plates containing MM-W1 medium contained in sealed chambers. The headspace composition was adjusted to a 1:1 volume of methane:air. The bottles were shaken at a rate of 200-250 rpm. Alternatively, the culture was maintained on MM-W1-media plates solidified with 1.5% w/v agar grown in a gas-tight chamber containing a 1:1 (v/v) methane:air gas mixture. Plates were incubated inverted in the chamber at 42° C.

Production of Lactate from a $C_1$ Substrate ($CH_4$) or Fluorescence from GFP

*M. capsulatus* Bath transformed with a pCAL vector alone (negative control without the exogenous GFP or LDH encoding nucleic acid and promoter) or vector containing the exogenous GFP or LDH nucleic acid and various promoter systems were used to inoculate 2.5 mL MM-W1 media/well of 24 well plates having 7.5 µg/mL kanamycin. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$-Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$-Na-EDTA were added after the media was autoclaved and cooled. The plates were placed in sealed chambers and the headspace was flushed with a 1:1 mixture of air and methane as the carbon source for *M. capsulatus* Bath, the plates were sealed and then shaken continuously at a rate of 200-250 rpm during incubation at 42-45° C. for a 24 hour pre-culture. Then, new 24 well plates containing 2.5 mL fresh MM-W1 and kanamycin were inoculated with 0.25 mL of the pre-culture and incubated at 42-45° C. for 72 hours. *M. capsulatus* Bath strain containing the MDH promoter in the IPTG-inducible (LacI') promoter system was grown in the presence of 0.1-10 mM IPTG). Cells were harvested by centrifugation and the supernatants were analyzed using the EnzyFluo™ L-Lactate Assay Kit as per the manufacturer's instructions (BioAssay Systems, Hayward, Calif.) with the exception that the supernatants were incubated with the kit reagents for two hours prior to measuring fluorescence. Since methane was the only carbon source provided to the cells, all lactate produced must have been derived from methane.

Results

The detection of fluorescence produced by *M. capsulatus* Bath containing any one of the pCAL-GFP plasmids with a constitutive promoter are provided in Table 1. These results show that level of target polypeptide produced in a methanotroph can be altered by changing the promoter/ribosome binding sequence configurations.

TABLE 1

Various Promoters with Different RBSs for use in Methanotrophs

| SEQ ID NO. | Plasmid/Sequence Description | Normalized Fluorescence (%)* |
|---|---|---|
| 14 | pCAL-W | 100 |
| 16 | pCAL-16a (*Methylomonas* 16a, hexulose 6-phosphate synthase promoter) | 58 |
| 15 | pCAL-S16 (*M. capsulatus* Bath, 30S RP S16 promoter) | 16 |
| 17 | pCAL-t5 (Bacteriophage T5 promoter) | 14 |
| 18 | pCAL-trc (Trc promoter) | 3 |
| 42 | pCAL-trf (trfA promoter from RK2) | 7 |
| 43 | pCAL-S12W (*M. capsulatus* Bath, 30S RP S12 promoter with MDH RBS) | 12 |
| 44 | pCAL-L13W (*M. capsulatus* Bath, 50S RP L13 promoter with MDH RBS) | 17 |
| 28 | pCAL-S16W (*M. capsulatus* Bath, 30S RP S16 promoter with MDH RBS) | 32 |
| 29 | pCAL-H6PW (*Methylomonas* 16a, hexulose-6-phosphate synthase promoter with MDH RBS) | 63 |
| 30 | pCAL-16aW (*Methylomonas* 16a, moxF promoter with MDH RBS) | 72 |
| 19 | pCAL-Wm1.0 (*M. capsulatus* Bath, MDH promoter with variant RBS of SEQ ID NO: 20) | 65 |
| 21 | pCAL-Wm0.6 (*M. capsulatus* Bath, MDH promoter with variant RBS of SEQ ID NO: 22) | 46 |
| 23 | pCAL-Wm0.15 (*M. capsulatus* Bath, MDH promoter with variant RBS of SEQ ID NO: 24) | 31 |
| 25 | pCAL-Wm0.1 (*M. capsulatus* Bath, MDH promoter with variant RBS of SEQ ID NO: 26) | 33 |

*Normalized to MDH promoter of SEQ ID NO: 14 (100%)

The limit for designating recombinant cells as having positive LDH activity (measured as the level of lactate production) was set at a threshold of 3-fold and was detected at levels greater than a 1,000-fold higher concentration of lactate than the assay background from negative control strains (i.e., lacking or not expressing LDH). Generally, expression was very low (threshold level) or not detectable when the LDH coding molecule was in a pCAL-W vector. In three cases, LDH activity (*Bos Taurus*, *L. helveticus*, or *Plasmodium ovale*) was not detected above the threshold level, while in another three cases, colonies and high LDH activity (*Bacillus anthracis*, *Bacillus thuringensis*, and *Deinococcus radiodurans*) were only observed in hosts in which an inducible promoter controlled the LDH expression. For all the rest of the LDH, good to very good expression was observed with the inducible promoter.

II. *Methylosinus* and *Methylomicrobium* Engineered for Lactate Production.

Host cells (*Methylosinus trichosporium* OB3b and *Methylomicrobium buryatense* 5G) were engineered to possess an exogenous lactate dehydrogenase (ldh) nucleic acid to allow the production of L-lactate from a $C_1$ substrate (methane). The exogenous LDH encoding nucleic acid molecules from Part I above were individually cloned into expression vector pMS10 (a pMS3 equivalent plasmid with kanamycin resistance gene from a different source) downstream of a promoter system for conjugation into *M. trichosporium* OB3b or *M. buryatense* 5G based on the methods reported by Ali and Murrell (Microbiol. 155:761, 2009). For transformation of *Methylosinus trichosporium* OB3b, the promoter was the Ob3b promoter sga (serine-glycoxylate transaminase). For transformation of *Methylomicrobium buryatense* 5G, the promoter was either *Methylomonas* 16a moxF (methanol dehydrogenase) promoter (SEQ ID NO.:30) or *Methylomonas* 16a hps (hexulose-6-phosphate synthetase) promoter (SEQ ID NO.:29).

Briefly, the pCAL mobilizable plasmid containing one or more nucleic acids of interest (e.g., ldh) and encoding kanamycin resistance was first transformed into *E. coli* S17-1 using standard electroporation methods. Transformation was confirmed by selection of kanamycin-resistant colonies on LB-agar containing 30 μg/mL kanamycin. Transformed colonies were inoculated into LB media containing 30 μg/mL kanamycin and shaken at 37° C. until the OD600 reached 1.0. A 1.0 mL aliquot of the culture was then collected in a sterile Eppendorf tube (1.6 ml size). The *E. coli* donor cells were washed 2×1.0 mL sterile MM-W1 (OB3b) or NMS (5G) media to remove residual media and antibiotic.

In parallel, a sample of the *M. trichosporium* OB3b (NCIMB 11131) or *M. buryatense* 5G (from Dr. Mary Lidstrom, University of Washington) recipient strain was inoculated into 100 mL serum bottles containing 20-50 mL MM-W1 (OB3b) or NMS (5G) media. The headspace of the bottles was then flushed with a 1:1 mixture of oxygen and methane, and the bottles were sealed with butyl rubber septa and crimped. The bottles were shaken continuously in a 30° C. incubator until reaching an $OD_{600}$ of approximately 0.5. The OB3b or 5G cells were then collected by centrifugation and washed with 50 mL of sterile MM-W1 or NMS media. The washed cells were resuspended in sterile MM-W1 or NMS media to an $OD_{600}$ of 1.0 and aliquots mixed with the donor *E. coli* at a recipient:donor ratio of 2:1. The cell mixture was pelleted by centrifugation and the cell pellet spotted on an MM-W1 or NMS agar plate containing 0.5% yeast extract and incubated for 48 h at 30° C. in the presence of a 1:1 mixture of methane and air. After 48 h, cells were re-suspended in 1.0 mL sterile medium and aliquots (100 μL) were spread onto MM-W1 or NMS agar plates containing 4-7.5 μg/mL kanamycin.

The plates were incubated in sealed chambers containing a 1:1 mixture of methane and air and maintained at 30° C. The gas mixture was replenished every 2 days until colonies formed, typically after 7-14 days. Colonies were streaked onto MM-W1 or NMS plates containing kanamycin to confirm kanamycin resistance as well as to further isolate transformed methanotroph cells from residual *E. coli* donor cells.

The presence of ldh expression or LDH function was verified by one or more of (1) PCR and sequencing, (2) Western blot analysis, and (3) assaying for the presence of lactate. For example, to verify transfer, plasmid DNA was isolated and subjected to PCR using OneTaq 2× Master Mix with Standard buffer (New England BioLabs) using standard conditions (95° C. for 5 min; 25 cycles of 95° C. for 30 s, 60° C. for 30 s, and 72° C. for 1 min; 72° C. for 10 min) and primer sets specifically designed to bind outside of and interior to the ldh nucleic acid. The original plasmid DNA containing the cloned ldh nucleic acid(s) was used as a positive control for the PCR.

The recombinant *M. trichosporium* OB3b or *M. buryatense* 5G were cultured at 30° C. in serum bottles containing MM-W1 or NMS containing 4-7.5 ug/ml kanamycin medium. The headspace composition was adjusted to a 1:1 volume of methane:air. The bottles were shaken at a rate of 200-250 rpm. Alternatively, the culture was maintained on MM-W1 or NMS media plates solidified with 1.5% w/v agar grown in a gas-tight chamber containing a 1:1 (v/v) methane:air gas mixture. Plates were incubated inverted in the chamber at 30° C.

Production of Lactate from a $C_1$ Substrate ($CH_4$)

*M. trichosporium* OB3b or *M. buryatense* 5G transformed with a vector alone or vector containing an ldh nucleic acid were used to inoculate 2.0 mL MM-W1 or NMS media in Balch tubes (Bellco Glass) having 5 μg/mL kanamycin. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 1 μM $CuSO_4*5H_2O$, 10 μM $Fe^{III}$-Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$-Na-EDTA were added after the media was autoclaved and cooled. The composition of the NMS media used was as follows: 1.00 g/L $MgSO_4*7H_2O$, 0.02 g/L $CaCl_2*6H_2O$, 1.00 g/L $KNO_3$, 15 g/L NaCl, 20 ml Phosphate buffer (5.44 g/L $KH_2PO_4$, 14.34 g/L $Na_2HPO_4*12 H_2O$), 50 ml Carbonate buffer (45 ml of 1M $NaHCO_3$+5 ml 1M $Na_2CO_3$), 2 ml Trace Element solution (0.5 g/L $Na_e$-EDTA, 1.0 g/L $FeSO_4*7H_2O$, 0.75 g/L Fe-EDTA, 0.8 g/L $ZnSO_4*7H2O$, 0.005 g/L $MnCl_2*4H_2O$, 0.03 g/L $H_3BO_3$, 0.05 g/L $CoCl_2*6H_2O$, 0.4 g/L Cu-EDTA, 0.6 g/L $CuCl_2*2H_2O$, 0.002 g/L $NiCl_2*6H_2O$, 0.05 g/L $Na_2MoO_2*2H2O$) (Ojala, D. S., et al., *Methods in Enzymology*, Vol. 495, pp. 99-118). Sterile phosphate and carbonate buffers were added after the solution cooled to room temperature. The plate headspace was flushed with a 1:1 mixture of oxygen and methane as the carbon source for the strains, the tubes were sealed with butyl rubber septa, crimped, and then shaken continuously at a rate of 200-250 rpm during incubation at 30° C. for a 72 hours. Cells were harvested by centrifugation and the supernatants were analyzed using the EnzyFluo™ L-Lactate Assay Kit as per the manufacturer's instructions (BioAssay Systems, Hayward, Calif.) with the exception that the supernatants were incubated with the kit reagents for two hours prior to measuring fluorescence. Results were normalized to $OD_{600}$ values for each corresponding culture. Since methane was the only carbon source provided to the cells, all lactate produced must have been derived from methane.

Results

*M. trichosporium* OB3b and *M. buryatesne* 5G were altered to produce L-lactate by introducing and expressing an exogenous L-lactate dehydrogenase nucleic acid. The various exogenous lactate dehydrogenase nucleic acids were operatively linked to a constitutive promoter in an expression vector that functions in methanotrophs.

In all cases where lactate was produced, the $OD_{600}$ of the cultures ranged from 0.31 to 0.71 and all recombinant strains produced low, but detectable levels of lactate (1-20 μM greater than 3-fold higher concentrations of lactate than strains not known to be carrying a functional LDH nucleic acid).

Overall

The data demonstrate that the production of active polypeptides of interest encoded by a nucleic acid molecule contained in an expression cassette of this disclosure (constitutive or inducible) carried on a vector can be efficiently accomplished in various different methanotrophic bacteria, including *Methylococcus capsulatus* Bath, *Methylosinus trichsporium* OB3b, and *Methylomicrobium buryatense* 5G. Furthermore, these data show that different vectors can be used for different purposes. For example, an inducible promoter may be used when an encoded product is potentially toxic or lethal.

Example 3

A Sodium Benzoate Inducible Expression System for *Methylococcus capsulatus* Bath

*Methylococcus capsulatus* Bath strain was transformed with a vector containing a sodium benzoate inducible GFP expression cassette as shown in FIG. 8, according to the following procedures.

A. Media and Culture Conditions

If not stated otherwise, the following media and culture conditions were used in Examples 2, 3, and 4, and are referred to as "standard conditions."

*Escherichia coli* cultures were propagated at 37° C. in Lysogeny Broth (LB). Where necessary, LB medium was solidified with 1.5% (w/v) agar and/or supplemented with 30 µg/mL kanamycin. *M. capsulatus* Bath cultures were grown in 25 mL MM-W1 medium in 125 mL serum bottles containing a 1:1 (v/v) methane:air gas mixture. The composition of the medium MM-W1 was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$-Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$-Na-EDTA were added after the media was autoclaved and cooled. Where necessary, liquid MM-W1 media was supplemented with 15 µg/mL kanamycin (Sigma Aldrich) and 1 mM, 5 mM, 7.5 mM, or 10 mM sodium benzoate or 1 mM, 5 mM, 7.5 mM, or 10 mM 3-methylbenzoate ("3 MB"). *M. capsulatus* Bath cultures were incubated with 250 rpm agitation at 42° C. When required, MM-W1 medium was solidified with 1.5% (w/v) agar and supplemented with 7.5 µg/mL kanamycin. Agar plates were incubated at 42° C. in a gas-tight chamber containing a 1:1 (v/v) methane:air gas mixture.

B. Transformation of *M. capsulatus* Bath by Conjugation

*M. capsulatus* Bath wild type or mutant strains were grown under standard conditions for 24 h or until the culture reached an optical density at 600 nm ($OD_{600}$) of 1. 1.5 mL of this culture were pelleted, washed three times with MM-W1 medium, and then re-suspended in 0.5 mL MM-W1. In parallel, an *Escherichia coli* S17-λ pir strain with the plasmid to be transferred into *M. capsulatus* Bath was grown under standard conditions and in the presence of 30 µg/mL kanamycin for 16 h. The culture was diluted to an $OD_{600}$ of 0.05 and then grown further under standard conditions and in the presence of 30 µg/mL kanamycin until it reached an $OD_{600}$ of 0.5. 3 mL of the culture were pelleted, washed three times with MM-W1 medium, and then combined with 0.5 mL of the *M. capsulatus* Bath suspension. The mixed suspension was pelleted, then re-suspended in 40 µL of MM-W1 medium and spotted onto dry MM-W1 agar plates containing 0.2% yeast extract. Plates were incubated for 48 h at 37° C. in the presence of a 1:1 mixture of methane and air. After 24 h, cells were re-suspended in 1 mL sterile MM-W1 medium and 100-4 aliquots (undiluted and 1:100 dilution) were spread onto MM-W1 agar plates containing 7.5 µg/mL kanamycin. The plates were incubated in gas-tight chambers containing a 1:1 mixture of methane and air and maintained at 42° C. The gas mixture was replenished every 2 days until colonies formed, typically after 5-7 days. Colonies were streaked onto MM-W1 agar plates containing 7.5 µg/mL kanamycin to confirm kanamycin resistance as well as to further isolate transformed *M. capsulatus* Bath cells from residual *E. coli* donor cells. The presence of the correct plasmid in *M. capsulatus* Bath was verified by PCR and sequencing.

C. Construction of a Na Benzoate Inducible Expression System

A sodium benzoate inducible expression system for *M. capsulatus* Bath was designed by combining elements from the *Pseudomonas fluorescens* MB214 benzoate metabolic operon (Genbank accession number DQ172832) and a methanotroph-specific promoter. For this purpose a DNA fragment containing the following features was constructed via gene synthesis: (1) A codon optimized version of the benR activator gene (SEQ ID NO.: 47) under control of a constitutive methanotroph-specific ribosomal protein promoter and the MDH ribosomal binding sequence and (2) the intergenic region upstream of benA and downstream of the benR activator gene (containing the ben promoter $P_{ben}$ and the associated benA ribosomal binding sequence) (SEQ ID NO.:48). The entire fragment was flanked by BsaI restriction sites for cloning into a promoter probe plasmid. This plasmid contained the following genetic elements: a Bath codon-optimized variant of the green fluorescent protein (GFP), a kanamycin selection marker (KanR), a pUC-based origin of replication (functional in *E. coli* but non-functional in *M. capsulatus* Bath), an oriV (origin of replication functional in *M. capsulatus* Bath), a trfA gene (required for replication initiation of oriV based plasmids) and an origin of transfer (oriT) (which is required for conjugational transfer). Subsequently the synthesized DNA fragment was cloned into the promoter probe plasmid such that GFP was controlled by the ben promoter yielding the plasmid pCAL-B shown in FIG. 8. The pCAL-B plasmid was then introduced into *M. capsulatus* Bath by conjugation as described above. The presence of the correct plasmid in *M. capsulatus* Bath was verified by PCR and sequencing.

Functionality of the sodium benzoate inducible expression system was assessed by testing strains for their ability to fluoresce when induced with sodium benzoate. For this purpose, the *M. capsulatus* Bath strain containing the sodium benzoate inducible GFP expression cassette was used to inoculate 2.5 mL MM-W1 media/well of 24-well plates supplemented with 15 µg/mL kanamycin. In parallel, a *M. capsulatus* Bath wild type strain serving as a negative control was used to inoculate 2.5 mL MM-W1 media/well of a 24-well plate. The plate headspace was flushed with a 1:1 mixture of oxygen and methane as the carbon source for *M. capsulatus* Bath, the plates were sealed and then shaken continuously at a rate of 200-250 rpm during incubation at 42° C. for a 24 hour pre-culture. Then, new 24-well plates containing 2.5 mL fresh MM-W1, and where necessary 15 µg/mL kanamycin, were inoculated with 0.25 mL of the pre-culture and incubated at 42° C. for 72 h. All strains were grown in four sets of triplicates, whereas three sets were induced 24 h post-transfer with 1, 5, or 7.5 mM sodium benzoate and the fourth set was left un-induced. $OD_{600}$ readings and fluorescence measurements (Excitation: 488 nm/Emission: 518 nm) were taken at induction, and 24 h, 48 h, and 72 h post-induction.

Figure 9:
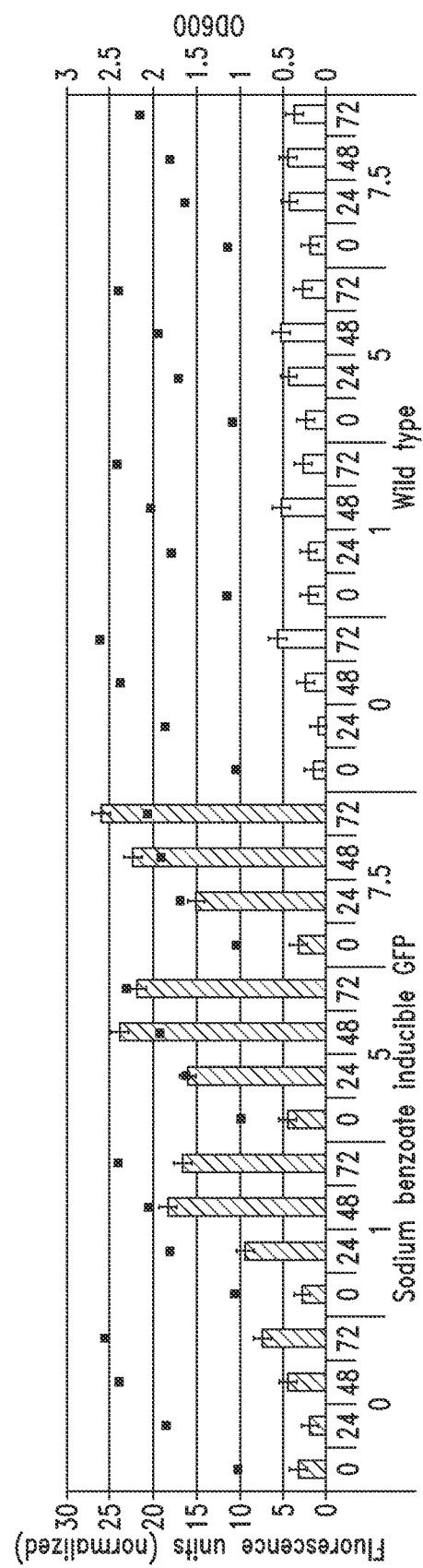
FIG. 9 is a graph showing normalized Dasher fluorescence intensity (bars, normalized to growth [squares] by optical density at 600 nm $OD_{600}$) with increasing sodium benzoate concentrations (1.0 mM to 7.5 mM) in *M. capsulatus* Bath containing a pCAL-B vector comprising a sodium benzoate inducible expression cassette operably linked to a nucleic acid molecule encoding the Dasher variant of GFP (pCAL-B-GFP, left) and in untransformed wild-type *M. capsulatus* Bath (right). The fluorescence intensities represent an average of triplicate samples.

FIG. 9 shows fluorescence intensities measured at 518 nm from both wild type Bath and Bath containing a pCAL-B-GFP vector and corresponding OD600 data pre-induction (0), and 24 h (24), 48 h (48), and 72 h (72) post-induction. All strains were grown in the presence of 0 mM, 1 mM, 5 mM, or 7.5 mM sodium benzoate. Fluorescence data were normalized by OD600 and represent an average of triplicate samples. The data revealed that no increase in fluorescence occurred up to 72 h post-induction when the wild type Bath strain was exposed to 1 mM, 5 mM, or 7.5 mM sodium benzoate. When the strain containing the sodium benzoate inducible GFP expression cassette was induced with 1 mM, 5 mM, or 7.5 mM sodium benzoate, fluorescence increased over time and with increasing sodium benzoate concentrations. At 72 h post-induction, the Bath containing a pCAL-B-GFP reached about 3-5 times higher fluorescence intensities than the un-induced strains (Table 2). Highest fluorescence intensities were reached 72 h post-induction in strains induced with 7.5 mM sodium benzoate. A control strain carrying an IPTG inducible promoter controlling GFP did not reveal any fluorescence signal above background levels when induced with 0 mM, 1 mM, 5 mM, or 7.5 mM sodium benzoate, indicating that the inducer is specific to Pben in *M. capsulatus* Bath (data not shown).

In summary, these data show that the sodium benzoate inducible promoter is functional in *M. capsulatus* Bath and that its response is specific to sodium benzoate. Furthermore, in the absence of induction the promoter is tightly turned off.

Example 4

3-Methylbenzoate Inducible Expression System

Figure 10:
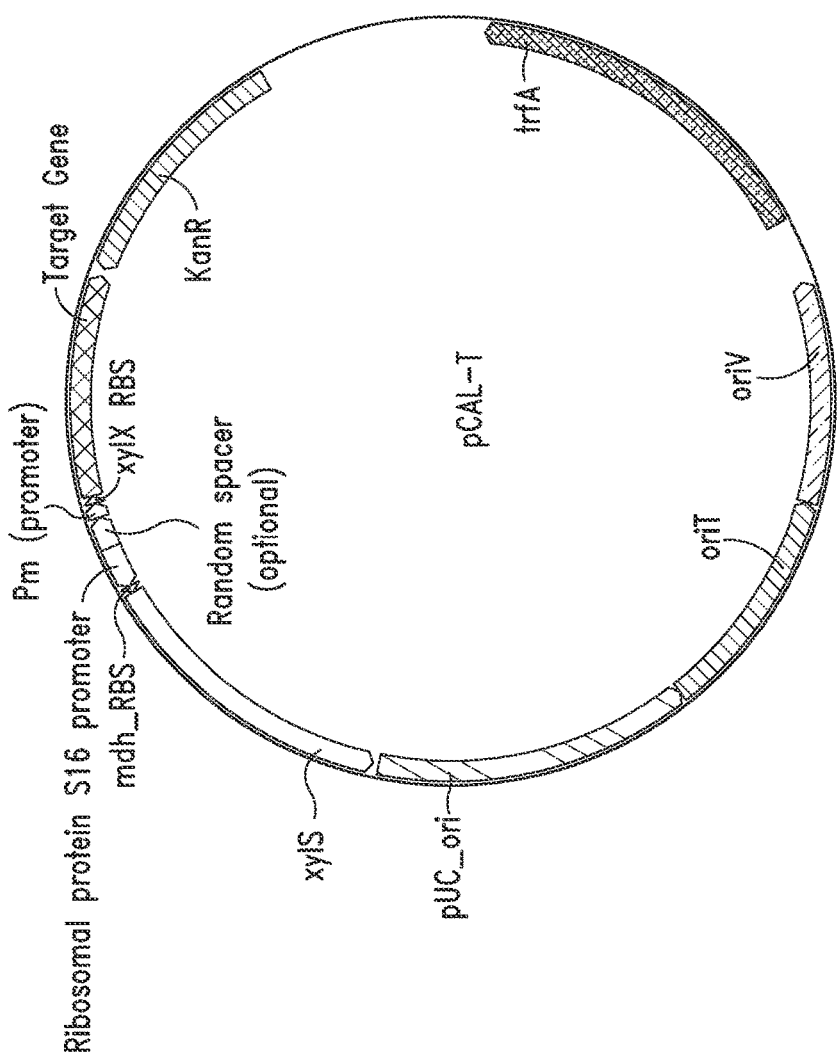
FIG. 10 is a schematic map of an exemplary vector (pCAL-T) containing a putative 3-methylbenzoate ("3 MB") inducible expression system.

A 3-methylbenzoate ("3 MB") inducible expression system for *M. capsulatus* Bath was designed by combining elements from the *Pseudomonas putida* mt-2 TOL plasmid pWW0 (Genbank accession number M15740.1) and a methanotroph-specific promoter. For this purpose two DNA fragments containing the following features were constructed via gene synthesis: 1) A codon optimized version of the xylS activator gene (SEQ ID NO.:51) under control of a constitutive methanotroph-specific ribosomal protein promoter and the MDH ribosomal binding site followed by a 100-bp random spacer downstream of the ribosomal protein promoter and 2) 62 bp region upstream of the xylX translation initiation start site (containing the putative xylX promoter and ribosomal binding site, SEQ ID NO.:52) downstream of the random spacer sequence. Fragment 1 was flanked by SpeI/MfeI restriction sites whereas fragment 2 was flanked by BsaI restrictions sites and in addition contained MfeI/SpeI restriction sites upstream of the xylX promoter. Subsequently fragment 2 was cloned into the promoter probe plasmid (same as described above) via BsaI sites such that GFP was controlled by the xylX promoter. In a second step fragment 1 was inserted upstream of the xylX promoter using the MfeI/SpeI sites yielding the plasmid pCAL-T shown in FIG. 10. A pCAL-T plasmid containing GFP (pCAL-T-GFP) was then introduced into *M. capsulatus* Bath by conjugation as described above in Example 2. The presence of the correct plasmid in *M. capsulatus* Bath was verified by PCR and sequencing.

Functionality of the 3 MB inducible expression system was assessed by testing strains for their ability to fluoresce when induced with 3 MB. For this purpose, the *M. capsulatus* Bath strain containing pCAL-T-GFP used to inoculate 2.5 mL MM-W1 media/well of 24-well plates supplemented with 15 μg/mL kanamycin. In parallel, a *M. capsulatus* Bath wild type strain serving as a negative control was used to inoculate 2.5 mL MM-W1 media/well of a 24-well plate. The plate headspace was flushed with a 1:1 mixture of oxygen and methane as the carbon source for *M. capsulatus* Bath, the plates were sealed and then shaken continuously at a rate of 200-250 rpm during incubation at 42° C. for a 24 hour pre-culture. Then, new 24-well plates containing 2.5 mL fresh MM-W1, and where necessary 15 μg/mL kanamy-cin, were inoculated with 0.25 mL of the pre-culture and incubated at 42° C. for 72 h. All strains were grown in four sets of triplicates, whereas three sets were induced 24 h post-transfer with 1, 5, or 7.5 mM 3 MB and the fourth set was left un-induced. $OD_{600}$ readings and fluorescence measurements (Excitation: 488 nm/Emission: 518 nm) were taken at induction, and 24 h, 48 h, and 72 h post-induction.

Figure 11:
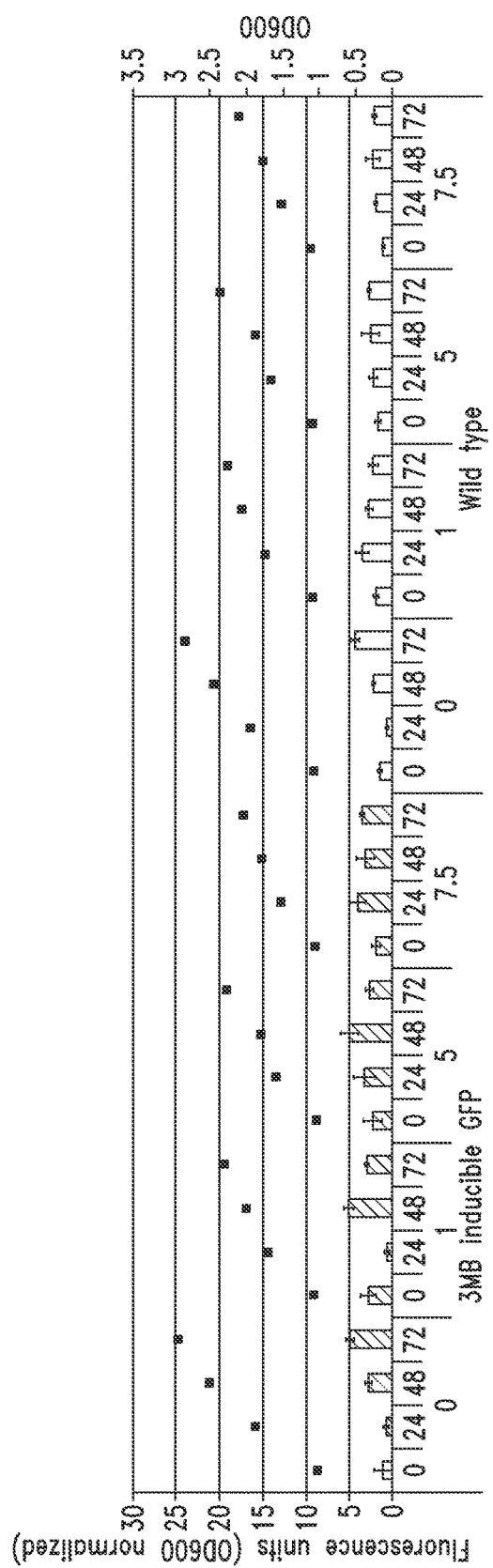
FIG. 11 is a graph showing Dasher fluorescence intensity (bars, normalized to growth [squares] by optical density at 600 nm $OD_{600}$) with increasing 3-methylbenzoate (3 MB) concentrations (1.0 mM to 7.5 mM) in *M. capsulatus* Bath containing a pCAL-T vector comprising a putative 3 MB inducible expression cassette operably linked to a nucleic acid molecule encoding the Dasher variant of GFP (pCAL-T-GFP, left) and in untransformed wild-type *M. capsulatus* Bath (right). The fluorescence intensities represent an average of triplicate samples.

FIG. 11 shows fluorescence intensities measured at 518 nm from both wild type Bath and Bath containing pCAL-T-GFP and corresponding OD600 data pre-induction (0), 24 h (24), 48 h (48), and 72 h (72) post-induction. All strains were grown in the presence of 0 mM, 1 mM, 5 mM, or 7.5 mM sodium benzoate. Fluorescence data were normalized by OD600 and represent an average of triplicate samples. The data revealed that no significant increase in fluorescence occurred up to 72 h post-induction when both the wild type Bath strain and the 3 MB inducible GFP expression strain (i.e., containing pCAL-T-GFP) were exposed to 1 mM, 5 mM, or 7.5 mM 3 MB (Table 2).

TABLE 2

Benzoate vs. 3MB inducibility in *M. capsulatus* Bath

| Strain | Fluorescense Intensity (Induced) | Fluorescense Intensity (Uninduced) | Metabolite Formation (Induced) | Metabolite Formation (Uninduced) |
|---|---|---|---|---|
| pCAL-B-GFP | ++ | − | | |
| pCAL-T-GFP | − | − | | |
| pCAL-B-ME (Metabolic Enzyme) | | | ++++ | +++++ |
| pCAL-B2-ME (Metabolic Enzyme) | | | ++++ | + |

These data show that, unlike the sodium benzoate inducible expression system of Example 2, the 3 MB inducible expression system is non-functional in *M. capsulatus* Bath.

Example 5

Improved Sodium Benzoate Inducible Expression System for *Methylococcus capsulatus* Bath The sodium benzoate inducible expression system described in Example 3 was further evaluated with an enzymatically active protein. For this purpose, the plasmid created in Example 3 was modified by replacing GFP with a metabolic enzyme, yielding the plasmid shown in FIG. 8. The pCAL-B-ME (Metabolic Enzyme) plasmid was then introduced into *M. capsulatus* Bath by conjugation as described in Example 3. The presence of the correct plasmid in *M. capsulatus* Bath was verified by PCR and sequencing.

Functionality of the sodium benzoate inducible expression system in conjunction with the metabolic enzyme (pCAL-B-ME) was assessed by testing strains for their ability to form the metabolite produced when the metabolic enzyme was expressed. For this purpose, the *M. capsulatus* Bath strain containing pCAL-B-ME was used to inoculate 2.5 mL MM-W1 media/well of 24-well plates supplemented with 15 μg/mL kanamycin. The plates were sealed and incubated at 42° C. while continuously fed with a 1:1 mixture of oxygen and methane as the carbon source. The plates were shaken at a rate of 300 rpm for 24 h (pre-culture). The total gas flow to the system was 100 mL/min corresponding to 25 mL/min to each tower. The plates were shaken continuously at 300 rpm on an 8 mm orbit for 24 h (pre-culture). Then, new 24-well plates containing 2.25 mL fresh MM-W1, were inoculated with 0.25 mL of the pre-culture and incubated at 42° C. for 72 h. All strains were grown in four sets of triplicates, whereas three sets were induced 24 h post-transfer with 0.5 mM, 1 mM, or 5 mM sodium benzoate and the fourth set was left un-induced. Post-induction (48 h) $OD_{600}$ readings of all cultures were taken and then evaluated for metabolite formation. All strains exhibited significant product formation even when no sodium benzoate was added to the culture. Comparable amounts of metabolite were formed under induced and un-induced conditions (Table 2). These data indicated that in the presence of an enzymatically active protein, the pCAL-B system showed some leakiness when no inducer was present. The observed leakiness might have been a consequence of transcriptional read-through from the ribosomal promoter controlling expression of benR, as no terminator was placed downstream of benR/upstream of $P_{ben}$.

To reduce the level of leakiness in un-induced cells, the pCAL-B plasmid was reconstructed. The plasmid fragment containing the ribosomal promoter, the MDH ribosomal binding sequence, and benR was relocated upstream of the KanR promoter/downstream of trfA and was oriented in such a way that read-through from all promoters was avoided, yielding plasmid pCAL-B2 shown in FIG. 12.

Functionality of this pCAL-B2 sodium benzoate inducible expression system was then assessed by testing strains for their ability to form a metabolite by adding a metabolic enzyme under the control the $P_{ben}$ promoter (pCAL-B2-ME). The pCAL-B2-ME plasmid containing a nucleic acid molecule encoding a metabolic enzyme was introduced into *M. capsulatus* Bath by conjugation as previously described in Example 3. The presence of the correct plasmid in *M. capsulatus* Bath was verified by PCR and sequencing.

An *M. capsulatus* Bath strain containing the pCAL-B2 sodium benzoate inducible expression cassette controlling expression of the metabolic enzyme (pCAL-B2-ME) was cultured under the same conditions described above for evaluating the first sodium benzoate inducible expression system (pCAL-B), except that strains were induced with much lower levels of sodium benzoate (0.05 mM, 0.1 mM, and 1 mM). Comparable concentrations of metabolite were formed when the strain containing the pCAL-B2 sodium benzoate inducible enzyme expression cassette was induced with 0.05 mM, 0.1 mM, and 0.5 mM of sodium benzoate. The strain containing the pCAL-B2-ME induced with 1 mM sodium benzoate formed approximately 25% less metabolite when compared to strains induced with 0.05 mM, 0.1 mM, and 0.5 mM of sodium benzoate. The strain containing the pCAL-B2-ME that was not induced formed 20-fold less metabolite than that same strain induced with 0.05 mM, 0.1 mM, and 0.5 mM of sodium benzoate (Table 2).

In summary, abolishing transcriptional read-through from the ribosomal protein promoter led to a sodium benzoate inducible expression system that was tightly turned off when no inducer was present. In addition, inducer concentrations as low as 0.05 mM sodium benzoate still led to maximum product formation with this system.

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification and/or listed in the Application Data Sheet, including but not limited to U.S. Provisional Patent Application No. 62/014,007 filed Jun. 18, 2014 and PCT Application No. PCT/US2015/036515 filed Jun. 18, 2015, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A non-naturally occurring nucleic acid molecule, comprising:
   (1) a promoter that is functional in a methanotrophic bacterium, and
   (2) an altered methanol dehydrogenase (MDH) or a native MDH ribosomal binding sequence, wherein the altered MDH ribosomal binding sequence comprises the polynucleotide sequence as set forth in any one of SEQ ID NOS.:20, 22, 24, 26, 27, 32, and 41;
   provided that when the promoter is an MDH gene promoter, the nucleic acid comprises an altered MDH ribosomal binding sequence.

2. The nucleic acid of claim 1, wherein the promoter is a constitutive promoter or an inducible promoter.

3. The nucleic acid of claim 1, comprising an altered MDH ribosomal binding sequence.

4. The nucleic acid of claim 3, wherein the promoter is an MDH promoter, 30S ribosomal protein S16 promoter, 30S ribosomal protein S12 promoter, 50S ribosomal protein L13 promoter, hexulose 6-phosphate synthase promoter, T5 promoter, or Trc promoter.

5. The nucleic acid of claim 4, wherein the MDH promoter comprises a promoter portion of SEQ ID NO.:14, the 30S ribosomal protein S16 promoter comprises a promoter portion of SEQ ID NO.:15, the 30S ribosomal protein S12 promoter comprises a promoter portion of SEQ ID NO.:43, the 50S ribosomal protein L13 promoter comprises a promoter portion of SEQ ID NO.:44, the hexulose 6-phosphate synthase promoter comprises a promoter portion of SEQ ID NO.:16, the T5 promoter comprises a promoter portion of SEQ ID NO.:17, and the Trc promoter comprises a promoter portion of SEQ ID NO.:18.

6. The nucleic acid of claim 4, further comprising a nucleic acid molecule encoding a target polypeptide operably linked to the promoter sequence and the ribosomal binding sequence.

7. The nucleic acid of claim 6, wherein the target polypeptide is a marker, a reporter protein, or a protein capable of improving production of a desired chemical or metabolite.

8. The nucleic acid of claim 7, wherein the target polypeptide is a crotonase, crotonyl CoA thioesterase, 4-oxalocrotonate decarboxylase, lactate dehydrogenase, or antibiotic resistance protein.

9. The nucleic acid of claim 7, wherein the target polypeptide is an amino acid biosynthesis enzyme, a fatty acid converting enzyme, a fatty acid elongation pathway enzyme, or a carbohydrate biosynthesis enzyme.

10. The nucleic acid of claim 9, wherein the amino acid biosynthesis enzyme is a lysine biosynthesis enzyme, a threonine biosynthesis enzyme, a methionine biosynthesis enzyme, or a cysteine biosynthesis enzyme.

11. The nucleic acid of claim 9, wherein the fatty acid converting enzyme is a fatty acyl-CoA reductase, a fatty alcohol forming acyl-ACP reductase, and/or a carboxylic acid reductase.

12. The nucleic acid of claim 9, wherein the fatty acid elongation pathway enzyme is a β-ketoacyl-CoA synthase, a β-ketoacyl-CoA reductase, a β-hydroxy acyl-CoA dehydratase, and/or an enoyl-CoA reductase.

13. The nucleic acid of claim 9, wherein the carbohydrate biosynthesis enzyme is a glucan synthase.

14. The nucleic acid of claim 6, wherein the target polypeptide is LacI repressor protein or a BenR activator protein.

15. The nucleic acid of claim 14, wherein the promoter is a 30S ribosomal protein S16 promoter.

16. The nucleic acid of claim 15, wherein the nucleic acid further comprises a second promoter, a lac operator to which LacI repressor protein is capable of binding, and a sequence encoding a second target polypeptide, wherein the second promoter and the lac operator are operably linked to the nucleic acid molecule encoding the second target polypeptide.

17. The nucleic acid of claim 16, wherein the second target polypeptide is a marker, a reporter protein, or a protein capable of improving production of a desired chemical or metabolite.

18. The nucleic acid of claim 17, wherein the second target polypeptide is a lactate dehydrogenase, crotonase, crotonyl CoA thioesterase, 4-oxalocrotonate decarboxylase, antibiotic resistance protein, amino acid biosynthesis enzyme, fatty acid converting enzyme, fatty acid elongation pathway enzyme, or carbohydrate biosynthesis enzyme.

19. The nucleic acid of claim 18, wherein the second promoter is an MDH promoter.

20. The nucleic acid of claim 19, further comprising a second ribosomal binding sequence, wherein the second ribosomal binding sequence comprises an altered or native methanol dehydrogenase (MDH) ribosomal binding sequence.

21. A vector, comprising the nucleic acid of claim 1.

22. A host cell, comprising the nucleic acid of claim 1.

23. The host cell of claim 22, wherein the host cell is *Methylococcus capsulatus* Bath, *Methylomonas* 16a, *Methylosinus trichosporium* OB3b, *Methylosinus sporium*, *Methylocystis parvus*, *Methylomonas methanica*, *Methylomonas albus*, *Methylobacter capsulatus*, *Methylobacterium organophilum*, *Methylomonas* sp AJ-3670, *Methylocella silvestris*, *Methylocella palustris*, *Methylocella tundrae*, *Methylocystis daltona* strain SB2, *Methylocystis bryophila*, *Methylocapsa aurea* KYG, *Methylacidiphilum infernorum*, *Methylacidiphilum fumariolicum*, *Methyloacida kamchatkensis*, *Methylibium petroleiphilum*, or *Methylomicrobium alcahphilum*.

24. The host cell of claim 22, wherein the host cell is *Methylococcus capsulatus* Bath or *Methylosinus trichosporium* OB3b.

* * * * *

SEQUENCE LISTING

```
<160> NUMBER OF SEQ ID NOS: 54

<210> SEQ ID NO 1
<211> LENGTH: 710
<212> TYPE: DNA
<213> ORGANISM: Artificial Sequence
<220> FEATURE:
<223> OTHER INFORMATION: minimal oriV (modified)

<400> SEQUENCE: 1
gctgccattt tgggggtgag gccgttcgcg gccgaggggc gcagccctg gggggatggg       60 aggcccgcgt tagcgggccg ggagggttcg agaaggggg gcacccccct tcggcgtgcg      120
cggtcacgcg cacagggcgc agccctggtt aaaaacaagg tttataaata ttggtttaaa    180
agcaggttaa aagacaggtt agcggtggcc gaaaaacggg cggaaaccct tgcaaatgct    240
ggattttctg cctgtggaca gcccctcaaa tgtcaatagg tgcgccctc atctgtcagc     300 actctgcccc tcaagtgtca aggatcgcgc ccctcatctg tcagtagtcg cgcccctcaa    360
gtgtcaatac cgcagggcac ttatcccag gcttgtccac atcatctgtg ggaaactcgc     420
```

```
gtaaaatcag gcgttttcgc cgatttgcga ggctggccag ctccacgtcg ccggccgaaa      480
tcgagcctgc ccctcatctg tcaacgccgc gccgggtgag tcggcccctc aagtgtcaac      540
gtccgcccct catctgtcag tgagggccaa gttttccgcg aggtatccac aacgccggcg      600
gccgcggtgt ctcgcacacg gcttcgacgg cgtttctggc gcgtttgcag gccatagac       660 ggccgccagc ccagcggcga gggcaaccag cccggtgagc gtcggaaagg                 710
```

<210> SEQ ID NO 2
<211> LENGTH: 1081
<212> TYPE: DNA
<213> ORGANISM: Artificial Sequence
<220> FEATURE:
<223> OTHER INFORMATION: oriV (modified)

<400> SEQUENCE: 2

```
tgacacttga ggggcgttta gagcgagcca ggaaagccga ccccctcctt ggagtaaaaa      60
cccttgcggc gttgcagccg gcacggatct tccgatcggg cgcggtggtg gccgcgtctg     120
tgacctaaaa agggggagt ccagagggc gcagccccctt gggcatagc gcagcgtaat      180 cggagacgta attgagcatt tccaggcgct tgcgcctggt caacgaaaga gtcagcgccg     240
taggcgctgc cattttggg gtgaggccgt tcgcggccga gggcgcagc ccctgggggg      300 atgggaggcc cgcgttagcg ggccgggagg gttcgagaag gggggcacc ccccttcggc      360 gtgcgcggtc acgcgcacag ggcgcagccc tggttaaaaa caaggtttat aaatattggt     420
ttaaaagcag gttaaaagac aggttagcgg tggccgaaaa acgggcggaa accccttgcaa     480 atgctggatt ttctgcctgt ggacagcccc tcaaatgtca ataggtgcgc ccctcatctg     540
tcagcactct gcccctcaag tgtcaaggat cgcgcccctc atctgtcagt agtcgcgccc     600
ctcaagtgtc aataccgcag ggcacttatc cccaggcttg tccacatcat ctgtgggaaa     660
ctcgcgtaaa atcaggcgtt ttcgccgatt tgcgaggctg gccagctcca cgtcgccggc     720
cgaaatcgag cctgccccctc atctgtcaac gccgcgccgg gtgagtcggc ccctcaagtg     780
tcaacgtccg ccctcatct gtcagtgagg gccaagtttt ccgcgaggta ccacaacgc      840 cggcggccgc ggtgtctcgc acacggcttc gacggcgttt ctggcgcgtt tgcagggcca     900
tagacggccg ccagcccagc ggcgagggca accagcccgg tgagcgtcgg aaaggcgctg     960
gaagccccgt agcgacgcgg agaggggcga gacaagccaa gggcgcaggc tcgatgcgca    1020
gcacgacata gccggttctc gcaaggacga gaatttccct gcggtgcccc tcaagtgtca    1080
a                                                                   1081
```

<210> SEQ ID NO 3
<211> LENGTH: 1146
<212> TYPE: DNA
<213> ORGANISM: Pseudomonas aeruginosa plasmid RK2

<400> SEQUENCE: 3

```
atgaatcgga cgtttgaccg gaaggcatac aggcaagaac tgatcgacgc ggggttttcc      60
gccgaggatg ccgaaaccat cgcaagccgc accgtcatgc gtgcgccccg cgaaaccttc     120
cagtccgtcg gctcgatggt ccagcaagct acggccaaga tcgagcgcga cagcgtgcaa     180
ctggctcccc ctgccctgcc cgcgccatcg gccgccgtgg agcgttcgcg tcgtctagaa     240
caggaggcgg caggtttggc gaagtcgatg accatcgaca cgcgaggaac tatgacgacc     300
aagaagcgaa aaaccgccgg cgaggacctg gcaaaacagg tcagcgaggc caagcaggcc     360
gcgttgctga acacacgaa gcagcagatc aaggaaatgc agctttcctt gttcgatatt     420
```

```
gcgccgtggc cggacacgat gcgagcgatg ccaaacgaca cggcccgctc tgccctgttc    480
accacgcgca acaagaaaat cccgcgcgag gcgctgcaaa acaaggtcat tttccacgtc    540
aacaaggacg tgaagatcac ctacaccggc gtcgagctgc gggccgacga tgacgaactg    600
gtgtggcagc aggtgttgga gtacgcgaag cgcaccccta tcggcgagcc gatcaccttc    660
acgttctacg agctttgcca ggacctgggc tggtcgatca atggccggta ttacacgaag    720
gccgaggaat gcctgtcgcg cctacaggcg acggcgatgg gcttcacgtc cgaccgcgtt    780
gggcacctgg aatcggtgtc gctgctgcac cgcttccgcg tcctggaccg tgcaagaaa    840 acgtcccgtt gccaggtcct gatcgacgag gaaatcgtcg tgctgtttgc tggcgaccac    900
tacacgaaat tcatatggga gaagtaccgc aagctgtcgc cgacggcccg acggatgttc    960
gactatttca gctcgcaccg ggagccgtac ccgctcaagc tggaaaacctt ccgcctcatg   1020 tgcggatcgg attccacccg cgtgaagaag tggcgcgagc aggtcggcga agcctgcgaa   1080
gagttgcgag cagcggcct ggtggaacac gcctgggtca atgatgacct ggtgcattgc   1140
aaacgc                                                               1146

<210> SEQ ID NO 4
<211> LENGTH: 178
<212> TYPE: DNA
<213> ORGANISM: Artificial Sequence
<220> FEATURE:
<223> OTHER INFORMATION: trfA promoter 1 (immediately upstream trfA in
      RK2)

<400> SEQUENCE: 4
attcgtgcag ggcaagattc ggaataccaa gtacgagaag gacggccaga cggtctacgg    60
gaccgacttc attgccgata aggtggatta tctggacacc aaggcaccag gcgggtcaaa   120
tcaggaataa gggcacattg ccccggcgtg agtcggggca atcccgcaag gagggtga    178

<210> SEQ ID NO 5
<211> LENGTH: 60
<212> TYPE: DNA
<213> ORGANISM: Artificial Sequence
<220> FEATURE:
<223> OTHER INFORMATION: trfA promoter 2 (the promoter from the trf
      operon in RK2)

<400> SEQUENCE: 5
ttgacagcgg aaccaatgtt tagctaaact agagtctcct ttctcaagga gactttcgat    60

<210> SEQ ID NO 6
<211> LENGTH: 201
<212> TYPE: DNA
<213> ORGANISM: Artificial Sequence
<220> FEATURE:
<223> OTHER INFORMATION: Pbla promoter

<400> SEQUENCE: 6
agacgaaagg gcctcgtgat acgcttattt ttataggtta atgtcatgat aataatggtt    60
tcttagacgt caggtggcac ttttcgggga aatgtgcgcg gaaccccctat ttgtttattt   120 ttctaaatac attcaaatat gtatccgctc atgagacaat aaccctgata aatgcttcaa   180
taatattgaa aaaggaagag t                                              201

<210> SEQ ID NO 7
<211> LENGTH: 170
<212> TYPE: DNA
```

<213> ORGANISM: Artificial Sequence
<220> FEATURE:
<223> OTHER INFORMATION: Pneo promoter

<400> SEQUENCE: 7

```
acagcaagcg aaccggaatt gccagctggc gcgccctctg gtaaggttgg gaagccctgc    60
aaagtaaact ggatggcttt cttgccgcca aggatctgat ggcgcagggg atcaagatcg   120
acggatcgat ccggggaatt aattccgggg caatcccgca aggagggtga              170
```

<210> SEQ ID NO 8
<211> LENGTH: 742
<212> TYPE: DNA
<213> ORGANISM: Artificial Sequence
<220> FEATURE:
<223> OTHER INFORMATION: minimal RK2 origin of transfer (oriT)

<400> SEQUENCE: 8

```
cttttccgct gcataaccct gcttcggggt cattatagcg attttttcgg tatatccatc    60
cttttcgca cgatatacag gattttgcca aagggttcgt gtagactttc cttggtgtat   120
ccaacggcgt cagccgggca ggataggtga agtaggccca cccgcgagcg ggtgttcctt   180
cttcactgtc ccttattcgc acctggcggt gctcaacggg aatcctgctc tgcgaggctg   240
gccggctacc gccggcgtaa cagatgaggg caagcggatg ctgatgaaa ccaagccaac   300
caggaagggc agcccaccta tcaaggtgta ctgccttcca gacgaacgaa gagcgattga   360
ggaaaaggcg gcggcggccg gcatgagcct gtaggcctac ctgctggccg tcggccaggg   420
ctacaaaatc acgggcgtcg tggactatga gcacgtccgc gagctggccc gcatcaatgg   480
cgacctgggc cgcctgggcg gcctgctgaa actctggctc accgacgacc cgcgcacggc   540
gcggttcggt gatgccacga tcctcgccct gctggcgaag atcgaagaga agcaggacga   600
gcttggcaag gtcatgatgg gcgtggtccg cccgagggca gagccatgac tttttttagcc   660
gctaaaacgg ccgggggtg cgcgtgattg ccaagcacgt ccccatgcgc tccatcaaga   720
agagcgactt cgcggagctg gt                                          742
```

<210> SEQ ID NO 9
<211> LENGTH: 671
<212> TYPE: DNA
<213> ORGANISM: Artificial Sequence
<220> FEATURE:
<223> OTHER INFORMATION: kanamycin resistance cassette promoter

<400> SEQUENCE: 9

```
ggccttgtgg ggtcagttcc ggctgggggt tcagcagcca gcgctttact ggcatttcag    60
gaacaagcgg gcactgctcg acgcacttgc ttcgctcagt atcgctcggg acgcacggcg   120
cgctctacga actgccgata aacagaggat taaaattgac aattctaggg cgcgtatagc   180
ttgccggaag tcgccttgac ccgcatggca taggcctatc gtttccacga tcagcgatcg   240
gctcgttgcc ctgcgccgct ccaaagcccg cgacgcagcg ccggcaggca gagcaagtag   300
agggcagcgc ctgcaatcca tgcccacccg ttccacgttg ttatagaagc cgcatagatc   360
gccgtgaaga ggaggggtcc gacgatcgag gtcaggctgg tgagcgccgc cagtgagcct   420
tgcagctgcc cctgacgttc ctcatccacc tgcctggaca acattgcttg cagcgccggc   480
attccgatgc cacccgaagc aagcaggacc atgatcggga acgccatcca tccccgtgtc   540
ggacctgcag ggggggggg gaaagccacg ttgtgtctca aaatctctga tgttacattg   600
cacaagataa aaatatatca tcatgaacaa taaaaactgtc tgcttacata aacagtaata   660
```

-continued

```
caagggggtgt t                                                       671

<210> SEQ ID NO 10
<211> LENGTH: 807
<212> TYPE: DNA
<213> ORGANISM: Artificial Sequence
<220> FEATURE:
<223> OTHER INFORMATION: kanamycin resistance cassette coding sequence

<400> SEQUENCE: 10
atgagccata ttcaacggga aacgtcgagg ccgcgattaa attccaacat ggatgctgat      60
ttatatgggt ataaatgggc tcgcgataat gtcgggcaat caggtgcgac aatctatcgc     120
ttgtatggga agcccgatgc gccagagttg tttctgaaac atggcaaagg tagcgttgcc     180
aatgatgtta cagatgagat ggtcagacta aactggctga cggaatttat gccacttccg     240
accatcaagc attttatccg tactcctgat gatgcatggt tactcaccac tgcgatcccc     300
ggaaaaacag cgttccaggt attagaagaa tatcctgatt caggtgaaaa tattgttgat     360
gcgctggcag tgttcctgcg ccggttgcac tcgattcctg tttgtaattg tccttttaac     420
agcgatcgcg tatttcgcct cgctcaggcg caatcacgaa tgaataacgg tttggttgat     480
gcgagtgatt ttgatgacga gcgtaatggc tggcctgttg aacaagtctg gaaagaaatg     540
cataaacttt tgccattctc accggattca gtcgtcactc atggtgattt ctcacttgat     600
aaccttattt ttgacgaggg gaaattaata ggttgtattg atgttggacg agtcggaatc     660
gcagaccgat accaggatct tgccatccta tggaactgcc tcggtgagtt ttctccttca     720
ttacagaaac ggcttttttca aaaatatggt attgataatc ctgatatgaa taaattgcag     780
tttcatttga tgctcgatga gttttttc                                        807

<210> SEQ ID NO 11
<211> LENGTH: 422
<212> TYPE: DNA
<213> ORGANISM: Artificial Sequence
<220> FEATURE:
<223> OTHER INFORMATION: promoter of Kanamycin resistance cassette from
      RK2

<400> SEQUENCE: 11
ttgacaacgt gcctggatct ggctacacta tgcggccacc aagctcgccc gtggcgagct      60
ttacgaagcg atcggcatgc tcggtttctt ccgtgagcaa gtgttaggac ctttgctcta     120
ccgtcgcgct ggaaaggacc agcgcggagt gaggcgattg gaaacccttc gactggatga     180
agagcgcaga ctagccacca ccattgcgct gcacgatgcg ttgtctgtca gggatgccat     240
caaagcatct gcctccatct atctcgacct ccgagccgcc gatccgtcgt ggaaccgac     300 aacgcatatg ccaggtcttc tgtacgactt aatagaacgt gcggtaccag gcacgcctaa     360
ccgtcagtga gattggatga gtgaacgata ttgatcgaga agagccctgc gcagccgctg     420
cc                                                                    422

<210> SEQ ID NO 12
<211> LENGTH: 822
<212> TYPE: DNA
<213> ORGANISM: Pseudomonas aeruginosa plasmid RK2

<400> SEQUENCE: 12
gtgcccgaga gcatggcggc tcacgtgatg ggatacaaat gggcgcgtga taaggttggt      60
cagtccggct gcgcggtcta tcggctgcat agcaagtcag gcggctccga cttgtttctg     120
```

```
aagcacggca aagatgcttt tgccgacgac gtgactgatg aaatggtgag attgcgttgg    180 ctggcgggc acatttctgt gccctccgtt gtaagcttcg ttcgcacgcc caatcaggca    240
tggctcctga caacagcaat acatggaaaa acggcatatc aagtgctgaa atcggatttc    300
ggagcccgtc tcgttgttgt tgacgcattg gcggcgttca tgcgccgact gcatgcgatc    360
ccagtgagcg aatgctcctt caacagtgac cacgcatgca ggcttgcccg agcgcgggag    420
cgtatcgagg cggggttgt tgatgtcgat gacttcgata aggagcgcga agggtggacg    480
gccgaacagg tttgggaggc gatgcatcgc ctcctaccgc tcgcgccgga cccagtcgtg    540
acgcacggcg attttcact cgataatcta cttatcgtcg aaggtaaggt agtcggctgc    600
atcgacgttg gcgggctgg tattgctgat cgataccaag accttgccgt gttatggaac    660
tgtcttgagg agttcgaacc ttcgcttcag gagaggcttg ttgcgcaata tggcattgcc    720
gatccggata ggcgcaagct gcaatttcat ctcctgctgg acgaactttt ctaaggcgat    780
gccccctcga cctcgatcag ggaggcgttc aggacgactc ac                       822

<210> SEQ ID NO 13
<211> LENGTH: 1014
<212> TYPE: DNA
<213> ORGANISM: Artificial Sequence
<220> FEATURE:
<223> OTHER INFORMATION: pUC origin of replication

<400> SEQUENCE: 13
tacgctgact tgacgggacg gcgcaagctc atgaccaaaa tcccttaacg tgagttacgc     60
gcgcgtcgtt ccactgagcg tcagaccccg tagaaaagat caaaggatct tcttgagatc    120 cttttttct gcgcgtaatc tgctgcttgc aaacaaaaaa accaccgcta ccagcggtgg    180
tttgtttgcc ggatcaagag ctaccaactc ttttccgaa ggtaactggc ttcagcagag    240
cgcagatacc aaatactgtt cttctagtgt agccgtagtt agcccaccac ttcaagaact    300
ctgtagcacc gcctacatac ctcgctctgc taatcctgtt accagtggct gctgccagtg    360
gcgataagtc gtgtcttacc gggttggact caagacgata gttaccggat aaggcgcagc    420
ggtcgggctg aacggggggt tcgtgcacac agcccagctt ggagcgaacg acctacaccg    480
aactgagata cctacagcgt gagctatgag aaagcgccac gcttcccgaa gggagaaagg    540
cggacaggta tccggtaagc ggcagggtcg aacaggaga gcgcacgagg gagcttccag    600
ggggaaacgc ctggtatctt tatagtcctg tcgggtttcg ccacctctga cttgagcgtc    660
gatttttgtg atgctcgtca ggggggcgga gcctatggaa aaacgccagc aacgcggcct    720
ttttacggtt cctggccttt tgctggcctt ttgctcacat gttctttcct gcgttatccc    780
ctgattctgt ggataaccgt attaccgcct ttgagtgagc tgataccgct cgccgcagcc    840
gaacgaccga gcgcagcgag tcagtgagcg aggaagcgga aggcgagagt agggaactgc    900
caggcatcaa actaagcaga aggccctga cggatgcct ttttgcgttt ctacaaactc     960
tttctgtgtt gtaaaacgac ggccagtctt aagctcgggc cccctgggcg gttc          1014

<210> SEQ ID NO 14
<211> LENGTH: 229
<212> TYPE: DNA
<213> ORGANISM: Artificial Sequence
<220> FEATURE:
<223> OTHER INFORMATION: putative methanol dehydrogenase (MDH), large
      subunit (MCA0779) promoter with native RBS and
      spacer
```

```
<400> SEQUENCE: 14
tttgcctcga tcggcggtcc ttgtgacagg gagatattcc cgacggatcc ggggcattcg    60
agcggaaccg cccgccgtgg gagttttcc agcgagcatt cgagagtttt tcaaggcggc   120
ttcgaggggt tattccgtaa cgccgccgac atgatctgtc ccagaatctc cgccgctgtt   180
cgtagagcgc cgatgcaggg tcggcatcaa tcattcttgg aggagacac               229

<210> SEQ ID NO 15
<211> LENGTH: 150
<212> TYPE: DNA
<213> ORGANISM: Artificial Sequence
<220> FEATURE:
<223> OTHER INFORMATION: putative 30S ribosomal protein S16 (MCA0392)
      promoter with native RBS and spacer

<400> SEQUENCE: 15
gttcaggata agcccggtgc cggatggcga ccgggttttt cttttcaacc ctggtgcttc    60
ccagtggggc aagacggcag ggcttcacaa ttactcagga tcgcatacaa tacgcgtttt   120
tatccgtacg gtttgactag aggcacaggc                                    150

<210> SEQ ID NO 16
<211> LENGTH: 497
<212> TYPE: DNA
<213> ORGANISM: Artificial Sequence
<220> FEATURE:
<223> OTHER INFORMATION: putative hexulose 6-phosphate synthase promoter
      from Methylomonas 16a with native RBS and spacer

<400> SEQUENCE: 16
ttcggaatcc ctgacgggaa ttggcccgaa gaaggcagat gccatcgttc agtatcgaaa    60
ggaacatggg gattttcagt cattgaagga tctggagaat gtcagcggca ttggcgagaa   120
aacccttcag gccaatgaaa aagacattcg cttcacggat gatttgagcg ataagtcatc   180
cgcggaaaaa ggtgcggtag ctgtggataa aaaaggcgcc agatagtaag cgctaaggat   240
tggggtgcgt cgccggtcgc ggcggcgctc ctcgacggca gagttggtgc caggttggcg   300
gatgattgat gccgaatatt acgcgaccaa ttctcgaggc aaatgaactg tgagctactg   360
agttgcaggc attgacagcc atcccatttc tatcatacag ttacggacgc atcacgagta   420
ggtgataagc ctagcagatt gcggcagttg gcaaaatcag ctattactaa taattaaaaa   480
ctttcggagc acatcac                                                  497

<210> SEQ ID NO 17
<211> LENGTH: 48
<212> TYPE: DNA
<213> ORGANISM: Artificial Sequence
<220> FEATURE:
<223> OTHER INFORMATION: T5 promoter

<400> SEQUENCE: 17
aaatcatgaa aaatttattt gctttgtgag cggataacaa ttataata                 48

<210> SEQ ID NO 18
<211> LENGTH: 89
<212> TYPE: DNA
<213> ORGANISM: Artificial Sequence
<220> FEATURE:
<223> OTHER INFORMATION: trc promoter

<400> SEQUENCE: 18
attctgaaat gagctgttga caattaatca tccggctcgt ataacggata acaattcccc    60
```

```
tctagaaata attttgttta actttaaga                                       89

<210> SEQ ID NO 19
<211> LENGTH: 256
<212> TYPE: DNA
<213> ORGANISM: Artificial Sequence
<220> FEATURE:
<223> OTHER INFORMATION: putative MDH, large subunit (MCA0779) promoter
      linked to a variant MDH ribosome binding site
      (RBS_1.0) with variant and modified spacer

<400> SEQUENCE: 19
ggtctccttt ttcgtcttcg aattctttgc ctcgatcggc ggtccttgtg acagggagat    60
attcccgacg gatccggggc attcgagcgg aaccgcccgc cgtgggagtt tttccagcga   120
gcattcgaga gttttttcaag gcggcttcga ggggttattc cgtaacgccg ccgacatgat  180
ctgtcccaga atctccgccg ctgttcgtag agcgccgatg cagggtcggc atcaatcatt   240
ctaaggaggt aaaaaa                                                   256

<210> SEQ ID NO 20
<211> LENGTH: 14
<212> TYPE: DNA
<213> ORGANISM: Artificial Sequence
<220> FEATURE:
<223> OTHER INFORMATION: variant MDH, large subunit (MCA0779) RBS
      (RBS_1.0) with variant and modified spacer

<400> SEQUENCE: 20
aaggaggtaa aaaa                                                      14

<210> SEQ ID NO 21
<211> LENGTH: 256
<212> TYPE: DNA
<213> ORGANISM: Artificial Sequence
<220> FEATURE:
<223> OTHER INFORMATION: putative MDH, large subunit (MCA0779) promoter
      linked to a variant MDH ribosome binding site
      (RBS_0.6) with variant and modified spacer

<400> SEQUENCE: 21
ggtctccttt ttcgtcttcg aattctttgc ctcgatcggc ggtccttgtg acagggagat    60
attcccgacg gatccggggc attcgagcgg aaccgcccgc cgtgggagtt tttccagcga   120
gcattcgaga gttttttcaag gcggcttcga ggggttattc cgtaacgccg ccgacatgat  180
ctgtcccaga atctccgccg ctgttcgtag agcgccgatg cagggtcggc atcaatcatt   240
ctatggtgga aaaaaa                                                   256

<210> SEQ ID NO 22
<211> LENGTH: 14
<212> TYPE: DNA
<213> ORGANISM: Artificial Sequence
<220> FEATURE:
<223> OTHER INFORMATION: variant MDH, large subunit (MCA0779) RBS
      (RBS_0.6) with variant and modified spacer

<400> SEQUENCE: 22
atggtggaaa aaaa                                                      14

<210> SEQ ID NO 23
<211> LENGTH: 263
<212> TYPE: DNA
<213> ORGANISM: Artificial Sequence
<220> FEATURE:
```

<223> OTHER INFORMATION: putative MDH, large subunit (MCA0779) promoter
    linked to variant MDH ribosome binding site
    (RBS_0.15) with variant and modified spacer

<400> SEQUENCE: 23
ggtctccttt tcgtcttcg aattctttgc ctcgatcggc ggtccttgtg acagggagat    60
attcccgacg gatccggggc attcgagcgg aaccgcccgc cgtgggagtt tttccagcga   120
gcattcgaga gttttcaag gcggcttcga ggggttattc cgtaacgccg ccgacatgat    180
ctgtcccaga atctccgccg ctgttcgtag agcgccgatg cagggtcggc atcaatcatt   240
ctatggatgt aaaaaataaa aaa                                           263

<210> SEQ ID NO 24
<211> LENGTH: 21
<212> TYPE: DNA
<213> ORGANISM: Artificial Sequence
<220> FEATURE:
<223> OTHER INFORMATION: modified MDH, large subunit (MCA0779) RBS
    (RBS_0.15) with variant and modified spacer

<400> SEQUENCE: 24
atggatgtaa aaataaaaa a                                              21

<210> SEQ ID NO 25
<211> LENGTH: 263
<212> TYPE: DNA
<213> ORGANISM: Artificial Sequence
<220> FEATURE:
<223> OTHER INFORMATION: putative MDH, large subunit (MCA0779) promoter
    linked to variant MDH ribosome binding site
    (RBS_0.1) with variant and modified spacer

<400> SEQUENCE: 25
ggtctccttt tcgtcttcg aattctttgc ctcgatcggc ggtccttgtg acagggagat    60
attcccgacg gatccggggc attcgagcgg aaccgcccgc cgtgggagtt tttccagcga   120
gcattcgaga gttttcaag gcggcttcga ggggttattc cgtaacgccg ccgacatgat    180
ctgtcccaga atctccgccg ctgttcgtag agcgccgatg cagggtcggc atcaatcatt   240
ctattgtggt aaaaaataaa aaa                                           263

<210> SEQ ID NO 26
<211> LENGTH: 21
<212> TYPE: DNA
<213> ORGANISM: Artificial Sequence
<220> FEATURE:
<223> OTHER INFORMATION: modified MDH, large subunit (MCA0779) RBS
    (RBS_0.1) with variant and modified spacer

<400> SEQUENCE: 26
attgtggtaa aaataaaaa a                                              21

<210> SEQ ID NO 27
<211> LENGTH: 11
<212> TYPE: DNA
<213> ORGANISM: Artificial Sequence
<220> FEATURE:
<223> OTHER INFORMATION: putative native MDH, large subunit (MCA0779)
    ribosome binding site with modified spacer

<400> SEQUENCE: 27
tggaggagac a                                                        11

<210> SEQ ID NO 28

<211> LENGTH: 151
<212> TYPE: DNA
<213> ORGANISM: Artificial Sequence
<220> FEATURE:
<223> OTHER INFORMATION: putative 30S ribosomal protein S16 (MCA0392)
      promoter linked to native MDH, large subunit
      (MCA0779) ribosome binding site with modified
      spacer

<400> SEQUENCE: 28

```
gttcaggata agcccggtgc cggatggcga ccgggttttt cttttcaacc ctggtgcttc    60
ccagtggggc aagacggcag ggcttcacaa ttactcagga tcgcatacaa tacgcgtttt   120
tatccgtacg gtttgactag tggaggagac a                                  151
```

<210> SEQ ID NO 29
<211> LENGTH: 496
<212> TYPE: DNA
<213> ORGANISM: Artificial Sequence
<220> FEATURE:
<223> OTHER INFORMATION: putative hexulose 6-phosphate synthase promoter
      from Methylomonas 16a linked to native MDH, large
      subunit (MCA0779) ribosome binding site with
      modified spacer

<400> SEQUENCE: 29

```
ttcggaatcc ctgacgggaa ttggcccgaa gaaggcagat gccatcgttc agtatcgaaa    60
ggaacatggg gattttcagt cattgaagga tctggagaat gtcagcggca ttggcgagaa   120
aacccttcag gccaatgaaa aagacattcg cttcacggat gatttgagcg ataagtcatc   180
cgcggaaaaa ggtgcggtag ctgtggataa aaaaggcgcc agatagtaag cgctaaggat   240
tggggtgcgt cgccggtcgc ggcggcgctc ctcgacggca gagttggtgc caggttggcg   300
gatgattgat gccgaatatt acgcgaccaa ttctcgaggc aaatgaactg tgagctactg   360
agttgcaggc attgacagcc atcccatttc tatcatacag ttacggacgc atcacgagta   420
ggtgataagc ctagcagatt gcggcagttg caaaatcag ctattactaa taattaaaaa    480
ctttctggag gagaca                                                   496
```

<210> SEQ ID NO 30
<211> LENGTH: 695
<212> TYPE: DNA
<213> ORGANISM: Artificial Sequence
<220> FEATURE:
<223> OTHER INFORMATION: moxF (MDH, large subunit) promoter from
      Methylomonas 16a linked to native MDH, large
      subunit (MCA0779) ribosome binding site with
      modified spacer

<400> SEQUENCE: 30

```
gcgccgtatg ctttcgaatc cgccaagacc gggcatggat aaatccatga ccaccacatc    60
gggcaattgc tttgaataga gttggcaagc ggtctcgcca cgatcggctt catagatctc   120
gccgatacga tccgacagcg atagataggt cttgtagccg gtacgaacca cggcgtgatc   180
atctaccaat aaaacgctga ttttactcgc cactggaaaa tttcctcctc aggtcgtcaa   240
gggataaaga tatgggacaa gtccagtctg atgccaggcg gacttggtgt gccttttttt   300
atgatgacgc tttatccgtg cttaaaccat gggagctttt cccgtttcca atttcgatcc   360
ttggcgagat aggaatattt ccgtgcatga ttgcgtcgat ttcacatcga tttcatggat   420
tgttccgtaa cgttagccag cccggcttct ataacatttg cgccagcgtg gcctggtggt   480
cggtaacccg tgatgcggtt atgatcaaca aagctggttt tcaacgacta attctgatct   540
```

```
tcaggtcgcg cctcacttat agcgataaaa atcctggagg aaacatgcaa caactcgatt    600
tgcgcatagt cgggaaaacc gcggccttgt tggctggtgg ccttctgagc gtggcgcaac    660
ccgcatcggc gaacaaggag ctggtggagg agaca                              695
```

<210> SEQ ID NO 31
<211> LENGTH: 1235
<212> TYPE: DNA
<213> ORGANISM: Artificial Sequence
<220> FEATURE:
<223> OTHER INFORMATION: construct having 30S ribosomal protein S16
      promoter, modified MDH ribosomal binding
      sequence, and variant lacI CDS

<400> SEQUENCE: 31

```
gttcaggata agcccggtgc cggatggcga ccgggttttt cttttcaacc ctggtgcttc    60
ccagtggggc aagacggcag ggcttcacaa ttactcagga tcgcatacaa tacgcgtttt    120
tatccgtacg gtttgactag tggaggagac atatgaaacc agtgactttg tacgatgtag    180
cggaatatgc aggcgtaagc taccagactg tgtcccgtgt cgttaaccaa gccagccacg    240
tgagcgcgaa aacgcgcgag aaggttgagg cagcaatggc ggaactgaat tacattccga    300
accgtgttgc tcaacagttg gccggcaagc agagcctgct gattggcgtt gcgacctcta    360
gcctggcgct gcacgcgagc agccaaatcg tggcagcgat taagtctcgt gcggatcaac    420
tgggtgcgag cgtcgtggtg agcatggtgg aacgtagcgg tgtcgaggct tgtaaagcgg    480
cagttcacaa tctgctggcc cagcgtgtca gcggcctgat tatcaattac ccgctggacg    540
accaggacgc aatcgctgtt gaggcggctt gcacgaatgt cccagcactg ttcttggacg    600
ttagcgatca gaccccgatt aactccatca tcttctccca tgaggacggc acccgcctgg    660
gcgtcgaaca tctggttgcg ctgggtcatc agcagatcgc gctgttggcg ggtccgttga    720
gcagcgtgag cgcgcgtctg cgtctggcgg gctggcacaa atatctgacg cgcaaccaaa    780
tccagcctat tgcggagcgc gaaggtgatt ggagcgcaat gtctggcttt cagcaaacga    840
tgcagatgct gaatgaaggt attgttccga ccgcgatgct ggttgttaac gatcagatgg    900
ccctgggtgc gatgcgtgca atcaccgaga gcggcctgcg cgttggtgcc gacatttccg    960
tcgtcggtta tgacgacacc gaggatagct cttgctacat cccaccgctg accaccatta    1020
aacaagattt tcgtctgctg ggtcaaacca gcgtcgatcg cctgctgcaa ttgtcgcagg    1080
gtcaggccgt gaaaggtaat caactgctgc cggtgagcct ggttaagcgt aagacgacgt    1140
tggcaccgaa cacccaaacc gcaagcccgc gtgtctctgg cgacagcctg atgcaactgg    1200
cgcgtcaagt gtcgcgcctg gaaagcggtc agtaa                              1235
```

<210> SEQ ID NO 32
<211> LENGTH: 12
<212> TYPE: DNA
<213> ORGANISM: Artificial Sequence
<220> FEATURE:
<223> OTHER INFORMATION: native MDH, large subunit (MCA0779) ribosome
      binding site with variant spacer (of SEQ ID NO:31)

<400> SEQUENCE: 32

```
tggaggagac at                                                        12
```

<210> SEQ ID NO 33
<211> LENGTH: 1083
<212> TYPE: DNA
<213> ORGANISM: Artificial Sequence
<220> FEATURE:

<223> OTHER INFORMATION: coding sequence of variant lacI (of SEQ ID
NO:31)

<400> SEQUENCE: 33

```
atgaaaccag tgactttgta cgatgtagcg gaatatgcag gcgtaagcta ccagactgtg      60
tcccgtgtcg ttaaccaagc cagccacgtg agcgcgaaaa cgcgcgagaa ggttgaggca     120
gcaatggcgg aactgaatta cattccgaac cgtgttgctc aacagttggc cggcaagcag     180
agcctgctga ttggcgttgc gacctctagc ctggcgctgc acgcgagcag ccaaatcgtg     240
gcagcgatta agtctcgtgc ggatcaactg ggtgcgagcg tcgtggtgag catggtggaa     300
cgtagcggtg tcgaggcttg taaagcggca gttcacaatc tgctggccca gcgtgtcagc     360
ggcctgatta tcaattaccc gctggacgac caggacgcaa tcgctgttga ggcggcttgc     420
acgaatgtcc cagcactgtt cttggacgtt agcgatcaga ccccgattaa ctccatcatc     480
ttctcccatg aggacggcac ccgcctgggc gtcgaacatc tggttgcgct gggtcatcag     540
cagatcgcgc tgttggcggg tccgttgagc agcgtgagcg cgcgtctgcg tctggcgggc     600
tggcacaaat atctgacgcg caaccaaatc cagcctattg cggagcgcga aggtgattgg     660
agcgcaatgt ctggctttca gcaaacgatg cagatgctga atgaaggtat tgttccgacc     720
gcgatgctgg ttgttaacga tcagatggcc ctgggtgcga tgcgtgcaat caccgagagc     780
ggcctgcgcg ttggtgccga catttccgtc gtcggttatg acgacaccga ggatagctct     840
tgctacatcc caccgctgac caccattaaa caagattttc gtctgctggg tcaaaccagc     900
gtcgatcgcc tgctgcaatt gtcgcagggt caggccgtga aggtaatca actgctgccg     960
gtgagcctgg ttaagcgtaa gacgacgttg gcaccgaaca cccaaaccgc aagcccgcgt    1020
gctctggccg acagcctgat gcaactggcg cgtcaagtgt cgcgcctgga aagcggtcag    1080
taa                                                                  1083
```

<210> SEQ ID NO 34
<211> LENGTH: 1031
<212> TYPE: DNA
<213> ORGANISM: Artificial Sequence
<220> FEATURE:
<223> OTHER INFORMATION: construct having first lacO (lacO1), putative
MDH promoter, second lacO (lacO2), untranslated region,
altered MDH ribosomal binding sequence, and Dasher
green fluorescent protein CDS

<400> SEQUENCE: 34

```
aattgtgagc ggataacaat ttttgcctcg atcggcggtc cttgtgacag ggagatattc      60
ccgacggatc cggggcattc gagcggaacc gcccgccgtg ggagtttttc cagcgagcat     120
tcgagagttt ttcaaggcgg cttcgagggg ttattccgta acgccgccga catgatctgt     180
cccagaatct ccgccgctgt tcgtagagcg ccgatgcagg gtcggcatca atcattcttg     240
gtgtggaatt gtgagcgctc acaattccac aacggtttcc ctctagaaat aattttgttt     300
aactttttgg aggagacaca atgacggcat tgactgaagg cgcaaaactg ttcgagaaag     360
aaatccccta catcaccgaa ctcgagggcg acgtagaggg catgaagttc atcatcaagg     420
gcgagggaac gggcgacgcc accaccggca ccatcaaggc gaagtatatc tgcaccacgg     480
gagatctgcc ggttccctgg gcgacgctgg tgtcgacctt gtcctacggc gtccaatgct     540
tcgcgaagta ccccagtcac atcaaagact tctttaagag cgccatgcca gaaggctaca     600
cgcaggaacg gaccatctcg ttcgaagggg atggggtcta caagaccccgt gcgatggtga     660
cgtacgagcg cgggtccatc tacaaccggg tcactctgac cggtgagaac ttcaagaagg    720
```

```
acggccacat tctgcgcaag aacgtcgcct tccagtgtcc gccgtcgatc ctgtatatcc    780
tgccggatac cgtgaacaac ggtattcgcg tggaattcaa tcaggcctat gatatcgagg    840
gtgtcacgga gaagcttgtg accaaatgca gccagatgaa tcgccctctg ccggctccg    900 ccgctgtcca tcccgcgg taccaccata tcacctatca taccaagctc agcaaagacc    960
gcgacgagag gcgggaccac atgtgcctcg tggaagtggt gaaggccgtc gacctggaca   1020
cctatcagtg a                                                        1031

<210> SEQ ID NO 35
<211> LENGTH: 21
<212> TYPE: DNA
<213> ORGANISM: Artificial Sequence
<220> FEATURE:
<223> OTHER INFORMATION: first lacO sequence (lacO1) (in bold in SEQ ID
      NO:34)

<400> SEQUENCE: 35
aattgtgagc ggataacaat t                                              21

<210> SEQ ID NO 36
<211> LENGTH: 220
<212> TYPE: DNA
<213> ORGANISM: Artificial Sequence
<220> FEATURE:
<223> OTHER INFORMATION: putative MDH, large subunit (MCA0779) promoter
      of SEQ ID NO:34. The last 3 nucleotides are a 5'
      portion of native ribosome binding site.

<400> SEQUENCE: 36
tttgcctcga tcggcggtcc ttgtgacagg gagatattcc cgacggatcc ggggcattcg    60
agcggaaccg cccgccgtgg gagtttttcc agcgagcatt cgagagtttt tcaaggcggc   120 ttcgagggt tattccgtaa cgccgccgac atgatctgtc ccagaatctc gccgctgtt    180 cgtagagcgc cgatgcaggg tcggcatcaa tcattcttgg                         220

<210> SEQ ID NO 37
<211> LENGTH: 30
<212> TYPE: DNA
<213> ORGANISM: Artificial Sequence
<220> FEATURE:
<223> OTHER INFORMATION: second lacO sequence (lacO2) (in bold in SEQ ID
      NO:34)

<400> SEQUENCE: 37
tgtggaattg tgagcgctca caattccaca                                     30

<210> SEQ ID NO 38
<211> LENGTH: 711
<212> TYPE: DNA
<213> ORGANISM: Artificial Sequence
<220> FEATURE:
<223> OTHER INFORMATION: sequence encoding Dasher green fluorescent
      protein of SEQ ID NO:34

<400> SEQUENCE: 38
atgacggcat tgactgaagg cgcaaaactg ttcgagaaag aaatccccta catcaccgaa    60
ctcgagggcg acgtagaggg catgaagttc atcatcaagg gcgagggaac gggcgacgcc   120
accaccggca ccatcaaggc gaagtatatc tgcaccacgg gagatctgcc ggttccctgg   180
gcgacgctgg tgtcgacctt gtcctacggc gtccaatgct tcgcgaagta ccccagtcac   240
atcaaagact tctttaagag cgccatgcca gaaggctaca cgcaggaacg gaccatctcg   300
```

```
ttcgaagggg atggggtcta caagacccgt gcgatggtga cgtacgagcg cgggtccatc      360
tacaaccggg tcactctgac cggtgagaac ttcaagaagg acggccacat tctgcgcaag      420
aacgtcgcct tccagtgtcc gccgtcgatc ctgtatatcc tgccggatac cgtgaacaac      480
ggtattcgcg tggaattcaa tcaggcctat gatatcgagg tgtcacgga gaagcttgtg       540 accaaatgca gccagatgaa tcgccctctg gccggctccg ccgctgtcca tatcccgcgg      600
taccaccata tcacctatca taccaagctc agcaaagacc gcgacgagag gcgggaccac      660
atgtgcctcg tggaagtggt gaaggccgtc gacctggaca cctatcagtg a               711
```

```
<210> SEQ ID NO 39
<211> LENGTH: 1083
<212> TYPE: DNA
<213> ORGANISM: Artificial Sequence
<220> FEATURE:
<223> OTHER INFORMATION: nucleotide sequence encoding wild-type lacI

<400> SEQUENCE: 39
```

```
atgaaaccag tgactttgta cgatgtagcg gaatatgcag gcgtaagcta ccagactgtg       60
tcccgtgtcg ttaaccaagc cagccacgtg agcgcgaaaa cgcgcgagaa ggttgaggca      120
gcaatggcgg aactgaatta cattccgaac cgtgttgctc aacagttggc cggcaagcag      180
agcctgctga ttggcgttgc gacctctagc ctggcgctgc acgcgagcag ccaaatcgtg      240
gcagcgatta agtctcgtgc ggatcaactg ggtgcgagcg tcgtggtgag catggtggaa      300
cgtagcggtg tcgaggcttg taaagcggca gttcacaatc tgctggccca gcgtgtcagc      360
ggcctgatta tcaattaccc gctggacgac caggacgcaa tcgctgttga ggcggcttgc      420
acgaatgtcc cagcactgtt cttggacgtt agcgatcaga ccccgattaa ctccatcatc      480
ttctcccatg aggacggcac ccgcctgggc gtcgaacatc tggttgcgct gggtcatcag      540
cagatcgcgc tgttggcggg tccgttgagc agcgtgagcg cgcgtctgcg tctggcgggc      600
tggcacaaat atctgacgcg caaccaaatc cagcctattg cggagcgcga aggtgattgg      660
agcgcaatgt ctggctttca gcaaacgatg cagatgctga atgaaggtat tgttccgacc      720
gcgatgctgg ttgttaacga tcagatggcc ctgggtgcga tgcgtgcaat caccgagagc      780
ggcctgcgcg ttggtgccga catttccgtc gtcggttatg acgacaccga ggatagctct      840
tgctacatcc caccgctgac caccattaaa caagattttc gtctgctggg tcaaaccagc      900
gtcgatcgcc tgctgcaatt gtcgcagggt caggccgtga aggtaatca actgctgccg       960 gtgagcctgg ttaagcgtaa gacgacgttg gcaccgaaca cccaaaccgc aagcccgcgt     1020
gctctggccg acagcctgat gcaactggcg cgtcaagtgt cgcgcctgga aagcggtcag     1080
taa                                                                    1083
```

```
<210> SEQ ID NO 40
<211> LENGTH: 12
<212> TYPE: DNA
<213> ORGANISM: Artificial Sequence
<220> FEATURE:
<223> OTHER INFORMATION: native MDH, large subunit (MCA0779) ribosome
      binding site with native spacer

<400> SEQUENCE: 40
tggaggagac ac                                                           12
```

```
<210> SEQ ID NO 41
<211> LENGTH: 13
```

<212> TYPE: DNA
<213> ORGANISM: Artificial Sequence
<220> FEATURE:
<223> OTHER INFORMATION: modified MDH, large subunit (MCA0779) ribosome
      binding site with modified spacer of SEQ ID NO:34

<400> SEQUENCE: 41
tggaggagac aca                                                        13

<210> SEQ ID NO 42
<211> LENGTH: 60
<212> TYPE: DNA
<213> ORGANISM: Artificial Sequence
<220> FEATURE:
<223> OTHER INFORMATION: putative promoter from the trfA-containing
      operon of plasmid RK2 (BN000925)

<400> SEQUENCE: 42
ttgacagcgg aaccaatgtt tagctaaact agagtctcct ttctcaagga gactttcgat    60

<210> SEQ ID NO 43
<211> LENGTH: 172
<212> TYPE: DNA
<213> ORGANISM: Artificial Sequence
<220> FEATURE:
<223> OTHER INFORMATION: putative Methylococcus capsulatus Bath 30S
      ribosomal protein S12 promoter with altered
      MDH ribosomal binding sequence

<400> SEQUENCE: 43
aattccaaaa aaggcttgca gcgatgtgag cctttttatt tttgtttgtt cgggcgtaag    60
tgcgcttgac atggcggctg ccagtaatta cgctgggtag ctttggtctt tcccgtattt   120
atgttgcgcg gttctgtgcg tgatgcgggt tggaatggtt ttggaggaga ca           172

<210> SEQ ID NO 44
<211> LENGTH: 77
<212> TYPE: DNA
<213> ORGANISM: Artificial Sequence
<220> FEATURE:
<223> OTHER INFORMATION: > putative Methylococcus capsulatus Bath 50S
      ribosomal protein L13 promoter with altered
      MDH ribosomal binding sequence

<400> SEQUENCE: 44
aaatgtgctt gtattccagt ggccgcttgg atagaattgc gcgctttgat tggggcgcca    60
gaacggtgga ggagaca                                                   77

<210> SEQ ID NO 45
<211> LENGTH: 315
<212> TYPE: PRT
<213> ORGANISM: Artificial Sequence
<220> FEATURE:
<223> OTHER INFORMATION: BenR transcriptional activator
      Protein_ABA06553.1 (Pseudomonas fluorescens) |gi|74422787

<400> SEQUENCE: 45

Met Thr Val Leu Leu Ser Glu Arg Ser Gln Ile Phe Gln Gly Ala Asp
1               5                   10                  15

Ala Tyr Ala Val Ser Asp Tyr Val Asn Gln His Val Gly Ser His Cys
            20                  25                  30

Ile Arg Leu Pro Pro Arg Gly Gln Pro Arg Ala Ser Ile Ser His Arg
        35                  40                  45

Thr Phe Ala Ser Leu Asp Leu Cys Arg Ile Ser Tyr Gly Ala Pro Val
    50                  55                  60

```
Arg Val Thr Ser Val Ala Leu Glu Thr Ile Tyr His Leu Gln Ile Leu
 65                  70                  75                  80

Leu Ser Gly His Cys Arg Ser Asn Ser Arg Gly Glu Asp Asp Val Phe
                 85                  90                  95

Gly Pro Gly Glu Ile Leu Leu Ile Asn Pro Asp Asp Pro Val Asp Leu
            100                 105                 110

Thr Tyr Ser Ala Asp Cys Glu Lys Phe Ile Ile Lys Leu Pro Val Arg
            115                 120                 125

Leu Leu Glu Asn Ala Cys Leu Glu Gln His Trp Ser Leu Pro Arg Ala
130                 135                 140

Gly Val Arg Phe Thr Thr Ala Arg His Ala Leu Ser Glu Met Gly Gly
145                 150                 155                 160

Phe Leu Pro Leu Leu Gly Leu Ile Cys His Glu Ala Glu Asn Ala Ala
                165                 170                 175

Glu Pro His Met Gln Gly Leu Tyr Glu Arg Ile Val Ala Asn Lys Leu
            180                 185                 190

Leu Ala Leu Leu Gly Ser Asn Val Ser Arg Val Thr Pro Arg Ala Ala
            195                 200                 205

His Gly Gly Phe Glu Ala Val His Glu Phe Ile Gln Gln His Leu
210                 215                 220

Gly Asp Asp Ile Ser Val Glu Gln Leu Met Ala Val Ala Asn Val Ser
225                 230                 235                 240

Glu Arg Ser Leu Tyr Ser Leu Phe Glu Arg Gln Val Gly Leu Ser Pro
                245                 250                 255

Arg Asp Tyr Val Arg Arg Cys Lys Leu Glu Arg Val His Ala Arg Leu
            260                 265                 270

Gln Leu Ser Ser Thr Arg Ser Val Thr Glu Val Ala Leu Asp His Gly
            275                 280                 285

Phe Met His Leu Gly Arg Phe Ser Glu Ala Tyr Arg Lys Arg Phe Gly
290                 295                 300

Glu Leu Pro Ser Gln Thr Trp Lys Arg His Arg
305                 310                 315
```

<210> SEQ ID NO 46
<211> LENGTH: 948
<212> TYPE: DNA
<213> ORGANISM: Pseudomonas fluorescens

<400> SEQUENCE: 46

```
atgaccgtgc tattgagtga gcgcagccag attttccagg gcgccgatgc ctacgcggtg     60
tcggactacg tcaaccagca tgtgggcagc cactgcattc gcctgcctcc caggggccag    120
ccccgggcaa gtatcagcca tcgcaccttc gccagcctgg acctgtgccg catcagctac    180
ggcgcaccgg tgcgggtcac gtcggtggcg ctggagacca tctaccacct gcagatcctc    240
ttgagcgggc attgccgctc caactcccgt ggcgaggatg atgtgttcgg ccgggggaa     300
atcctgctga tcaatccgga cgacccggta gacctgacct attcgccga ctgcgaaaaa     360
ttcatcatca aactgccggt cgcctgctg gaaaacgcct gctggagca gcactggagc    420
ctgccgcggg cggggtccg cttcacgacg gcccgccacg cgctcagtga atgggcggc     480
ttcctgccgt tgctcgggtt gatctgccat gaggcggaaa acgctgccga gccccacatg    540
caaggcctgt acgaacgcat cgtggccaac aagctgctgg cattgctggg cagcaatgtg    600
tcgcgggtga cccccgggc tgcccacggc ggtgggtttg aagcggtgca cgaatttatc    660
```

```
cagcagcacc tgggcgatga catcagcgtc gagcagttga tggccgtggc caacgtcagt    720
gaacgttcgc tgtacagcct gtttgagcgc aggtggggc tgtcgccgcg cgattacgta     780
cgccgctgca agctcgaacg cgtacatgca cgcttgcaac taagcagcac gcgcagcgtg    840
accgaggtgg cttttggacca tgggttcatg cacctaggac ggttttccga agcctatcgc    900
aaacgcttcg gcgaactgcc gtcgcagacc tggaaacgcc atcgttaa                948
```

<210> SEQ ID NO 47
<211> LENGTH: 948
<212> TYPE: DNA
<213> ORGANISM: Artificial Sequence
<220> FEATURE:
<223> OTHER INFORMATION: benR codon optimized for Methylococcus
      capsulatus Bath

<400> SEQUENCE: 47

```
atgaccgtcc ttttgagtga acgcagccaa attttcagg gagccgatgc ctatgccgtc     60
agtgactacg tcaaccaaca tgtgggctcg cactgcatca ggctgccacc gcggggccag   120
ccgcgggcga gcatctcgca ccgcaccttc gccagcctgg acctgtgccg catctcgtac   180
ggcgcacccg tccgcgtcac ctcggttgcg ctcgaaacga tctaccatct gcagatcctg   240
ttgtccggcc actgccggtc caattcgcgc ggtgaggatg acgtgtttgg gcccggcgag   300
atcctgctca ttaatccgga cgacccggtc gacctgacct acagcgcgga ttgcgagaaa   360
ttcataatca agctgccggt gcgcctcctt gagaacgcct gcttggagca gcattggtcg   420
ctgccgaggg ccggcgtccg cttcaccacg gcacggcatg cgctgagcga gatgggcggc   480
ttcctcccgc tcctcggtct gatctgtcac gaagccgaga acgctgccga gccgcacatg   540
caaggcctgt acgagcgcat cgtggcgaac aagctgctgg cgctgctggg atccaatgtg   600
tcccgcgtga cgccccgggc ggcgcatggt ggcggcttcg aagccgtcca tgagttcatc   660
cagcagcatc tcggcgacga catctccgtc gaacagctca tggctgtcgc gaacgtgtcc   720
gagcgctcgc tttattccct cttcgagcgc caggtcgggc tgagcccag ggactatgtg     780 cggcgctgca agctcgaacg cgttcatgcc cggctccagc tctcgtccac ccgcagcgtg    840
accgaagtgg ccctcgacca tggcttcatg cacctcgggc ggttctccga ggcgtatcgc    900
aaacggttcg gtgagctgcc ttcgcaaacc tggaagcgcc accggtag                 948
```

<210> SEQ ID NO 48
<211> LENGTH: 107
<212> TYPE: DNA
<213> ORGANISM: Artificial Sequence
<220> FEATURE:
<223> OTHER INFORMATION: Putative ben promoter and ribosomal binding
      site with spacer from DQ172832.1: 1009-1115
      (Pseudomonas fluorescens); 107 bp intergenic
      region between benR and benA

<400> SEQUENCE: 48

```
gcgacgtgcg cctggcggat agcgatgtgc aggcagcgga tattgacggg cagggcgagc     60
acgtacggtg agggcgcctg atacaagaac aacggagggc ccgcccc                  107
```

<210> SEQ ID NO 49
<211> LENGTH: 321
<212> TYPE: PRT
<213> ORGANISM: Pseudomonas putida plasmid pWW0

<400> SEQUENCE: 49

Met Asp Phe Cys Leu Leu Asn Glu Lys Ser Gln Ile Phe Val His Ala

```
1               5                   10                  15
Glu Pro Tyr Ala Val Ser Asp Tyr Val Asn Gln Tyr Val Gly Thr His
                20                  25                  30

Ser Ile Arg Leu Pro Lys Gly Gly Arg Pro Ala Gly Arg Leu His His
            35                  40                  45

Arg Ile Phe Gly Cys Leu Asp Leu Cys Arg Ile Ser Tyr Gly Gly Ser
        50                  55                  60

Val Arg Val Ile Ser Pro Gly Leu Glu Thr Cys Tyr His Leu Gln Ile
65                  70                  75                  80

Ile Leu Lys Gly His Cys Leu Trp Arg Gly His Gly Gln Glu His Tyr
                85                  90                  95

Phe Ala Pro Gly Glu Leu Leu Leu Asn Pro Asp Asp Gln Ala Asp
            100                 105                 110

Leu Thr Tyr Ser Glu Asp Cys Glu Lys Phe Ile Val Lys Leu Pro Ser
        115                 120                 125

Val Val Leu Asp Arg Ala Cys Ser Asp Asn Asn Trp His Lys Pro Arg
130                 135                 140

Glu Gly Ile Arg Phe Ala Ala Arg His Asn Leu Gln Gln Leu Asp Gly
145                 150                 155                 160

Phe Ile Asn Leu Leu Gly Leu Val Cys Asp Glu Ala Glu His Thr Lys
                165                 170                 175

Ser Met Pro Arg Val Gln Glu His Tyr Ala Gly Ile Ile Ala Ser Lys
            180                 185                 190

Leu Leu Glu Met Leu Gly Ser Asn Val Ser Arg Glu Ile Phe Ser Lys
        195                 200                 205

Gly Asn Pro Ser Phe Glu Arg Val Val Gln Phe Ile Glu Glu Asn Leu
    210                 215                 220

Lys Arg Asn Ile Ser Leu Glu Arg Leu Ala Glu Leu Ala Met Met Ser
225                 230                 235                 240

Pro Arg Ser Leu Tyr Asn Leu Phe Glu Lys His Ala Gly Thr Thr Pro
                245                 250                 255

Lys Asn Tyr Ile Arg Asn Arg Lys Leu Glu Ser Ile Arg Ala Cys Leu
            260                 265                 270

Asn Asp Pro Ser Ala Asn Val Arg Ser Ile Thr Glu Ile Ala Leu Asp
        275                 280                 285

Tyr Gly Phe Leu His Leu Gly Arg Phe Ala Glu Asn Tyr Arg Ser Ala
    290                 295                 300

Phe Gly Glu Leu Pro Ser Asp Thr Leu Arg Gln Cys Lys Lys Glu Val
305                 310                 315                 320

Ala
```

<210> SEQ ID NO 50
<211> LENGTH: 966
<212> TYPE: DNA
<213> ORGANISM: Pseudomonas putida plasmid pWW0

<400> SEQUENCE: 50
atggattttt gcttattgaa cgagaaaagt cagatcttcg tccacgccga gccctatgca    60
gtctccgatt atgttaacca gtatgtcggt acgcactcta ttcgcctgcc caagggcggg   120
cgcccggcag gcaggctgca ccacagaatc ttcggatgcc tcgacctgtg tcgaatcagc   180
tacggcggta gcgtgagggt aatctcgcct ggattagaga cctgttatca tctgcaaata   240
atactcaaag gccattgcct gtggcgtggc catggccagg agcactattt tgcgccgggc   300

| | |
|---|---|
| gaactattgc tgctcaatcc ggatgaccaa gccgacctga cctattcaga agattgcgag | 360 |
| aaatttatcg ttaaattgcc ctcagtggtc cttgatcggg catgcagtga caacaattgg | 420 |
| cacaagccga gggagggtat ccgtttcgcc gcgcgacaca atctccagca actcgatggc | 480 |
| tttatcaatc tactcgggtt agtttgtgac gaagcggaac atacaaagtc gatgcctcgg | 540 |
| gtccaagagc actatgcggg gatcatcgct tccaagctgc tcgaaatgct gggcagcaat | 600 |
| gtcagccgtg aaattttcag caaaggtaac ccgtctttcg agcgagtcgt tcaattcatt | 660 |
| gaggagaatc tcaaacggaa tatcagcctt gagcggttag cggagctggc gatgatgagt | 720 |
| ccacgctcgc tctacaattt gttcgagaag catgccggca ccacgccgaa gaactacatc | 780 |
| cgcaaccgca agctcgaaag catccgcgcc tgcttgaacg atcccagtgc caatgtgcgt | 840 |
| agtataactg agatagccct agactacggc ttcttacatt tgggacgctt cgctgaaaac | 900 |
| tataggagcg cgttcggcga gttgccttcc gacaccctgc gtcaatgcaa aaggaagtg | 960 |
| gcttga | 966 |

<210> SEQ ID NO 51
<211> LENGTH: 966
<212> TYPE: DNA
<213> ORGANISM: Artificial Sequence
<220> FEATURE:
<223> OTHER INFORMATION: xylS codon optimized for Methylococcus
    capsulatus Bath

<400> SEQUENCE: 51

| | |
|---|---|
| atggacttct gcctgcttaa tgaaaaatcc cagatctttg tccacgccga gccgtacgcc | 60 |
| gtgagcgact atgtgaacca atatgttggt acccattcga tccggctccc gaagggtggc | 120 |
| cgcccggcgg gcaggctcca tcaccgcata ttcggctgcc tcgatctctg ccgcatctcg | 180 |
| tacggcggca gcgtccgggt gatctcgccg ggtctggaaa cgtgctatca tctgcagatc | 240 |
| attctcaagg gccactgcct ctggcgggga catggccagg aacattactt cgcccctgga | 300 |
| gagctgctgc tcttgaaccc ggacgatcag gcagatttga cctactccga ggactgtgag | 360 |
| aagttcatcg tgaagctgcc cagcgtcgtc ctcgaccgcg cgtgctcgga taacaactgg | 420 |
| cataagccac gcgagggcat ccggttcgcg gcacggcaca atctgcaaca gcttgacggg | 480 |
| ttcatcaatc tcctgggcct cgtctgcgac gaagccgagc acactaagtc gatgcccagg | 540 |
| gtccaagagc attatgcggg catcatcgcg tccaagctgc tcgaaatgct cgggtccaac | 600 |
| gtgagccgcg agattttcag taagggcaac cccagcttcg agcgcgtcgt gcagttcatc | 660 |
| gaagagaacc tgaagcgcaa tatctccctg gagcgcctcg ccgagcttgc catgatgagt | 720 |
| ccgcgcagcc tctataacct gtttgagaaa catgcgggca ccacgcccaa gaattacatt | 780 |
| cgcaaccgca aactggagtc catccgcgct tgcctcaacg accgtcggc gaatgtccgg | 840 |
| tcgatcaccg agatcgccct ggactacggt ttcctgcacc tgggccggtt cgccgagaat | 900 |
| tatcgctccg ctttcggcga gctgccgtcg gacaccctgc gccagtgcaa aaagaagtg | 960 |
| gcgtga | 966 |

<210> SEQ ID NO 52
<211> LENGTH: 62
<212> TYPE: DNA
<213> ORGANISM: Artificial Sequence
<220> FEATURE:
<223> OTHER INFORMATION: Putative xylX promoter (Pm) and ribosomal
    binding site from pWW0 (Pseudomonas putida); 62 bp region
    upstream of xylX translational start site

```
<400> SEQUENCE: 52
ggctatctct agaaaggcct accccttagg ctttatgcaa cagaaacaat aataatggag      60
tc                                                                    62

<210> SEQ ID NO 53
<211> LENGTH: 6
<212> TYPE: DNA
<213> ORGANISM: Artificial Sequence
<220> FEATURE:
<223> OTHER INFORMATION: Consensus RBS

<400> SEQUENCE: 53 aggagg                                                                6

<210> SEQ ID NO 54
<211> LENGTH: 14
<212> TYPE: DNA
<213> ORGANISM: Artificial Sequence
<220> FEATURE:
<223> OTHER INFORMATION: benA ribosomal binding site with spacer from
      DQ172832.1: 1009-1115 (Pseudomonas fluorescens)

<400> SEQUENCE: 54
ggagggcccg cccc                                                       14
```